United States Patent
Boutherin-Falson et al.

(10) Patent No.: US 6,262,095 B1
(45) Date of Patent: Jul. 17, 2001

(54) USE OF TRICYCLIC DERIVATIVES OF 1,4-DIHYDRO-1,4-DIOXO-1H-NAPHTHALENE, NOVEL COMPOUNDS OBTAINED AND THEIR APPLICATION IN THERAPHY

(75) Inventors: Odile Boutherin-Falson, Palaiseau; Stéphanie Desquand-Billiald, Paris; Anita Favrou, Cachan; Michel Finet, Chatenay Malabry; Olivier Tembo, Mery sur Oise; Jean-Luc Torregrosa, Cachan; Sylvie Yannic-Arnoult, Epinay sur Orge; Florence Domagala-Le Marquer, Antony, all of (FR)

(73) Assignee: Laboratoire Innothera, Arcueil (FR)

( * ) Notice: Subject to any disclaimer, the term of this patent is extended or adjusted under 35 U.S.C. 154(b) by 0 days.

(21) Appl. No.: 09/043,831
(22) PCT Filed: Dec. 10, 1996
(86) PCT No.: PCT/FR96/01973
  § 371 Date: Oct. 14, 1998
  § 102(e) Date: Oct. 14, 1998
(87) PCT Pub. No.: WO97/21684
  PCT Pub. Date: Jun. 19, 1997

(30) Foreign Application Priority Data
Dec. 12, 1995 (FR) .................................................. 95 14683

(51) Int. Cl.[7] ....................... C07D 235/02; A61K 31/428
(52) U.S. Cl. ........................... 514/366; 514/375; 514/393
(58) Field of Search .................................. 514/366, 375, 514/393

(56) References Cited

FOREIGN PATENT DOCUMENTS

92/19211   11/1992   (WO) .

*Primary Examiner*—Robert Gerstl
(74) *Attorney, Agent, or Firm*—Kenyon & Kenyon

(57) ABSTRACT

The invention concerns the therapeutic use of tricyclic salts and their pharmaceutically acceptable salts having the general formula:

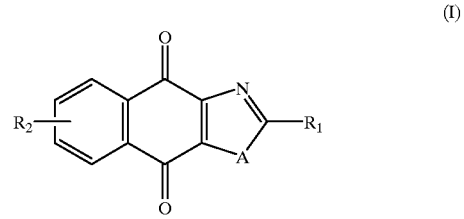

(I)

in which:

A is either a sulfur atom, an oxygen atom, or an $R_3N$ radical where $R_3$ is a hydrogen atom, a $C_1$–$C_5$ alkyl radical, or a substituted or unsubstituted aromatic ring, or a substituted or unsubstituted heteroaromatic ring.

$R_1$ is either a $C_1$–$C_5$ alkyl radical, or an $R_4NH$ radical where $R_4$ is a hydrogen atom, a $C_1$–$C_5$ alkyl radical, or a substituted or unsubstituted aromatic ring, or a substituted or unsubstituted heteroaromatic ring, or an aromatic ring that may or may not be substituted by one or more acceptor or donor groups, or a heteroaromatic ring having one or more heteroatoms, which may or may not be substituted by acceptor or donor groups.

$R_2$ is a hydrogen atom, halogen atom, a $C_1$–$C_5$ alkyl radical, an oxygen atom that may or may not be substituted by a $C_1$–$C_5$ alkyl radical, or an $NR_5R_5$, radical where $R_5$ and $R_5$, are, independently of each other, a hydrogen atom, an oxygen atom or monovalent $C_1$–$C_5$ organic radicals.

8 Claims, No Drawings

USE OF TRICYCLIC DERIVATIVES OF 1,4-DIHYDRO-1,4-DIOXO-1H-NAPHTHALENE, NOVEL COMPOUNDS OBTAINED AND THEIR APPLICATION IN THERAPHY

The present invention concerns the use of tricyclic derivatives and the use of their pharmaceutically acceptable salts for the preparation of a drug intended for the treatment of diseases connected with an alteration of venous and/or inflammatory edema, and concerns the novel compounds obtained. It refers more particularly to the tricyclic derivatives of 1,4-dihydro-1,4-dioxo-1H-naphthalene. The invention concerns the therapeutic application of all these compounds.

The synthesis of 1H-naphtho[2,3-d]imidazole-4,9-diones, substituted in position 2, is described in J. Heterocyl. Chem., 6(6), 909–916, 1969, by E. I. Carroll, and J. T. Blackwell. in addition, the document Zh. Org. Khim, 3(1), 162–168, 1967, by G. A. Efimova, and L. S. Efros, concerns the preparation of 1,2-dimethyl-1H-naphth[2,3-d]imidazole-4,9-dione. Finally, the document J. Am. Chem. Soc., 76, 4148–4152, 1954, by J. R. E. Hoover, and A. R. Day, shows the preparation of derivatives of 1H-naphthoimidazole-4,9-dione from 2,3-dichloro-1,4-dihydro-1,4-dioxonaphthalene.

The article in J. Prakt. Chem., 319(2), 254–258, 1977 by Ahmed S. Hammam and Osman Abdel-Magid describes the synthesis of 2-amido-3-chloro-1,4-dihydro-1,4-dioxonaphthalene from 2,3-dichloro-1,4-dihydro-1,4-dioxonaphthalene, a compound that can be used as an intermediate for the subsequent synthesis of naphtho[2,3-d]oxazole-4,9-diones, which may or may not be substituted at position 2. U.S. Pat. No. 3,039,925, of Jun, 19, 1962 and a German patent application of Apr. 24, 1967 by Gerhard Domagk, Karl W. Schellhammer, Siegfried Peterson, and Hans B. Koenig concern the synthesis of 2-methylnaphtho[2,3-d]oxazole-4,9-dione carried out by K. Fries and P. Ochwat (Berichte, 56, 1926 (1923)).

Japanese Patent 61,251,675 by S. Hiroyuki, as well as the article in Collect. Czech. Chem. Commun., 50(1), 71–79, 1985 by A. S. Hammam, and B. E. Bayoumy and in the document J. Heterocyclic Chem., 25, 901–906, 1988 by A. R. Katritzky and W. Q. Fan, describe the preparation of the naptho[2,3-d]thiazole-4,9-diones.

The tricyclic derivatives and their pharmaceutically acceptable salts according to the present invention have the general formula:

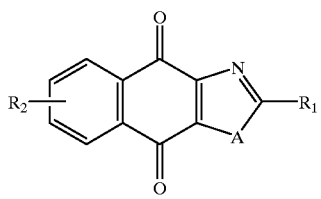

(I)

in which:
A is either a sulfur atom, an oxygen atom, or an $R_3N$ radical where $R_3$ is a hydrogen atom, a $C_1$–$C_5$ alkyl radical, or a substituted or unsubstituted aromatic ring, or a substituted or unsubstituted heteroaromatic ring.

$R_1$ is either a $C_1$–$C_5$ alkyl radical, or an $R_4NH$ radical where $R_4$ is a hydrogen atom, a $C_1$–$C_5$ alkyl radical, or a substituted or unsubstituted aromatic ring, or a substituted or unsubstituted heteroaromatic ring, or an aromatic ring that may or may not be substituted by one or more acceptor or donor groups, or a heteroaromatic ring having one or more heteroatoms, which may or may not be substituted by acceptor or donor groups.

$R_2$ is a hydrogen atom, halogen atom, a $C_1$–$C_5$ alkyl radical, an oxygen atom that may or may not be substituted by a $C_1$–$C_5$ alkyl radical, or an $NR_5R_{5'}$ radical where $R_5$ and $R_{5'}$ are, independently of each other, a hydrogen atom, an oxygen atom, or monovalent $C_1$–$C_5$ organic radicals.

In the invention the term "acceptor or donor groups" is defined as a $C_1$–$C_5$ alkyl radical, a halogen atom, or an oxygen atom, which may or may not be substituted by a $C_1$–$C_5$ alkyl radical, or an $NR_6R_{6'}$ where $R_6$ and $R_{6'}$ are, independently of each other, a hydrogen atom, an oxygen atom, or monovalent $C_1$–$C_5$ organic radicals.

The invention also concerns the following novel products:
4,9-dihydro-4,9-dioxo-1,2-dimethyl-1H-naphtho[2,3-d]imidazole sulfate,
4,9-dihydro-4,9-dioxo-2-(2-fluorophenyl)-1H-naphtho[2,3-d]imidazole,
4,9-dihydro-4,9-dioxo-2-(2-fluorophenyl)-naphtho[2,3-d]oxazole,
4,9-dihydro-4,9-dioxo-2-(3-fluorophenyl)naphtho[2,3-d]oxazole,
4,9-dihydro-4,9-dioxo-2-(4-fluorophenyl) naphtho[2,3-d]oxazole,
4,9-dihydro-4,9-dioxo-2-(2-methylphenyl) naphtho[2,3-d]oxazole,
4,9-dihydro-4,9-dioxo-2-(3-methylphenyl) naphtho[2,3-d]oxazole,
4,9-dihydro-4,9-dioxo-2-(4-methylphenyl) naphtho[2,3-d]oxazole,
2-(2-chlorophenyl)-4,9-dihydro-4,9-dioxonaphtho[2,3-d]oxazole,
2-(4-chlorophenyl)-4,9-dihydro-4,9-dioxonaphtho[2,3-d]oxazole,
4,9-dihydro-4,9-dioxo-2-(2-thienyl)-naphtho[2,3-d]oxazole,
4,9-dihydro-4,9-dioxo-2-(2-fluorophenyl)naphtho[2,3-d]thiazole,
4,9-dihydro-4,9-dioxo-2-(3-fluorophenyl)naphtho[2,3-d]thiazole,
4,9-dihydro-4,9-dioxo-2-(4-fluorophenyl)naphtho[2,3-d]thiazole,
2-(2,4-difluorophenyl)-4,9-dihydro-4,9-dioxonaphtho[2,3-d]thiazole,
4,9-dihydro-4,9-dioxo-2-(3-pyridyl)-naphtho[2,3-d]thiazole,
4,9-dihydro-4,9-dioxo-2-(4-pyridyl)-naphtho[2,3-d]thiazole sulfate,
4,9-dihydro-4,9-dioxo-2-(3-furyl)naphtho[2,3-d]thiazole,
2-(5-chlorofuran-2-yl)-4,9-dihydro-4,9-dioxonaphtho[2,3-d]thiazole,
4,9-dihydro-4,9-dioxo-2-(2-thienyl)-naphtho[2,3-d]thiazole,
4,9-dihydro-4,9-dioxo-2-(3-thienyl)-naphtho[2,3-d]thiazole,
4,9-dihydro-4,9-dioxo-2-phenylamino-naphtho[2,3-d]thiazole,
4,9-dihydro-4,9-dioxo-8-methoxy-2-phenylnaphtho[2,3-d]thiazole,
4,9-dihydro-4,9-dioxo-5-methoxy-2-phenylnaphtho[2,3-d]thiazole, 4,9-dihydro-4,9-dioxo-7-methoxy-2-phenylnaphtho[2,3-d]thiazole,
4,9-dihydro-4,9-dioxo-6-methoxy-2-phenylnaphtho[2,3-d]thiazole,
4,9-dihydro-4,9-dioxo-8-hydroxy-2-phenylnaphtho[2,3-d]thiazole,
4,9-dihydro-4,9-dioxo-2-(1-pyrrolyl)-naphtho[2,3-d]thiazole,
2-(5-bromofuran-2-yl)-4,9-dihydro-4,9-dioxonaphtho[2,3-d]thiazole,
2-(4,5-dibromofuran-2-yl)-4,9-dihydro-4,9-dioxonaphtho[2,3-d]thiazole,
2-(3-bromofuran-2-yl)-4,9-dihydro-4,9-dioxonaphtho[2,3-d]thiazole,
2-(3-bromofuran-2-yl)-4,9-dihydro-4,9-dioxonaphtho[2,3-d]thiazole,
2-(4-bromofuran-2-yl)-4,9-dihydro-4,9-dioxonaphtho[2,3-d]thiazole,
4,9-dihydro-4,9-dioxo-2-(5-nitrofuran-2-yl)naphtho[2,3-d]thiazole,
2-(5-aminofuran-2-yl)-4,9-dihydro-4,9-dioxonaphtho[2,3-d]thiazole,
2-(5-acetamidofuran-2-yl)-4,9-dihydro-4,9-dioxonaphtho[2,3-d]thiazole,
4,9-dihydro-4,9-dioxo-2-(5-hydroxymethylfuran-2-yl)naphtho[2,3-d]thiazole,
2-(5-acetoxymethylfuran-2-yl)-4,9-dihydro-4,9-dioxonaphtho[2,3-d]thiazole,
4,9-dihydro-4,9-dioxo-2-(5-methyl-2-furyl)naphtho[2,3-d]thiazole,
4,9-dihydro-2-(4,5-dimethyl-2-furyl)-4,9-dioxonaphtho[2,3-d]thiazole,
4,9-dihydro-4,9-dioxo-2-(5-phenyl-2-oxazolyl)naphtho[2,3-d]thiazole,
4,9-dihydro-4,9-dioxo-2-(2-thiazolyl)naphtho[2,3-d]thiazole,
4,9-dihydro-4,9-dioxo-6-fluoro-2-(2-furyl)naphtho[2,3-d]thiazole,
4,9-dihydro-4,9-dioxo-7-fluoro-2-(2-furyl)naphtho[2,3-d]thiazole,
4,9-dihydro-4,9-dioxo-6-fluoro-2-phenylnaphtho[2,3-d]thiazole,
4,9-dihydro-4,9-dioxo-7-fluoro-2-phenylnaphtho[2,3-d]thiazole,
4,9-dihydro-4,9-dioxo-6-fluoro-2-(5-methyl-2-furyl)naphtho[2,3-d]thiazole,
4,9-dihydro-4,9-dioxo-7-fluoro-2-(5-methyl-2-furyl)naphtho[2,3-d]thiazole,
4,9-dihydro-4,9-dioxo-6-fluoro-2-(4-fluorophenyl)naphtho[2,3-d]thiazole,
4,9-dihydro-4,9-dioxo-7-fluoro-2-(4-fluorophenyl)naphtho[2,3-d]thiazole,
4,9-dihydro-4,9-dioxo-6-fluoro-2-(4-methylphenyl)naphtho[2,3-d]thiazole,
4,9-dihydro-4,9-dioxo-7-fluoro-2-(4-methylphenyl)naphtho[2,3-d]thiazole,
4,9-dihydro-4,9-dioxo-5-fluoro-2-(2-furyl)naphtho[2,3-d]thiazole,
4,9-dihydro-4,9-dioxo-8-fluoro-2-(2-furyl)naphtho[2,3-d]thiazole,
6-chloro-4,9-dihydro-4,9-dioxo-2-(2-furyl)naphtho[2,3-d]thiazole,
7-chloro-4,9-dihydro-4,9-dioxo-2-(2-furyl)naphtho[2,3-d]thiazole,
4,9-dihydro-4,9-dioxo-2-(2-furyl)-5-methoxynaphtho[2,3-d]thiazole,
4,9-dihydro-4,9-dioxo-2-(2-furyl)-8-methoxynaphtho[2,3-d]thiazole,
4,9-dihydro-4,9-dioxo-2-(2-furyl)-5-hydroxynaphtho[2,3-d]thiazole,
4,9-dihydro-4,9-dioxo-2-(2-furyl)-8-hydroxynaphtho[2,3-d]thiazole,
4,9-dihydro-4,9-dioxo-2-(2-furyl)-6-methoxynaphtho[2,3-d]thiazole,
4,9-dihydro-4,9-dioxo-2-(2-furyl)-7-methoxynaphtho[2,3-d]thiazole,
4,9-dihydro-4,9-dioxo-2-furyl-6-methylnaphtho[2,3-d]thiazole,
4,9-dihydro-4,9-dioxo-2-furyl-7-methylnaphtho[2,3-d]thiazole,
4,9-dihydro-4,9-dioxo-6-methyl-2-phenylnaphtho[2,3-d]thiazole,
4,9-dihydro-4,9-dioxo-7-methyl-2-phenylnaphtho[2,3-d]thiazole,
4,9-dihydro-4,9-dioxo-2-furyl-5-methylnaphtho[2,3-d]thiazole,
4,9-dihydro-4,9-dioxo-2-furyl-8-methylnaphtho[2,3-d]thiazole,
4,9-dihydro-4,9-dioxo-5-methyl-2-phenylnaphtho[2,3-d]thiazole,
4,9-dihydro-4,9-dioxo-8-methyl-2-phenylnaphtho[2,3-d]thiazole.

The invention also concerns the following intermediate products:
1,4-dihydro-1,4-dioxo-5-methoxynaphthalene,
2,3-dibromo-1,4-dihydro-1,4-dioxo-5-methoxynaphthalene,
2-amino-3-bromo-1,4-dihydro-1,4-dioxo-5-methoxynaphthalene,
2-amino-3-bromo-1,4-dihydro-1,4-dioxo-8-methoxynaphthalene,
2,3-dibromo-1,4-dihydro-1,4-dioxo-6-fluoronaphthalene,
2-amino-3-bromo-6-fluoro-1,4-dihydro-1,4-dioxonaphthalene,
2-amino-3-bromo-7-fluoro-1,4-dihydro-1,4-dioxonaphthalene,
2,3-dibromo-1,4-dihydro-1,4-dioxo-5-fluoronaphthalene,
2-amino-3-bromo-1,4-dihydro-1,4-dioxo-5-fluoronaphthalene,
2-amino-3-bromo-1,4-dihydro-1,4-dioxo-8-fluoronaphthalene,
2-amino-3-chloro-1,4-dihydro-1,4-dioxo-6-methylnaphthalene,
2-amino-3-chloro-1,4-dihydro-1,4-dioxo-7-methylnaphthalene,
2,3-dibromo-1,4-dihydro-1,4-dioxo-5-methylnaphthalene,
2-amino-3-bromo-1,4-dihydro-1,4-dioxo-5-methylnaphthalene,
2-amino-3-bromo-1,4-dihydro-1,4-dioxo-8-methylnaphthalene.

The invention also refers to the use of tricyclic derivatives and their pharmaceutically acceptable salts, having the above general formula (I), for the preparation of a drug intended for:

the treatment of functional and organic venous insufficiency;

the treatment of hemorrhoid pathologies;

the treatment of migraine;

the treatment of dermatological and cardiovascular osteoarticular inflammations;

the treatment of states of shock consisting of a large drop in arterial pressure, more particularly in states of septic shock.

Specifically, the compounds of the present invention have the general formula (I) illustrated below:

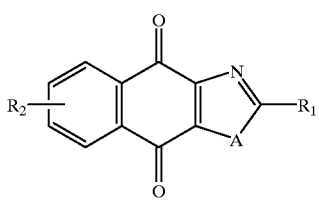

(I)

where:
A=—NH, —N—C$_6$H$_5$, —N—CH$_3$, O, S, N

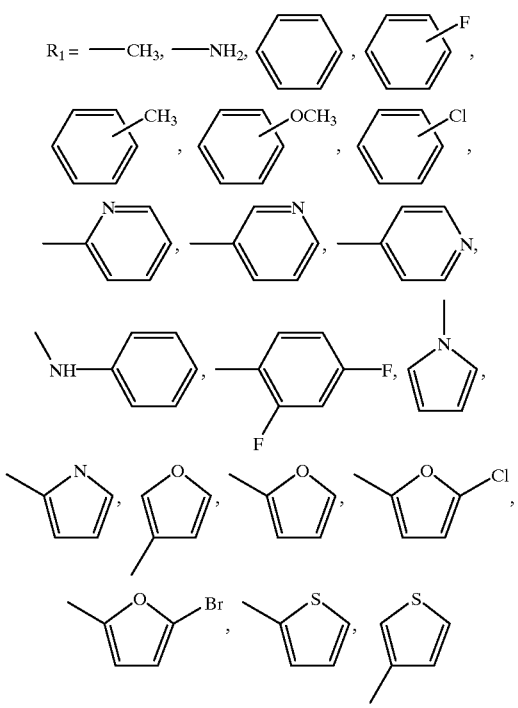

R$_2$=H, —OCH$_3$, —OH, —F, Cl, CH$_3$

The present invention also relates to the salts of the compounds of formula (I) of which salts can be prepared. These salts comprise the addition salts of mineral salts such as hydrochloric acid, hydrobromic acid, sulfuric acid, phosphoric acid, or nitric acid, and the addition salts of organic salts such as acetic acid, propionic acid, oxalic acid, citric acid, maleic acid, fumaric acid, succinic acid and tartaric acid.

The invention is illustrated by the following nonlimiting examples.

The examples indicated by a number correspond to novel compounds, whereas the examples indicated by a letter correspond to known compounds.

In all the examples, the analyses are carried out as indicated below:

Melting point: The analyses are carried out using an apparatus of the "Kofler bench" type LEICA-REICHERT model WME and they are not corrected.

Thin-layer chromatographies: The thin layer chromatographies are carried out using silica gel plates with a UV$_{254}$ fluorescence indicator, at a thickness of 0.25 mm, of the MACHEREY-NAGEL type (Reference 805 023). The elution solvents are indicated for each compound.

Mass spectra: The mass spectra are determined using a spectrometer of the AEI MS-50 type or a spectrometer of the FISONS VG PLATFORM type. The ionization mode is indicated for each example.

NMR spectra: The NMR spectra of $^1$H and $^{13}$C are determined using either a spectrometer of the JEOL type, at 270 MHZ and 68 MHZ, respectively, or a spectrometer of the BRUCKER type, at 400 MHZ and 100 MHZ, respectively. The deuterated solvents used are indicated for each analysis.

Infrared spectra: The infrared spectra are obtained using a spectrometer of the NICOLET 205 FT-IR type. They are determined at 1% (weight/weight) in a dispersion in KBr.

EXAMPLE 1

4,9-Dihydro-4,9-dioxo-1,2-dimethyl-1H-naphtho[2,3-d]imidazole sulfate

To a solution of 2 g (8.84 mmol) of 4,9-dihydro-4,9-dioxo-1,2-dimethyl-1H-naphtho[2,3-d]imidazole in 300 mL of a methanol/dichloromethane mixture (2/1) heated at 70° C., 1 mL of concentrated sulfuric acid is added. The reaction mixture is stirred at 70° C. for 2 h, then concentrated at reduced pressure, and the pale yellow precipitate that appears is filtered and washed with dichloromethane, then with ethyl ether, to produce 2 g of 4,9-dihydro-4,9-dioxo-1,2-dimethyl-1H-naphtho[2,3-d]imidazole sulfate, in the form of yellow crystals.

Yield: 70%; Melting point: >260° C.; Rf: 0.50 (CH$_2$Cl$_2$/Methanol, 97.5/2.5); $^1$H-NMR (DMSO d$_6$): δ (ppm); 8.05 (dd, 2H, H-5, H-8, J$_{H5-H6}$=J$_{H7-H8}$=8.85 Hz; J$_{H5-H7}$=J$_{H6-H8}$=1.73 Hz); 7.85 (m, 2H, H-6, H-7); 5.44 (s, 1H, NH+); 3.98 (s, 3H, CH$_3$); 2.53 (s, 3H, CH$_3$); $^{13}$C-NMR (DMSO, d$_6$): δ (ppm); 177.22, 175.44 (2C, C-4, C-9); 153.46 (1C, C-2); 138.96 (1C, C-3a); 134.10, 134.01 (2C, C-6, C-7); 132.30, 131.93 (3C, C-8a, C-9a, C-4a); 126.24, 126.13 (2C, C-5, C-8); 32.33 (1C, CH$_3$); 12.30 (1C, CH$_3$); IR (KBr): ν (cm$^{-1}$); 3414–2400 (broad NH$^+$ band); 1674 (C=O).

EXAMPLE 2

4,9-Dihydro-4,9-dioxo-2-(2-fluorophenyl)-1H-naphtho[2,3-d]imidazole

To a suspension of 1.37 g (7.29 mmol) of 2,3-diamino-1,4-dihydro-1,4-dioxonaphthalene in 50 mL of water, a solution of 0.77 mL (7.29 mmol) of 2-fluorobenzaldehyde in 5 mL of glacial acetic acid is added. After 5 h of reflux, the black solid obtained is filtered, then washed three times with 30 mL of water. The solid is then redissolved in 2 L of dichloromethane, the organic phase is washed three times with water, dried over calcium chloride, and evaporated to dryness to produce 1.50 g of chestnut brown crystals. The product is purified on a flash column (support: silica, conditioning: heptane, eluants: dichloromethane/heptane, 95/5, then dichloromethane/methanol, 99/1), resulting in the production—after evaporation of the solvents at reduced pressure—of 1.00 g of 4,9-dihydro-4,9-dioxo-2-(2-fluorophenyl)-1H-naphtho[2,3-d]imidazole in the form of yellow crystals.

Yield: 47%; Melting point: >260° C.; Rf: 0.56 (CH$_2$Cl$_2$/ethyl acetate, 92/8); MS (I.E.): m/z 292 (M+.); $^1$H-NMR (DMSO d$_6$): δ (ppm); 14.28 (s, 1H, NH); 8.12 (m, 2H, H-5, H-8); 8.00 (m, 1H, H-6'); 7.86 (m, 2H, H-6, H-7); 7.60 (m, 1H, H-3'); 7.44 (m, 2H, H-4', H-5'); $^{13}$C-NMR (DMSO d$_6$): d (ppm); 179.13, 175.03 (2C, C-4, C-9); 157.41 (1C, C-2'); 147.88 (1C, C-2); 133.85 (2C, C-6, C-7); 132.67 (3C, C-6', C-9a, C-3a); 130.62 (2C, C-4a, C-8a); 126.24, 124.82 (3C, C-5, C-8, C-5'); 116.62, 116.31 (2C, C-1', C-3'); IR (KBr): ν (cm$^{-1}$); 3339 (NH): 1683, 1665 (C=O).

EXAMPLE 3

4,9-Dihydro-4,9-dioxo-2-(2-fluorophenyl)-naphtho[2,3-d]oxazole

To a solution of 6.0 g (28.8 mmol) of 2-amino-3-chloro-1,4-dihydro-1,4-dioxonaphthalene in 120 mL of nitrobenzene, 17.10 mL (144.0 mmol) of 2-fluorobenzoic acid chloride are added with protection from light. After 10 min of stirring at 80° C., 0.20 mL of concentrated sulfuric acid is added. The reaction mixture is heated to reflux for 18 h. After complete cooling, ether is added to produce a yellow precipitate, which is filtered through fritted glass and washed with ether. This solid is then purified on a flash column (support: silica; conditioning: heptane; eluant: dichloromethane/heptane, 60/40) to produce 2.5 g of 4,9-dihydro-4,9-dioxo-2-(2-fluorophenyl)-naphtho[2,3-d]oxazole in the form of yellow crystals.

Yield: 30%; Melting point: >260° C.; Rf: 0.60 (CH$_2$Cl$_2$); MS (I.E.): m/z 293 (M+.); $^1$H-NMR (DMSO d$_6$): δ (ppm); 8.25 (m, 2H, H-5, H-8); 8.19 (m, 1H, H-6'); 7.95 (m, 2H, H-6, H-7); 7.76 (m, 1H, H-4'); 7.52 (m, 2H, H-3', H-5'); $^{13}$C-NMR (DMSO d$_6$): δ (ppm); 178.22, 173.06 (2C, C-4, C-9); 161.88 (1C, C-2); 158.08 (1C, C-2'); 150.67, 142.83 (2C, C-3a, C-9a); 135.37 (1C, C-6'); 134.64 (2C, C-6, C-7); 132.31, 131.94 (2C, C-4a, C-8a); 130.65 (1C, C-4'); 126.79, 126.47 (2C, C-5, C-8); 125.62 (1C, C-5'); 117.32 (1C, C-3'); 113.21 (1C, C-1'); IR (KBr): ν (cm$^{-1}$); 1693, 1680 (C=C).

EXAMPLE 4

4,9-Dihydro-4,9-dioxo-2-(3-fluorophenyl)-naphtho[2,3-d]oxazole

To a solution of 5.00 g (24 mmol) of 2-amino-3-chloro-1,4-dihydro-1,4-dioxonaphthalene in 50 mL of nitrobenzene, 14.6 mL (120 mmol) of 3-fluorobenzoic acid chloride are added; after 5 min of stirring, 0.50 mL of concentrated sulfuric acid is then added with protection from light. After 24 h of reflux and complete cooling, 200 mL of ether are added to the reaction mixture. The precipitate formed is filtered, then redissolved in 200 mL of dichloromethane, to which 100 mL of a glacial sodium hydroxide solution are added. After 6 h of stirring at this temperature, the organic phase is extracted, washed several times with water and dried over calcium chloride. The solid obtained after evaporation of the solvent is purified on a medium-pressure column (support: silica; conditioning heptane; eluant: dichloromethane/heptane, 50/50). The yellow crystals so obtained are uncolored and recrystallized in a dichloromethane/heptane mixture (volume/volume) to produce 0.50 g of 4,9-dihydro-4,9-dioxo-2-(3-fluorophenyl)-naphtho[2,3-d]oxazole in the form of yellow crystals.

Yield: 7%; Melting point: 230° C.; Rf: 0.50 (CH$_2$Cl$_2$/heptane, 95/5); MS (I.E.): m/z 293 (M+.); $^1$H-NMR (CDCl$_3$): δ (ppm); 8.31 (m, 1H, H-6'); 8.27 (m, 2H, H-5, H-8); 8.02 (s, 1H, H-2'); 7.83 (m, 2H, H-6, H-7); 7.63 (m, 1H, H-5'); 7.31 (m, 1H, H-4'); $^{13}$C-NMR (DMSO d$_6$): δ (ppm); 178, 173 (2C, C-4, C-9); 162.53 (1C, C-3'); 149.37 (1C, C-9a); 143.47 (1C, C-3a); 134.85, 134.46 (2C, C-6, C-7); 132.45, 132.08 (2C, C-4a, C-8a); 131.06 (1C, C-5'); 127.52, 127.11 (2C, C-5, C-8); 124.74 (1C, C-6'); 117.46, 117.15 (2C, C-2', C-4'); IR (KBr): ν (cm$^{-1}$); 1695, 1680 (C=O).

EXAMPLE 5

4,9-Dihydro-4,9-dioxo-2-(4-fluorophenyl)-naphtho[2,3-d]oxazole

To a solution of 6.22 g (30 mmol) of 2-amino-3-chloro-1,4-dihydro-1,4-dioxo-naphthalene in 60 mL of nitrobenzene, 18.00 mL (150 mmol) of 4-fluorobenzoic acid chloride are added with protection from light. After 10 min of stirring with reflux, 0.20 mL of concentrated sulfuric acid is added. After 12 h and complete cooling, ether is added to obtain a yellow precipitate which is filtered through fritted glass, washed with ether and purified on a flash column (support: silica; conditioning: heptane; eluant: dichloromethane/heptane, 60/40). The yellow powder obtained after evaporation of the solvent is uncolored, recrystallized in dichloromethane to produce 2.90 g of 4,9-dihydro-4,9-dioxo-2-(4-fluorophenyl)-naphtho[2,3-d]oxazole in the form of yellow crystals.

Yield: 33%; Melting point: >260° C.; Rf: 0.60 (CH$_2$Cl$_2$/heptane, 80/20); MS (I.E.): m/z 293 (M+.); $^1$H-NMR (CDCl$_3$): δ (ppm); 8.33 (m, 2H, H-2', H-6'); 8.28 (m, 2H, H-5, H-8); 7.82 (m, 2H, H-6, H-7); 7.26 (m, 2H, H-3', H-5'); $^{13}$C-NMR (CDCl$_3$): δ (ppm); 166.89 (1C, C-4'); 143.45 (1C, C-3a); 134.42 (2C, C-6, C-7); 132.86 132.55 (2C, C-4a, C-8a); 130.78 (2C, C-2', C-6'); 127.52, 127.07 (2C, C-5, C-8); 121.50 (1C, C-1'); 116.82, 116.50 (2C, C-3', C-5'); IR (KBr): ν (cm$^{-1}$); 1689, 1669 (C=O).

EXAMPLE 6

4,9-Dihydro-4,9-dioxo-2-(2-methylphenyl)-naphtho[2,3-d]oxazole

To a solution of 5.00 g (24 mmol) of 2-amino-3-chloro-1,4-dihydro-1,4-dioxonaphthalene in 37 mL (280 mmol) of 2-methylbenzoic acid chloride, 8 drops of concentrated sulfuric acid are added with protection from light. After 7 h of reflux and complete cooling, the ocher precipitate that forms is filtered through fritted glass, washed with ether, and purified on a flash column (support: silica; conditioning: heptane; eluant: dichloromethane/heptane, 50/50). The yellow powder obtained after evaporation of the solvent is uncolored, and recrystallized in dichloromethane to produce 2.34 g of 4,9-dihydro-4,9-dioxo-2-(2-methylphenyl)-naphtho[2,3-d]oxazole in the form of yellow crystals.

Yield: 34%; Melting point: 212° C.; Rf: 0.50 (CH$_2$Cl$_2$/heptane, 80/20); MS (I.E.): m/z 289 (M+.); $^1$H-NMR (CDCl$_3$): δ (ppm); 8.30 (m, 1H, H-6'); 8.27 (m, 2H, H-5, H-8); 7.81 (m, 2H, H-6, H-7); 7.47 (m, 1H, H-4'); 7.37 (m, 2H, H-3', H-5'); 2.84 (s, 3H, CH$_3$); $^{13}$C-NMR (CDCl$_3$): δ (ppm); 179.05, 173.50 (2C, C-4, C-9); 140.81 (1C, C-2'); 134.77 (2C, C-6, C-7); 133.50 (1C, C-3'); 132.50 (1C, C-4'); 130.80 (1C, C-6'); 127.91 127.49 (2C, C-5, C-8); 125.60 (1C, C-5'); 123.45 (1C, C-1'); 22.50 (1C, CH$_3$); IR (KBr): ν (cm$^{-1}$); 1668, 1678 (C=O).

EXAMPLE 7

4,9-Dihydro-4,9-dioxo-2-(3-methylphenyl)-naphtho[2,3-d]oxazole

To a solution of 5 g (24 mmol) of 2-amino-3-chloro-1,4-dihydro-1,4-dioxo-naphthalene in 70 mL of dioxane, one adds, with protection from light, 32.00 mL (240 mmol) of 3-methylbenzoic acid chloride; after 5 min of stirring, 0.50 mL of concentrated sulfuric acid is added. After 45 min of reflux and complete cooling, 200 mL of ether are added, and the precipitate that forms is eliminated by filtration. The red filtrate is evaporated to dryness, redissolved in dichloromethane, washed several times with water, dried and purified on a flash column (support: silica; conditioning: heptane; eluant: dichloromethane/heptane, 50/50). The yellow crystals formed after evaporation of the solvent are uncolored and recrystallized in dichloromethane to produce 3 g of 4,9-dihydro-4,9-dioxo-2-(3-methylphenyl)-naphtho[2,3-d]oxazole in the form of yellow crystals.

Yield: 43%; Melting point: 255° C.; Rf: 0.43 ($CH_2Cl_2$/heptane, 80/20); MS (I.E.): m/z 289 (M+.); $^1$H-NMR ($CDCl_3$): δ (ppm); 8.26 (m, 2H, H-5, H-8); 8.17 (s, 1H, H-2'); 8.13 (m, 1H, H-5'); 7.82 (m, 2H, H-6, H-7); 7.43 (m, 2H, H-4', H-6'); 2.48 (s, 3H, $CH_3$); $^{13}$C-NMR ($CDCl_3$): δ (ppm); 179.13, 173.72 (2C, C-4, C-9); 166.95 (1C, C-2); 150.65, 144.17 (2C, C-3a, C-9a); 139.62 (1C, C-3'); 134.81, 134.77; 134.32 (3C, C2', C-6, C-7); 132.86, 132.55 (2C, C-4a, C-8a); 129.54, 129.26 (2C, C-4', C-5'); 127.91, 127.49 (2C, C-5, C-8); 125.86 (1C, C-6'); 125.44 (1C, C-1'); 21.71 (1C, $CH_3$); IR (KBr): ν ($cm^{-1}$); 1693, 1678 (C=O).

EXAMPLE 8

4,9-Dihydro-4,9-dioxo-2-(4-methoxyphenyl)-naphtho[2,3-d]oxazole

To a solution of 5.0 g (24 mmol) of 2-amino-3-chloro-1,4-dihydro-1,4-dioxonaphthalene in 80 mL of dichloromethane, one adds, with protection from light and at ambient temperature, 16 mL (120 mmol) of 4-methoxybenzoic acid chloride, then 0.003 mL of concentrated sulfuric acid. After 3 h of reflux, the reaction mixture is evaporated to dryness; the black oily residue obtained is redissolved in 300 mL of dichloromethane, washed with a solution of 10N sodium hydroxide, then with water, and finally dried over calcium chloride. The product is then purified on a flash column (support: silica 6–35 mm; conditioning: heptane; eluant: dichloromethane/heptane, 60/40), to produce 4.1 g of 4,9-dihydro-4,9-dioxo-2-(4-methoxyphenyl)-naphtho[2,3-d]oxazole in the form of yellow-orangish crystals after recrystallization and color removal with animal charcoal.

Yield: 56%; Melting point: >260° C.; Rf: 0.44 ($CH_2Cl_2$/ethanol, 99/1); MS (I.E.): m/z 305 (M+.); $^1$H-NMR ($CDCl_3$): δ (ppm); 8.28 (dd, 2H, H-5, H-8, $J_{H5-H6}=J_{H7-H8}$=8.85 Hz, $J_{H5-H7}=J_{H6-H8}$=1.73 Hz); 8.24 (d, 2H, H-2', H-6', $J_{H2'-H3'}=J_{H5'-H6'}$=8.60 Hz); 7.80 (m, 2H, H-6, H-7); 7.05 (d, 2H, H-3', H-5', $J_{H2'-H3'}=J_{H5'-H6'}$=8.60 Hz); 3.92 (s, 3H, $CH_3$); IR (KBr): ν ($cm^{-1}$); 1750, 1680 (C=O).

EXAMPLE 9

2-(2-Chlorophenyl)-4,9-dihydro-4,9-dioxo-naphtho[2,3-d]oxazole

To a solution of 5 g (24 mmol) of 2-amino-3-chloro-1,4-dihydro-1,4-dioxonaphthalene in 60 mL of dioxane, 15.3 mL (120 mmol) of 2-chlorobenzoic acid chloride are added; after 5 min of stirring, 0.5 mL of concentrated sulfuric is added. The reaction mixture is heated to reflux for 4 h, and the precipitate obtained after evaporation of the dioxane at a reduced pressure is dissolved in 200 mL of dichloromethane. To this solution, 100 mL of a cold 10N sodium hydroxide solution are added. The mixture is stirred for 2 h. The organic phase is then extracted, washed several times with water and dried over calcium chloride. The solid residue obtained after evaporation of the solvent is purified on a medium-pressure column (support: silica; eluant: dichloromethane/heptane, 40/60). The product obtained is recrystallized after color removal in a heptane/dichloromethane mixture (1/1) to produce 5 g of 2-(2-chlorophenyl)-4,9-dihydro-4,9-dioxo-naphtho[2,3-d]oxazole in the form of light yellow crystals.

Yield: 67%; Melting point: 216° C.; Rf: 0.42 ($CH_2Cl_2$/heptane, 80/20); MS (I.E.): m/z 309, 311 (M+.); $^1$H-NMR ($CDCl_3$): δ (ppm); 8.26 (m, 3H, H-5, H-8, H-6'); 7.82 (m, 2H, H-6, H-7); 7.53 (m, 3H, H-3', H-4', H-5'); $^{13}$C-NMR ($CDCl_3$): δ (ppm); 134.99, 134.87 (3C, C-2', C-6, C-7); 133.78, 132.84, 132.18 (4C, C-3', C-4', C-5', C-6'); 132.38, 132.04 (2C, C-4a, C-8a); 128.04, 127.63 (2C, C-5, C-8); 124.80 (1C, C-1'); IR (KBr): ν ($cm^{-1}$); 1691, 1674 (C=O).

EXAMPLE 10

2-(4-Chlorophenyl)-4,9-dihydro-4,9-dioxo-naphtho[2,3-d]oxazole

To a solution of 5.0 g (24 mmol) of 2-amino-3-chloro-1,4-dihydro-1,4-dioxonaphthalene in 60 mL of dioxane, one adds at ambient temperature 15.3 mL (120 mmol) of 4-chlorobenzoic acid chloride and 0.5 mL of concentrated sulfuric acid. The reaction mixture is heated to reflux for 4 h, then evaporated to dryness, redissolved in 200 mL of dichloromethane, and neutralized at cold temperature with 100 mL of 10N sodium hydroxide. The organic phase is then washed three times with water and dried over calcium chloride. The red powder so obtained is purified on a flash column (support: silica; conditioning: heptane; eluant: dichloromethane/heptane, 70/30). The yellow crystals obtained after evaporation of the solvent are uncolored and recrystallized in dichloromethane to produce 2.5 g of 2-(4-chlorophenyl)- 4,9-dihydro-4,9-dioxo-naphtho[2,3-d]oxazole in the form of yellow crystals.

Yield: 34%; Melting point: >260° C.; Rf: 0.40 ($CH_2Cl_2$/heptane, 80/20); MS (I.E.): m/z 309, 311 (MH+.); $^1$H-NMR ($CDCl_3$): δ (ppm); 8.28 (m, 4H, H-5, H-8, H-2', H-6'); 7.82 (m, 2H, H-6, H-7); 7.55 (d, 2H, H-3', H-5', $J_{H2'-H3'}=J_{H5'-H6'}$=8.34 Hz); $^{13}$C-NMR ($CDCl_3$): δ (ppm); 178.55, 173.21 (2C, C-4, C-9); 165.31 (1C, C-2); 150.35, 144.03 (2C, C-3a, C-9a); 139.55 (1C, C-4'); 134.48, 134.43 (2C, C-6, C-7); 132.38, 132.04 (2C, C-4a, C-8a); 129.65, 129.49 (4C, C-2', C-3', C-5', C-6'); 127.55, 127.09 (2C, C-5, C-8); 123.63 (1C, C-1'); IR (KBr): ν ($cm^{-1}$); 1695, 1675 (C=O).

EXAMPLE 11

4,9-Dihydro-4,9-dioxo-2-(2-thienyl)-naphtho[2,3-d]oxazole

To a solution of 5.0 g (24 mmol) of 2-amino-3-chloro-1,4-dihydro-1,4-dioxonaphthalene in 50 mL of dichloromethane, one adds, with protection from light and at ambient temperature, 12.9 mL (120 mmol) of 2-thenoyl acid chloride, then 3 μL of concentrated sulfuric acid. After 21 h of reflux, the reaction mixture is evaporated to dryness and the black oily residue obtained is redissolved in 100 mL of dichloromethane and washed with a 10N sodium hydroxide solution, then with water, and finally dried over calcium chloride. The product is then purified on a flash column (silica 6–35 μm; conditioning: heptane; eluant: dichloromethane/heptane, 60/40), to produce 5.3 g of 4,9-dihydro-4,9-dioxo-2-(2-thienyl)naphtho[2,3-d]oxazole in the form of yellow-orangish crystals after recrystallization and color removal with animal charcoal.

Yield: 78%; Melting point: >260° C.; Rf: 0.41 (CH$_2$Cl$_2$); MS (I.E.): m/z 281 (M+.); $^1$H-NMR (CDCl$_3$): δ (ppm); 8.22 (dd, 2H, H-5, H-8, J$_{H5-H6}$=8.85 Hz, J$_{H5-H7}$=1.73 Hz); 8.06 (dd, 1H, H-5', J$_{H5'-H4'}$=3.49 Hz, J$_{H5'-H3'}$=1.00 Hz); 7.83 (m, 2H, H-6, H-7); 7.73 (dd, 1H, H-3', J$_{H3'-H4'}$=4.88 Hz, J$_{H3'-H5'}$=1.00 Hz); 7.27 (dd, 1H, H-4', J$_{H4'-H3'}$=4.88 Hz, J$_{H4'-H5'}$=3.49 Hz); IR (KBr): ν (cm$^{-1}$); 1687, 1667 (C=O).

EXAMPLE 12

4,9-Dihydro-4,9-dioxo-2-(2-fluorophenyl)-naphtho[2,3-d]thiazole

To a suspension of 5.0 g (24 mmol) of 2-amino-3-chloro-1,4-dihydro-1,4-dioxonaphthalene in 80 mL of water, 8.4 g (35 mmol) of nonahydrated sodium sulfide are added. The reaction mixture is then heated to reflux for approximately 20 min, then 20 mL of an aqueous solution containing 2.0 g of sodium sulfide are added. When the color of the medium has completely changed to blue, 1.95 mL (24 mmol) of 2-fluorobenzaldehyde and 6.36 mL of glacial acetic acid are added successively. After 1 h of reflux, the black semisolid product obtained is filtered, dried, and purified on a flash column (support: silica; conditioning: heptane; eluant: dichloromethane/heptane, 50/50). The greenish crystals formed after evaporation of the solvent are washed several times with ethanol and ether, then they are uncolored and recrystallized in dichloromethane to produce 2.0 g of 4,9-dihydro-4,9-dioxo-2-(2-fluorophenyl)-naphtho[2,3-d]thiazole in the form of yellow crystals.

Yield: 27%; Melting point: >260° C.; Rf: 0.60 (CH$_2$Cl$_2$); MS (I.E.): m/z 309 (M+.); $^1$H-NMR (CDCl$_3$): δ (ppm); 8.62 (m, 1H, H-6'); 8.30, 8.21 (2dd, 2H, H-5, H-8, J$_{H5-H6}$=J$_{H7-H8}$=8.85 Hz, J$_{H6-H8}$=J$_{H5-H7}$=1.73 Hz); 7.81 (m, 2H, H-6, H-7); 7.56 (m, 1H, H-4'); 7.29 (m, 2H, H-3', H-5'); $^{13}$C-NMR (CDCl$_3$): δ (ppm); 179.17 (2C, C-4, C-9); 169.20 (1C, C-2'); 153.47 (1C, C-2); 134.43, 134.09 (2C, C-6, C-7); 133.70, 133.56 (2C, C-4a, C-8a); 130.02 (1C, C-6'); 127.86, 126.97 (2C, C-5, C-8); 124.99 (1C, C-4'); 120.00 (1C, C-5'); 116.48, 115.90 (2C, C-1', C-3'); IR (KBr): ν (cm$^{-1}$); 1683, 1661 (C=O).

EXAMPLE 13

4,9-Dihydro-4,9-dioxo-2-(3-fluorophenyl)-naphtho[2,3-d]thiazole

To a solution of 5.0 g (24 mmol) of 2-amino-3-chloro-1,4-dihydro-1,4-dioxonaphthalene in 50 mL of water, a solution is added which contains 8.4 g (35 mmol) of nonahydrated sodium sulfide in 50 mL of water. The reaction mixture is heated to reflux for approximately 20 min. When the reaction medium turns blue, 2.50 mL (24 mmol) of 3-fluorobenzaldehyde and 6.36 mL of glacial acetic acid are added successively. After 2h of reflux, the black product obtained is filtered, dissolved in dichloromethane, washed with distilled water, dried over calcium chloride, filtered, and evaporated at reduced pressure. The black-green solid obtained is then purified on a flash column (support: silica; conditioning: heptane; eluant: dichloromethane/heptane, 50/50, then dichloromethane, then dichloromethane/methanol, 99/1). The solid obtained after evaporation of the solvent is washed several times with methanol, ethanol, and ether, then uncolored and recrystallized in dichloromethane to produce 4.0 g of 4,9-dihydro-4,9-dioxo-2-(3-fluorophenyl)-naphtho[2,3-d]thiazole in the form of yellow crystals.

Yield: 54%; Melting point: >260° C.; Rf: 0.56 (CH$_2$Cl$_2$); MS (I.E.): m/z 309 (M+.); $^1$H-NMR (CDCl$_3$): δ (ppm); 8.37, 8.25 (2dd, 2H, H-5, H-8, J$_{H5-H6}$=J$_{H7-H8}$=8.85 Hz, J$_{H6-H8}$=J$_{H5-H7}$=1.73 Hz); 7.95 (m, 2H, H-2', H-6'); 7.84 (m, 2H, H-6, H-7); 7.55 (m, 1H, H-5'); 7.25 (m, 1H, H-4'); IR (KBr): ν (cm$^{-1}$); 1676, 1661 (C=O).

EXAMPLE 14

4,9-Dihydro-4,9-dioxo-2-(4-fluorophenyl)naphtho[2,3-d]thiazole

To a suspension of 5.0 g (24 mmol) of 2-amino-3-chloro-1,4-dihydro-1,4-dioxonaphthalene in 130 mL of water, 8.4 g (35 mmol) of nonahydrated sodium sulfide are added. The reaction mixture is heated to reflux for 20 min, then 50 mL of an aqueous solution containing 1.0 g of sodium sulfate are added. The color of the medium changes completely to blue. 2.60 mL (24 mmol) of 4-fluorobenzaldehyde and 6.36 mL of glacial acetic acid are added successively. After 1 h of reflux, the greenish precipitate obtained is filtered, dried, and purified on a flash column (support: silica; conditioning: heptane; eluant: dichloromethane/heptane, 60/40). The yellow crystals formed after evaporation of the solvent are washed successively with the isopropanol and ether, then uncolored and recrystallized in dichloromethane to produce 2.0 g of 4,9-dihydro-4,9-dioxo-2-(4-fluorophenyl)naphtho[2,3-d]thiazole in the form of yellow crystals.

Yield: 27%; Melting point: >260° C.; Rf: 0.51 (CH$_2$Cl$_2$/heptane, 90/10); MS (I.E.): m/z 309 (M+.); $^1$H-NMR (CDCl$_3$): δ (ppm); 8.30, 8.21 (2dd, 2H, H-5, H-8, J$_{H5-H6}$=J$_{H8-H7}$=8.85 Hz, J$_{H5-H7}$=J$_{H8-H6}$=1.73 Hz); 8.12 (m, 2H, H-2', H-6'); 7.83 (m, 2H, H-6, H-7); 7.22 (m, 2H, H-3', H-5'); $^{13}$C-NMR (CDCl$_3$): δ (ppm); 179.17 (2C, C-4, C-9); 165.21 (1C, C-4'); 134.46, 134.04 (2C, C-6, C-7); 132.78, 132.43 (2C, C-4a, C-8a); 130.08, 129.96 (2C, C-2', C-6'); 127.88, 126.98 (2C, C-5, C-8); 116.74, 116.42 (2C, C-3', C-5'); IR (KBr): ν (cm$^{-1}$); 1678, 1659 (C=O).

EXAMPLE 15

2-(2,4-Difluorophenyl)-4,9-dihydro-4,9-dioxo-naphtho[2,3-d]thiazole

To 5.0 g (24.15 mmol) of 2-amino-3-chloro-1,4-dihydro-1,4-dioxonaphthalene in 150 mL of water, 150 mL of an aqueous solution containing 29.0 g (120.00 mmol) of nonahydrated sodium sulfide are added. The reaction mixture is heated to reflux for 20 min. The color of the medium changes completely to blue; 2.0 mL (18.00 mmol) of 2,4-difluorobenzaldehyde and 6.3 mL of glacial acetic acid are added successively. After 3 h of reflux, the solid formed is filtered, washed in distilled water, dried, and purified on a cake (support: silica; eluant: dichloromethane). The yellow crystals obtained after evaporation of the solvents are recrystallized in dichloromethane and uncolored with animal charcoal to produce 3.9 g of 2-(2,4-difluorophenyl)-4,9-dihydro-4,9-dioxo-naphtho[2,3-d]thiazole.

Yield: 97%; Melting point: >260° C.; Rf: 0.40 (CH$_2$Cl$_2$); MS (I.E.): m/z 327 (M+.); $^1$H-NMR (CDCl$_3$): δ (ppm); 8.55 (m, 1H, H-3'); 8.28, 8.24 (2dd, 2H, H-5, H-8, J$_{H5-H6}$=J$_{H7-H8}$=8.85 Hz, J$_{H5-H7}$=J$_{H6-H8}$=1.73 Hz); 7.84 (m, 2H, H-6, H-7); 7.10 (m, 2H, H-5', H-6'); $^{13}$C-NMR (CDCl$_3$): δ (ppm); 178.88, 177.93 (2C, C-4, C-9); 163.45 (1C, C-2); 134.87, 134.52 (2C, C-6, C-7); 133.44, 133.10, 131.61 (4C, C-3a, C-4a, C-8a, C-9a); 127.95, 127.18 (2C, C-5, C-8); 123.45 (1C, C-1'); 113.53, 113.21 (2C, C-2', C-4'); 105.56, 105.18, 104.79 (3C, C-3', C-5', C-6'); IR (KBr): ν (cm$^{-1}$); 1681, 1658 (C=O).

EXAMPLE 16

4,9-Dihydro-4,9-dioxo-2-(3-pyridyl)-naphtho[2,3-d]thiazole

To a suspension of 10.00 g (48.2 mmol) of 2-amino-3-chloro-1,4-dihydro-1,4-dioxonaphthalene in 100 mL of water, 13.88 g (74.5 mmol) of nonahydrated sodium sulfide are added. The reaction mixture, which is gradually heated to reflux, changes to a blue color starting at 60° C. The addition of 4.00 g (16.7 mmol) of concentrated sodium sulfide in the water is necessary to complete the change in color; 6 mL (60.6 mmol) of 3-pyridine carboxyaldehyde and 10 mL of glacial acetic acid are then added successively. After 2 h of reflux, and complete cooling, 300 mL of ethanol are added. The precipitate formed is eliminated by filtration. The filtrate is evaporated to dryness, redissolved in dichloromethane, washed several times with ether, then with water, dried, and purified on a medium-pressure column (support: silica; conditioning: heptane; eluant: dichloromethane/methanol, 100/0 to 99/1). The yellow crystals formed after evaporation of the solvent are washed with ethanol, then uncolored, and recrystallized in dichloromethane to produce 1.00 g of 4,9-dihydro-4,9-dioxo-2-(3-pyridyl)-naphtho[2,3-d]thiazole in the form of yellow crystals.

Yield: 7%; Melting point: 256° C.; Rf: 0.50 ($CH_2Cl_2$/methanol, 98/2); MS (I.E.): m/z 292 (M+.); $^1$H-NMR ($CDCl_3$): δ (ppm); 9.33 (d, 1H, H-2', J=1.83 Hz); 8.80 (d, 1H, H-6', $J_{H5'-H6'}$=3.36 Hz); 8.49 (d, 1H, H-4', $J_{H4'-H5'}$=7.93 Hz); 8.36, 8.26 (2dd, 2H, H-5, H-8, $J_{H5-H6}$=$J_{H7-H8}$=8.85 Hz, $J_{H5-H7}$=$J_{H6-H8}$=1.73 Hz); 7.84 (m, 2H, H-6, H-7); 7.50 (dd, 1H, H-5', $J_{H4'-H5'}$=7.93 Hz, $J_{H5'-H6'}$=3.36 Hz); 13C-NMR ($CDCl_3$): δ (ppm); 178.13, 177.78 (2C, C-4, C-9); 177.67 (1C, C-2); 155.18 (1C, C-3a); 152.87, 148.58 (2C, C-2', C-6'); 142.18 (1C, C-9a); 134.77, 134.31 (2C, C-6, C-7); 134.18 (1C, C-4'); 132.74, 132.01 (2C, C-4a, C-8a); 128.36 (1C, C-3'); 128.04, 127.16 (2C, C-5, C-8); 124.56 (1C, C-5'); IR (KBr): ν ($cm^{-1}$); 1680, 1660 (C=O).

EXAMPLE 17

4,9-Dihydro-4,9-dioxo-2-(4-pyridyl)-naphtho[2,3-d]thiazole sulfate

To a suspension of 500 mg (1.71 mmol) of 4,9-dihydro-4,9-dioxo-2-(4-pyridyl)-naphtho[2,3-d]thiazole in 60 mL of methanol, 60 mL of a methanol solution containing 0.18 mL (1.74 mmol) of 98% sulfuric acid are added. After 1 h of reflux and complete cooling, the yellow precipitate obtained is filtered, rinsed several times with ethylic ether, and dried. In this manner, 500 mg of 4,9-dihydro-4,9-dioxo-2-(4-pyridyl)-naphtho[2,3-d]thiazole sulfate are obtained, in the form of yellow crystals.

Yield: 75%; Melting point: >260° C.; Rf: 0.50 ($CH_2Cl_2$/methanol, 96/4); IR (KBr): ν ($cm^{-1}$); from 3100 and 2725 ($NH^+$); 1686, 1668 (C=O).

EXAMPLE 18

4,9-Dihydro-4,9-dioxo-2-(3-furyl)naphtho[2,3-d]thiazole

To 6.0 g (29 mmol) of 2-amino-3-chloro-1,4-dihydro-1,4-dioxonaphthalene, 100 mL of a freshly prepared aqueous solution are added, which contains 34.8 g (145 mmol) of nonahydrated sodium sulfide. The reaction mixture is stirred at 70° C. for 20 min, until a blue coloration is obtained; 2.5 mL (29 mmol) of 3-furaldehyde and 7.6 mL (133 mmol) of glacial acetic acid are then added successively. After 2h of stirring at 50° C., then for 1 h 40 min at ambient temperature, the dark yellow precipitate obtained is filtered and washed two times with 500 mL of water. In this manner, 7.0 g of crystals are obtained, which are redissolved in 500 mL of dichloromethane, washed three times with 750 mL of water, then dried over calcium chloride and filtered. After evaporation of the dichloromethane at reduced pressure, the orange crystals so obtained are purified by filtration over a silica bed (dichloromethane/heptane, 80/20) to produce 3.5 g of 4,9-dihydro-4,9-dioxo-2-(3-furyl)naphtho[2,3-d]thiazole in the form of yellow crystals, which are recrystallized in ethyl acetate after color removal with animal charcoal.

Yield: 43%; Melting point: 245° C.; Rf: 0.58 ($CH_2Cl_2$); MS (I.E.): m/z 281 (M+.); $^1$H-NMR ($CDCl_3$): δ (ppm); 8.34 (dd, 1H, H-5 or H-8, $J_{H5-H6}$=$J_{H7-H8}$=8.85 Hz, $J_{H5-H7}$=$J_{H6-H8}$=1.73 Hz); 8.28 (dd, 1H, H-2', $J_{H2'-H5'}$=1.50 Hz, $J_{H2'-H4'}$=0.90 Hz); 8.23 (dd, 1H, H-5 or H-8, $J_{H5-H6}$=$J_{H7-H8}$=8.85 Hz, $J_{H5-H7}$=$J_{H6-H8}$=1.73 Hz); 7.81 (m, 2H, H-6, H-7); 7.56 (t, 1H, H-5', $J_{H2'-H5'}$=1.50 Hz); 6.98 (dd, 1H, H-4', $J_{H2'-H4'}$=0.90 Hz, $J_{H4'-H5'}$=1.80 Hz); $^{13}$C-NMR ($CDCl_3$): δ (ppm); 178.28, 177.83 (2C, C-4, C-9); 167.28 (1C, C-2); 155.05 (1C, C-3a); 144.77, 143.90 (2C, C-2', C-5'); 140.77 (1C, C-9a); 134.39, 134.06 (2C, C-6, C-7); 133.04, 132.63 (2C, C-4a, C-8a); 127.86, 126.90 (2C, C-5, C-8); 120.80 (1C, C-3'); 109.19 (1C, C-4'); IR (KBr): ν ($cm^{-1}$); 1678, 1656 (C=O).

EXAMPLE 19

2-(5-Chloro-furan-2-yl)-4,9-dihydro-4,9-dioxo-naphtho[2,3-d]thiazole

To a solution of 1.78 g (6.3 mmol) of 4,9-dihydro-4,9-dioxo-2-(2-furyl)-naphtho[2,3-d]thiazole in 600 mL of chloroform, gaseous chlorine is bubbled in at 0° C. for 2 min. The reaction mixture is stirred for an additional 10 min, until a light yellow solution is obtained. The excess chlorine is then eliminated by passing an argon flow. The yellow solid obtained after evaporation at reduced pressure is then purified on a flash column (silica 6–35 μm; conditioning: heptane; eluant: dichloromethane/heptane, 50/50) to produce 0.43 g of pale yellow crystals. After filtration on a silica bed, 0.40 g of 2-(5-chlorofuran-2-yl)-4,9-dihydro- 4,9-dioxo-naphtho[2,3-d]thiazole is obtained in the form of yellow crystals after recrystallization and color removal with animal charcoal.

Yield: 20%; Melting point: 257.7° C.; Rf: 0.42 ($CH_2Cl_2$); MS (I.E.): m/z 315 (M+.); $^1$H-NMR ($CDCl_3$): δ (ppm); 8.33 (dd, 1H, H-5 or H-8, $J_{H5-H6}$=8.85 Hz, $J_{H5-H7}$=1.73 Hz); 8.23 (dd, 1H, H-5 or H-8, $J_{H5-H6}$=8.85 Hz, $J_{H5-H7}$=1.73 Hz); 7.81 (m, 2H, H-6, H-7); 7.43 (d, 1H, H-3', $J_{H3'-H4'}$=3.58 Hz); 6.45 (d, 1H, H-4', $J_{H3'-H4'}$=3.58 Hz); $^{13}$C-NMR ($CDCl_3$): δ (ppm); 178.10, 177.92 (2C, C-4, C-9); 163.94 (1C, C-2); 141.10 (1C, C-2'); 140.78 (1C, C-3a); 139.58 (1C, C-9a); 134.40, 134.17 (2C, C-6, C-7); 133.10, 132.68 (2C, C-4a, C-8a); 127.86, 126.95 (2C, C-5, C-8); 115.65 (1C, C-3'); 113.34 (1C, C-4'); IR (KBr): ν ($cm^{-1}$); 1678, 1652 (C=O).

EXAMPLE 20

4,9-Dihydro-4,9-dioxo-2-(2-thienyl)-naphtho[2,3-d]thiazole

To 4.00 g (19 mmol) of 2-amino-3-chloro-1,4-dihydro-1,4-dioxonaphthalene, 150 mL of a freshly prepared aqueous solution containing 22.80 g (95 mmol) of nonahydrated sodium sulfide are added. The reaction mixture is heated at 80° C. for 20 min, until a blue coloration is obtained; 1.8 mL (19 mmol) of 2-thiophene carboxyaldehyde and 5.0 mL (87 mmol) of glacial acetic acid are then added successively. After 2 h of stirring, the black-chestnut brown precipitate obtained is filtered, then dissolved in 350 mL of dichloromethane. The organic phase is washed three times with 150 mL of water, dried over calcium chloride, and filtered. The orange solid obtained after evaporation of the dichloromethane at reduced pressure is uncolored with animal charcoal and recrystallized in dichloromethane to produce 2.71 g of 4,9-dihydro-4,9-dioxo-2-(2-thienyl)naphtho[2,3-d] thiazole in the form of red-orangish crystals.

Yield: 48%; Melting point: >260° C.; Rf: 0.58 ($CH_2Cl_2$); MS (I.E.): m/z 297 (MH+.); $^1$H-NMR ($CDCl_3$): δ (ppm); 8.32 (dd, 1H, H-5 or H-8, $J_{H5-H6}=J_{H7-H8}$=8.85 Hz, $J_{H5-H7}$= $J_{H6-H8}$=1.73 Hz); 8.21 (dd, 1H, H-5 or H-8, $J_{H5-H6}=J_{H7-H8}$= 8.85 Hz, $J_{H5-H7}=J_{H6-H8}$=1.73 Hz); 7.82 (m, 3H, H-6, H-7, H-5'); 7.62 (dd, 1H, H-3', $J_{H3'-H4'}$=4.88 Hz, $J_{H3'-H5'}$=1.00 Hz); 7.18 (dd, 1H, H-4', $J_{H3'-H4'}$=4.88 Hz, $J_{H4'-H5'}$=3.49 Hz); $^{13}$C-NMR ($CDCl_3$): δ (ppm); 178.32, 177.92 (2C, C-4, C-9); 169.34 (1C, C-2); 155.14 (1C, C-3a); 135.50 (1C, C-9a); 134.37, 134.02 (2C, C-6, C-7); 132.78, 132.43 (2C, C-4a, C-8a); 130.19 (1C, C-4'); 128.50 (1C, C-3'); 127.84, 127.61 (2C, C-5, C-8); 126.86 (C-5'); IR (KBr): ν ($cm^{-1}$); 1676, 1654 (C=O).

EXAMPLE 21

4,9-Dihydro-4,9-dioxo-2-(3-thienyl)-naphtho[2,3-d]thiazole

To 4.0 g (19 mmol) of 2-amino-3-chloro-1,4-dihydro-1, 4-dioxonaphthalene, 90 mL of a freshly prepared aqueous solution containing 22.8 g (95 mmol) of nonahydrated sodium sulfide are added. The reaction mixture is heated at 90° C. for 20 min, until a blue coloration is obtained; 1.8 mL (19 mmol) of 3-thiophene carboxyaldehyde and 5.0 mL (87 mmol) of glacial acetic acid are then added successively. After 2 h of stirring at 90° C., the yellow-greenish precipitate obtained is filtered, washed three times with 400 mL of water, and dried. The crystals are redissolved in 200 mL of isopropanol, stirred at ambient temperature for 1 h, then filtered, dried, and recrystallized in dichloromethane after color removal with animal charcoal to produce 4.0 g of 4,9-dihydro-4,9-dioxo-2-(3-thienyl)-naphtho[2,3-d]thiazole in the form of yellow-ocher crystals.

Yield: 70%; Melting point: 258° C.; Rf: 0.55 ($CH_2Cl_2$/ methanol, 95.5/0.5); MS (I.E.): m/z 297 (MH+.); $^1$H-NMR ($CDCl_3$): δ (ppm); 8.37 (dd, 1H, H-5 or H-8, $J_{H5-H6}$ ou $J_{H7-H8}$=8.85 Hz, $J_{H5-H7}$ ou $J_{H6-H8}$=1.73 Hz); 8.23 (m, 2H, H-5 or H-8, H-2'); 7.81 (m, 2H, H-6, H-7); 7.71 (d, 1H, H-5', $J_{H4'-H5'}$=4.88 Hz); 7.48 (dd, 1H, H-4', $J_{H4'-H5'}$=4.88 Hz, $J_{H2'-H4'}$=2.99 Hz); $^{13}$C-NMR ($CDCl_3$): δ (ppm); 178.32, 177.92 (2C, C-4, C-9); 169.34 (1C, C-2); 155.14 (1C, C-3a); 140.69 (1C, C-9a); 134.36, 134.04 (2C, C-6, C-7); 133.09, 132.71 (2C, C-4a, C-8a); 128.23 (1C, C-4'); 127.84 (1C, C-5'); 127.61, 126.89, 126.59 (3C, C-5, C-8, C-2'); IR (KBr): ν ($cm^{-1}$); 1674, 1655 (C=O).

EXAMPLE 22

4,9-Dihydro-4,9-dioxo-2-phenylamino-naphtho[2,3-d]thiazole

To a solution of 200 mg (0.8 mmol) of 2-chloro-4,9-dihydro-4,9-dioxo-naphtho[2,3-d]thiazole in 100 mL of ethanol, 730 μL (8 mmol) of aniline are added at 80° C. The reaction mixture is heated to reflux for 3.5 h; the red precipitate obtained is filtered after cooling, then purified on a cake (support: silica 6–35 μm; eluant: dichloromethane/ heptane, 20/80 to 100/0, then dichloromethane/ethyl acetate, 99.5/0.5 to 0/100). The clean fractions are combined, then filtered through micropores; the solvent is evaporated at reduced pressure to produce 196 mg of 4,9-dihydro-4,9-dioxo-2-phenylamino-naphtho[2,3-d]thiazole in the form of red crystals.

Yield: 80%; Melting point: >260° C.; Rf: 0.44 ($CH_2Cl_2$/ ethyl acetate, 90/10); MS (I.E.): m/z 306 (M+.); $^1$H-NMR (DMSO $d_6$): δ (ppm); 11.34 (s, 1H, NH); 8.09 (m, 2H, H-5, H-8); 7.86 (m, 2H, H-6, H-7); 7.70 (m, 2H, H-2', H-6'); 7.44 (m, 2H, H-3', H-5'); 7.14 (m, 1H, H-4'); $^{13}$C-NMR (DMSO $d_6$): δ (ppm); 178.04, 177.31 (2C, C-4, C-9); 167.72 (1C, C-2); 154.61 (1C, C-3a); 145.95 (1C, C-9a); 139.49 (1C, C-1'); 134.02, 133.93 (2C, C-6, C-7); 132.79, 132.06 (2C, C-4a, C-8a); 129.36 (2C, C-3', C-5'); 126.76, 125.73 (2C, C-5, C-8); 123.68 (1C, C-4'); 118.60 (2C, C-2', C-6'); IR (KBr): ν ($cm^{-1}$); 3228 (NH); 1677, 1632 (C=O).

EXAMPLES 23 AND 24

4,9-Dihydro-4,9-dioxo-8-methoxy-2-phenyl-naphtho [2,3-d]thiazole and

4,9-Dihydro-4,9-dioxo-5-methoxy-2-phenyl-naphtho [2,3-d]thiazole

Synthesis Intermediates:
  1,4-Dihydro-1,4-dioxo-5-methoxy-naphthalene

To a solution of 26.45 g (0.147 mol) of 1,4-dihydro-1,4-dioxo-5-hydroxynaphthalene in 1300 mL of dichloromethane, one adds dropwise 39 mL (0.303 mol) of iodomethane, then 73.50 g of silver oxide. The reaction mixture is stirred for 72 h, then filtered. The filtrate is dried over calcium chloride, then evaporated at reduced pressure. 28.50 g of orange crystals are produced, which are purified on a cake (support: silica 40–60 mm; eluant: heptane/ethyl acetate, 70/30 to 0/100) to produce 23.80 g of 1,4-dihydro-1,4-dioxo-5-hydroxynaphthalene.

Yield: 86%; Melting point: 188° C.; Rf: 0.50 (Ethyl acetate/heptane, 50/50); $^1$H-NMR ($CDCl_3$): δ (ppm); 7.72 (m, 2H, H-6, H-8); 7.32 (dd, 1H, H-7, $J_{H6-H7}=J_{H7-H8}$=7.63 Hz); 6.88 (m, 2H, H-2, H-3); 4.01 (s, 3H, $OCH_3$).

2,3-Dibromo-1,4-dihydro-1,4-dioxo-5-methoxynaphthalene

To a solution of 3.5 g (18.6 mmol) of 1,4-dihydro-1,4-dioxo-5-methoxynaphthalene in 135 mL of chloroform, 3.05 g (37.2 mmol) of sodium acetate and 3 mL (58.4 mmol) of bromine are added. The reaction medium is stirred for 48 h. The acetate salts formed are filtered. The filtrate is washed with distilled water, dried over calcium chloride, then evaporated at reduced pressure to produce 7.3 g of 1,4-dihydro-1,4-dioxo-2,3-dibromo-5-methoxynaphthalene in the form of orange crystals.

Yield: 100%; Melting point: 190° C.; $^1$H-NMR (DMSO $d_6$): δ (ppm); 7.80 (dd, 1H, H-8, $J_{H7-H8}$=7.85 Hz, $J_{H6-H8}$= 1.53 Hz); 7.73 (dd, 1H, H-7, $J_{H6-H7}$=8.34 Hz, $J_{H6-H8}$=7.85 Hz); 7.37 (m, 1H, H-6); 3.95 (s, 3H, $OCH_3$).

2-Amino-3-bromo-1,4-dihydro-1,4-dioxo-5-methoxynaphthalene and
  2-Amino-3-bromo-1,4-dihydro-1,4-dioxo-8-methoxynaphthalene To a solution of 500.0 mg (1.5 mmol) of 2,3-dibromo-1, 4-dihydro-1,4-dioxo-5-methoxynaphthalene in 25 mL of tetrahydrofuran, a drop of ammonia is added. The color of the reaction medium turns black. A current of ammonia is passed through the medium for 2 h at 20° C. The raw product obtained after evaporation of the solvent is purified on cake (support: silica; eluant: dichloromethane/heptane, 80/20) to produce 347.3 g of a mixture of 2-amino-3-bromo-1,4-dihydro-1,4-dioxo-5-methoxynaphthalene and 2-amino-3-bromo-1,4-dihydro-1,4-dioxo-8-methoxynaphthalene.
Overall Yield: 82%

2-Amino-3-bromo-1,4-dihydro-1,4-dioxo-8-methoxynaphthalene $^1$H-NMR (DMSO d$_6$): δ (ppm); 7.78 (d, 1H, H-8, $J_{H7\text{-}H8}$=7.94 Hz); 7.67 (dd, 1H, H-7, $J_{H6\text{-}H7}$=8.54 Hz, $J_{H7\text{-}H8}$=7.94 Hz); 7.25 (d, 1H, H-6, $J_{H6\text{-}H7}$=8.54 Hz); 3.99 (s, 3H, OCH$_3$); 1.73 (s, 2H, NH$_2$).

2-Amino-3-bromo-1,4-dihydro-1,4-dioxo-5-methoxynaphthalene $^1$H-NMR (DMSO d$_6$): δ (ppm); 7.73 (d, 1H, H-8, $J_{H7\text{-}H8}$=8.57 Hz); 7.61 (t, 1H, H-7, $J_{H7\text{-}H6}$=$J_{H7\text{-}H8}$=8.57 Hz); 7.34 (d, 1H, H-6, $J_{H6\text{-}H7}$=8.57 Hz); 3.97 (s, 3H, OCH$_3$); 1.73 (s, 2H, NH$_2$).

4,9-Dihydro-4,9-dioxo-8-methoxy-2-phenylnaphtho[2,3-d]thiazole (Example 23) and 4,9-dihydro-4,9-dioxo-5-methoxy-2-phenyl-naphtho[2,3-d]thiazole (Example 24)

To a solution of 93.70 g (389.00 mmol) of nonahydrated sodium sulfide in 400 mL of water, 18.30 g (64.87 mmol) of a (1/1) mixture of 2-amino-3-bromo-5-methoxy-1,4-dihydro-1,4-dioxo-naphthalene and 2-amino-3-bromo-8-methoxy-1,4-dihydro-1,4-dioxonaphthalene are added. The reaction medium is heated to reflux until a blue coloration is obtained; 6.6 mL (64.87 mmol) of benzaldehyde are added, then 22.3 mL of glacial acetic acid are added dropwise successively. After 1 h of reflux, and complete cooling, the precipitate obtained is filtered, washed with ethanol, and redissolved in chloroform. The organic phase is washed with water, then dried over calcium chloride; 16.50 g of yellow crystals are produced after evaporation of the solvents at reduced pressure, then they are purified on a flash column (support: silica 40–60 mm; eluant: dichloromethane/ethyl acetate, 100/0 to 97/3) to produce, after color removal and recrystallization in dichloromethane, 8.90 g of 4,9-dihydro-4,9-dioxo-8-methoxy-2-phenylnaphtho[2,3-d]thiazole (Example 23) and 2.29 g of 4,9-dihydro- 4,9-dioxo-5-methoxy-2-phenylnaphtho[2,3-d]thiazole (Example 24) in the form of yellow crystals.

4,9-Dihydro-4,9-dioxo-8-methoxy-2-phenylnaphtho[2,3-d]thiazole (Example 23)

Yield: 42%; Melting point: >260° C.; Rf: 0.55 (CH$_2$Cl$_2$/ethyl acetate, 90/10); MS (I.E.): m/z 321 (M+.); $^1$H-NMR (CDCl$_3$): δ (ppm); 8.14 (dd, 2H, H-2', H-6', $J_{H2'\text{-}H3'}$=$J_{H5'\text{-}H6'}$=6.10 Hz, $J_{H2'\text{-}H4'}$=$J_{H4'\text{-}H6'}$=1.80 Hz); 7.90 (d, 1H, H-5, $J_{H5\text{-}H6}$=7.63 Hz); 7.73 (dd, 1H, H-6, $J_{H5\text{-}H6}$=7.60 Hz, $J_{H6\text{-}H7}$=8.50 Hz); 7.52 (m, 3H, H-3', H-4', H-5'); 7.39 (d, 1H, H-7, $J_{H6\text{-}H7}$=8.50 Hz); 4.06 (s, 3H, OCH$_3$); $^{13}$C-NMR (CDCl$_3$): δ (ppm); 177.95 (1C, C-9); 177.58 (1C, C-4); 161.00 (1C, Cquat); 135.98 (1C, Cquat); 135.01 (1C, C-6); 132.23 (1C, C-4'); 129.20 (2C, C-3', C-5'); 127.79 (2C, C-2', C-6'); 119.78, 119.02 (2C, C-5, C-7); 56.74 (OCH$_3$); IR (KBr): ν (cm$^{-1}$); 1671 (C=O).

4,9-Dihydro-4,9-dioxo-5-methoxy-2-phenylnaphtho[2,3-d]thiazole (Example 24)

Yield: 11%; Melting point: 245° C.; Rf: 0.47 (CH$_2$Cl$_2$/ethyl acetate, 98/2); MS (I.E.): m/z 321 (M+.); $^1$H-NMR (CDCl$_3$): δ (ppm); 8.15 (dd, 2H , H-2', H-6', $J_{H2'\text{-}H3'}$=$J_{H5'\text{-}H6'}$=7.98 Hz, $J_{H2'\text{-}H4'}$=$J_{H4'\text{-}H6'}$=1.90 Hz); 7.92 (d, 1H, H-8, $J_{H7\text{-}H8}$=7.60 Hz); 7.73 (t, 1H, H-7, $J_{H7\text{-}H8}$=$J_{H6\text{-}H7}$=8.00 Hz); 7.53 (m, 3H, H-3', H-4', H-5'); 7.39 (d, 1H, H-6, $J_{H6\text{-}H7}$=8.00 Hz); 4.03 (s, 3H, OCH$_3$); $^{13}$C-NMR (CDCl$_3$): δ (ppm); 161.50 (1C, C-5); 135.50 (1C, Cquat); 135.08 (1C, C-7); 132.20 (1C, C-4'); 129.70 (2C, C-3', C-5'); 127.80 (2C, C-2', C-6'); 119.75 (1C, C-6); 119.02 (1C, C-8); 57.00 (1C, OCH$_3$); IR (KBr): ν (cm$^{-1}$); 1678, 1651 (C=O).

EXAMPLES 25 AND 26

4,9-Dihydro-4,9-dioxo-7-methoxy-2-phenylnaphtho[2,3-d]thiazole and 4,9-Dihydro-4,9-dioxo-6-methoxy-2-phenylnaphtho[2,3-d]thiazole To a solution of 9.9 g (41.0 mmol) of nonahydrated sodium sulfide in 27 mL of water, 1.9 g (6.7 mmol) of a (1/1) mixture of 2-amino-3-bromo-6-methoxy-1,4-dihydro-1,4-dioxonaphthalene and 3-amino-2-bromo-6-methoxy-1,4-dihydro-1,4-dioxonaphthalene are added. The reaction mixture is then heated at 50° C. until a blue coloration is obtained; 0.685 mL (6.7 mmol) of benzaldehyde and 2.300 mL of glacial acetic acid are then added successively. After 3 h of heating and complete cooling, the green crystals obtained are filtered, washed with ethanol, and dissolved in 300 mL of chloroform. The organic phase is washed with 100 mL of water, dried over calcium chloride, and evaporated at reduced pressure. 4.0 g of yellow crystals are produced, which are purified on a medium-pressure chromatography column (support: silica 6–35 mm, internal diameter: 3.0 cm, height: 40 cm, pressure: 30 bar, eluant: heptane/dichloromethane, 100/0 to 65/35). The yellow crystals obtained are uncolored and recrystallized in dichloromethane to produce 0.2 g of 4,9-dihydro-4,9-dioxo-7-methoxy-2-phenylnaphtho[2,3-d]thiazole (Example 25) and 1.2 g of 4,9-dihydro-4,9-dioxo-6-methoxy-2-phenylnaphtho[2,3-d]thiazole (Example 26).

4,9-Dihydro-4,9-dioxo-7-methoxy-2-phenylnaphtho[2,3-d]thiazole (Example 25)

Yield: 1.5%; Melting point: >260° C.; Rf: 0.47 (CH$_2$Cl$_2$); MS (I.E.): m/z 321 (M+.); $^1$H-NMR (270 MHZ, CDCl$_3$): δ (ppm); 8.20 (s, 1H, H-8); 8.15 (dd, 2H, H-2', H-6', $J_{H2'\text{-}H3'}$=$J_{H5'\text{-}H6'}$=7.21 Hz, $J_{H2'\text{-}H4'}$=$J_{H4'\text{-}H6'}$=1.93 Hz); 7.78 (d, 1H, H-5, $J_{H5\text{-}H6}$=8.65 Hz); 7.53 (m, 3H, H-3', H-4', H-5'); 7.24 (d, 1H, H-6, $J_{H5\text{-}H6}$=8.65 Hz); 4.01 (s, 3H, OCH$_3$); $^{13}$C-NMR (270 MHZ, CDCl$_3$): δ (ppm); 132.68 (1C, C-5); 129.84 (1C, C-4'); 129.69 (2C, C-3', C-5'); 128.20 (2C, C-2', C-6'); 120.64 (1C, C-6); 111.99 (1C, C-8); 56.58 (OCH$_3$); IR (KBr): ν (cm$^{-1}$); 1679 (C=O).

4,9-Dihydro-4,9-dioxo-6-methoxy-2-phenylnaphtho[2,3-d]thiazole (Example 26)

Yield: 9%; Melting point: 221° C.; Rf: 0.65 (CH$_2$Cl$_2$/ethyl acetate, 98/2); MS (I.E.): m/z 321 (M+.); $^1$H-NMR (270 MHZ, CDCl$_3$): δ (ppm); 8.29 (d, 1H, H-8, $J_{H7\text{-}H8}$=8.65 Hz); 8.14 (d, 2H, H-2', H-6', $J_{H2'\text{-}H3'}$=$J_{H5'\text{-}H6'}$=7.21 Hz); 7.67 (d, 1H, H-5, $J_{H5\text{-}H7}$=2.67 Hz); 7.52 (m, 3H, H-3', H-4', H-5'); 7.25 (dd, 1H, H-7, $J_{H7\text{-}H8}$=8.65 Hz, $J_{H5\text{-}H7}$=2.67 Hz); 4.01 (s, 3H, OCH$_3$); $^{13}$C-NMR (270 MHZ, CDCl$_3$): δ (ppm); 164.21 (1C, C-6) 155.88 (1C, Cquat); 135.87 (1C, Cquat); 132.31 (1C, C-5); 130.30 (1C, C-4'); 129.25 (2C, C-3', C-5'); 127.79 (2C, C-2', C-6'); 127.40 (1C, Cquat); 120.27 (1C, C-7); 110.09 (1C, C-8); 56.05 (OCH$_3$); IR (KBr): ν (cm$^{-1}$); 1667 (C=O).

EXAMPLE 27

4,9-Dihydro-4,9-dioxo-8-hydroxy-2-phenyl-naphtho[2,3-d]thiazole

A suspension of 1.00 g (0.003 mol) of 4,9-dihydro-4,9-dioxo-8-methoxy-2-phenyl-naphtho[2,3-d]-thiazole (Example 23) in 67 mL (1.160 mol) of acetic acid and 67 mL (0.570 mol) of hydrobromic acid is heated to reflux for 5 h 30 min. After cooling to 10° C., the reaction medium is filtered through fritted glass. The precipitate consists of 200 mL of chloroform. The organic phase is washed with a 3% ammonia solution (3×40 mL) and dried over calcium chloride. The yellow solid obtained after evaporation at reduced pressure of the solvent is purified on a medium-pressure column (support: silica 6–35 mm, eluant: toluene/ dichloromethane, 100/0, 50/50, 0/100), then recrystallized 3 times in a toluene/heptane mixture, 50/50, to produce 0.302 g of 4,9-dihydro-4,9-dioxo-8-hydroxy-2-phenyl-naphtho[2,3-d]thiazole.

Yield: 33%; Melting point: 263.5° C.; Rf: 0.51 (heptane/ ethyl acetate, 70/30); MS (I.E.): m/z 307 (M+.); $^1$H-NMR (CDCl$_3$): δ (ppm); 8.08 (dd, 2H, H-2', H-6', $J_{H2'-H3'}$=$J_{H5'-H6'}$=8.4 Hz, $J_{H2'-H4'}$=$J_{H4'-H6'}$=1.4 Hz); 7.81 (dd, 1H, H-5, $J_{H5-H7}$=7.6 Hz, $J_{H5-H6}$=1.4 Hz); 7.67 (t, 1H, H-7); 7.55 (m, 3H, H-3', H-4', H-5'); 7.35 (dd, 1H, H-6, $J_{H6-H7}$=8.4 Hz); $^{13}$C-NMR (CDCl$_3$): δ (ppm); 163.11 (1C, C-8); 136.57 (1C, C-6); 132.53 (1C, C-4'); 129.32 (2C, C-3', C-5'); 127.75 (2C, C-2', C-6'); 125.62 (1C, C-7); 120.17 (1C, C-5); IR (KBr): ν (cm$^{-1}$); 1650 (C=O).

EXAMPLE 28

4,9-Dihydro-4,9-dioxo-2-(1-pyrrolyl)-naphtho-[2,3]-thiazole

To a suspension of 2.30 g (0.01 mol) of 2-amino-4,9-dihydro-4,9-dioxo-naphtho[2,3-d]thiazole in 25 mL of acetic acid, 1.3 mL (0.01 mol) of hot 2,5-dimethoxytetrahydrofuran are added. The reaction mixture is heated to reflux for 2 h. The chestnut brown precipitate obtained is filtered, dissolved in dichloromethane, and washed 3 times with 200 mL of distilled water. The organic phase is dried over calcium chloride, filtered, and evaporated at reduced pressure to produce 1.80 g of a yellow solid, which is purified on a flash column (support: silica 6–35 mm; conditioning: heptane; eluant: dichloromethane/ heptane, 90/10). 0.90 g of 4,9-dihydro-4,9-dioxo-2-(1-pyrrolyl)-naphtho[2,3]-thiazole is obtained in the form of yellow crystals after recrystallization and color removal with animal black.

Yield: 64%; Melting point: >260° C.; Rf: 0.41 (CH$_2$Cl$_2$); MS (I.E.): m/z 280 (M+.); $^1$H-NMR (CDCl$_3$): δ (ppm); 8.29, 8.20 (2dd, 1H, H-5, H-8, $J_{H5-H6}$=8.85 Hz, $J_{H5-H7}$=1.73 Hz); 7.79 (m, 2H, H-6, H-7); 7.48 (m, 2H, H-2', H-5'); 6.42 (m, 2H, H-3', H-4'); $^{13}$C-NMR (CDCl$_3$): δ (ppm); 177.89, 177.47 (2C, C-4, C-9); 165.60 (1C, C-2); 153.00 (1C, C-3a); 137.14 (1C, C-9a); 134.30, 134.06 (2C, C-6, C-7); 132.87, 132.38 (2C, C-4a, C-8a); 127.75, 126.69 (2C, C-5, C-8); 120.52 (2C, C-2', C-5'); 114.23 (2C, C-3', C-4'); IR (KBr): ν (cm$^{-1}$); 1680, 1665 (C=O).

EXAMPLES 29 AND 30

2-(5-Bromofuran-2-yl)-4,9-dihydro-4,9-dioxo-naphtho-[2,3-d]thiazole 2-(4,5-Dibromofuran-2-yl)-4,9-dihydro-4,9-dioxonaphtho[2,3-d]thiazole 10.0 g (35.6 mmol, 1 eq) of 4,9-dihydro-4,9-dioxo-2-(furan-2-yl)naphtho[2,3-d]thiazole are dissolved in 750 mL of dichloromethane that has first been dried on a molecular mesh. The solution is cooled to 0° C., then 11.2 g (81.9 mmol, 2.3 eq) of aluminum chloride are added in small fractions.

The reaction mixture is heated to reflux, 8.0 mL (126.0 mmol, 3.5 eq) of bromine dissolved in 20 mL of dichloromethane are added dropwise, and the reaction is continued for 5 h. The solution is cooled, then gently poured into a saturated solution of sodium hydrogen carbonate. The organic phase is washed several times with water until the pH is neutral, then it is dried over calcium chloride.

10.5 g of solid raw product (chestnut brown-orangish) are obtained after evaporation of the solvent; this is then purified on a flash column (support: silica 6–35 μm; eluant: CH$_2$Cl$_2$/ heptane: 50/50, CH$_2$Cl$_2$: 80/20), to produce, after evaporation, 4.5 g of 2-(5-bromofuran-2-yl)-4,9-dihydro-4,9-dioxo-naphtho[2,3-d]-thiazole in the form of orange crystals and 380 mg of 2-(4,5-dibromofuran-2-yl)-4,9-dihydro-4,9-dioxo-naphtho[2,3-d]thiazole, in the form of yellow crystals.

2-(5-Bromofuran-2-yl)-4,9-dihydro-4,9-dioxo-naphtho-[2,3-d]thiazole

Yield: 42.8%; Melting point: >260° C.; Rf: 0.47 (CH$_2$Cl$_2$); MS (I.E): m/z 359–361 (M$^+$); $^1$H-NMR (CDCl$_3$): δ (ppm); 8.34 (m, 1H, H-5 or H-8); 8.23 (m, 1H, H-5 or H-8); 7.81 (m, 2H, H-6, H-7); 7.40 (d, 1H, H-3', $J_{H3'-H4'}$=3.74 Hz); 6.59 (d, 1H, H-4', $J_{H3'-H4'}$=3.67 Hz); $^{13}$C-NMR (CDCl$_3$): δ (ppm); 178.28, 177.99 (2C, C-4, C-9); 162.67 (C-2); 162.06 (C-2'); 155.35 (C-3a); 149.88 (C-9a); 140.88 (C-5'); 134.58, 134.27 (2C, C-6, C-7); 133.30, 132.83 (2C, C-4a, C-8a); 127.24, 127.13 (2C, C-5, C-8); 115.23, 115.50 (2C, C-3', C-4'); IR (KBr): ν (cm$^{-1}$); 1682 and 1656 (C=O).

2-(4,5-Dibromofuran-2-yl)-4,9-dihydro-4,9-dioxonaphtho[2,3-d]thiazole

Yield: 2.4%; Melting point: >260° C.; Rf: 0.63 (CH$_2$Cl$_2$); MS (APcI−): m/z 438 (M−H) $^1$H-NMR (CDCl$_3$): δ (ppm); 8.35 (m, 1H, H-5 or H-8); 8.24 (m, 1H, H-5 or H-8); 7.82 (m, 2H, H-6, H-7); 7.46 (s, 1H, H-3'); $^{13}$C-NMR (CDCl$_3$): δ ["d" earlier] (ppm); 134.54, 134.25 (2C, C-6, C-7); 127.92, 127.03 (2C, C-5, C-8); 117.59 (1C, C-3'); IR (KBr): ν (cm$^{-1}$); 1685 and 1655 (C=O).

EXAMPLE 31

2-(3-Bromofuran-2-yl)-4,9-dihydro-4,9-dioxo-naphtho-[2,3-d]thiazole

To 150 mL of a solution of sodium hydroxide (pH 10.7), 5.33 g (22.2 mmol, 1 eq) of nonahydrated sodium sulfide are added. The solution is heated at 90° C. and is stirred under an argon atmosphere. 4.61 g (22.2 mmol, 1 eq) of 2-amino-3-chloro-1,4-dihydro-1,4-dioxonaphthalene are added, then the solution is stirred until a blue coloration is obtained. The solution is cooled to 20 and 25° C., then 3.89 g (22.2 mmol) of 3-bromo-2-furaldehyde (CAS No. 14757-78-9) are added to the reaction medium. After 5 min, the argon bubbling is replaced with compressed air for 1 h, then 5 mL of acetic acid are added dropwise; the medium becomes chestnut brown-red.

The stirring is maintained for 5 min, the black precipitate formed is filtered through fritted glass, washed with water, and dried to produce 9.30 g of product, which are purified several times in a flash column (support: silica 6–35 μm; 4.5 cm φ, 30 cm h eluant: dichloromethane/heptane: 50/50).

After evaporation of the solvent, 2.15 g of 2-(3-bromo-2-furan-2-yl)-4,9-dihydro-4,9-dioxo-naphtho-[2,3-d] thiazole are produced in the form of orange crystals.

Yield: 26.9%; Melting point: >250° C.; Rf: 0.30 (CH$_2$Cl$_2$); MS (APcI+): m/z 361 (M$^+$H$^+$); $^1$H-NMR (CDCl$_3$): δ (ppm); 8.36 (m, 1H, H-5 or H-8); 8.25 (m, 1H, H-5 or H-8); 7.82 (m, 2H, H-6, H-7); 7.65 (d, 1H, H-5', $J_{H4'-H5'}$=2.14 Hz); 6.75 (d, 1H, H-4', $J_{H4'-H5'}$=2.14 Hz); $^{13}$C-NMR (DMSO-d$_6$): δ (ppm); 147.95 (1C, C-5'); 134.82, 134.42 (2C, C-6, C-7); 127.24, 126.44 (2C, C-5, C-8); 117.50 (1C, C-4'); IR (KBr): ν (cm$^{-1}$); 1680 and 1655 (C=O).

EXAMPLE 32

2-(4-Bromofuran-2-yl)-4,9-dihydro-4,9-dioxo-naphtho-[2,3-d]thiazole

To 0.257 g (1.24 mmol, 1 eq) of 2-amino-3-chloro-1,4-dihydro-1,4-dioxo-naphtalene in 9 mL of water, 1.19 g (4.96 mmol, 4 eq) of nonahydrated sodium sulfide are added. The mixture is heated to reflux until the coloration of the reaction medium has turned completely blue. 0.26 g (1.48 mmol, 1.19 eq) of 4-bromo-2-furaldehyde is then added to 90° C. The reaction medium is then cooled to ambient temperature before the addition of 0.28 mL of acetic acid. A precipitate then forms. The reaction medium is stirred for 1 h at ambient temperature. The precipitate is filtered, then washed with water. The chestnut brown precipitate (0.35 g) is purified on a flash column (support: alumina; conditioning: dichloromethane/heptane 70/30; eluant: dichloromethane/heptane 70/30, then 80/20, then 100/00; then dichloromethane/methanol 99.6/0.4) to produce 0.145 g of 2-(4-bromofuran-2-yl)-4,9-dihydro-4,9-dioxonaphtho[2,3-d]thiazole in the form of orange crystals.

Yield: 32%; Melting point: >260° C.; Rf: 0.23 (dichloromethane/heptane, proportion 70/30) on an alumina support; MS (IE): m/z 360 (M$^+$)'; $^1$H-NMR (CDCl$_3$): δ (ppm); 8.34 (m, 1H, H-5 or H-8); 8.25 (m, 1H, H-8 or H-5); 7.83 (m, 2H, H-6, H-7); 7.64 (d, 1H, H-5', $J_{H3'-H5'}$=0.95 Hz); 7.46 (d, 1H, H-3', $J_{H3'-H5'}$=0.95 Hz); $^{13}$C-NMR (CDCl$_3$): δ (ppm); 143.76 (1C, C-5'); 134.48, 134.17 (2C, C-6, C-7); 127.89, 126.99 (2C, C-5, C-8); 116.07 (1C, C-3'); IR (KBr): ν (cm$^{-1}$); 1680, 1657 (C=O).

EXAMPLE 33

4,9-Dihydro-4,9-dioxo-2-(5-nitrofuran-2-yl)naphtho-[2,3-d]thiazole

To 5 g (17.8 mmol) of 4,9-dihydro-4,9-dioxo-2-(furan-2-yl)naphtho[2,3-d]thiazole, one adds 20 mL of fuming nitric acid and 20 mL of concentrated sulfuric acid at room temperature. The reaction mixture is heated to reflux for 72 h; the precipitate formed is filtered through fritted glass, washed with water, and rinsed with ether. The dark yellow powder obtained is recrystallized in DMF after color removal with animal black. In this manner, 2 g of 4,9-dihydro-4,9-dioxo-2-(5-nitro-furan-2-yl)naphtho-[2,3-d] thiazole are produced in the form of a dark yellow solid.

Yield: 34%; Melting point: >300° C.; Rf: 0.30 (CH$_2$Cl$_2$); MS (APcI-): m/z 326 (M$^-$); $^1$H-NMR (CDCl$_3$): δ (ppm); 8.39 (m, 1H, H-5 or H-8); 8.27 (m, 1H, H-5 or H-8); 7.85 (m, 2H, H-6, H-7); 7.59 (d, 1H, H-4', $J_{H3'-H4'}$=3.73 Hz); 7.50 (d, 1H, H-3', $J_{H3'-H4'}$=3.74 Hz); IR (KBr): ν (cm$^{-1}$); 1675, 1656 (C=O).

EXAMPLE 34

2-(5-Aminofuran-2-yl)-4,9-dihydro-4,9-dioxo-naphtho-[2,3-d]thiazole

In a three-necked flask, 2 g (6.10 mmol, 1 eq) of 4,9-dihydro-4,9-dioxo-2-(5-nitrofuran-2-yl)-naphtho[2,3-d]-thiazole are dissolved in 1500 mL of absolute ethanol. The setup is placed under an inert atmosphere, and a spatula tip of 30% palladium-type charcoal is added. The solution is heated to reflux and 360 μL (7.36 mmol; 1.2 eq) of hydrazine are added in five aliquots. The reaction is continued for 1 h, with the solution's color changing from yellow-green to black-violet. The solution is cooled and filtered through Celite; 1.65 g of a black solid are obtained after evaporation of the solvent in a rota vapor. This solid is purified on a flash column (support: silica 6–35 μm, eluant gradient: dichloromethane, then dichloromethane/methanol, 98/2), to produce 0.36 g of 2-(5-aminofuran-2-yl)-4,9-dihydro-4,9-dioxo-naphtho[2,3-d]thiazole in the form of blue crystals.

Yield: 20%; Melting point: >260° C.; Rf: 0.29 (Dichloromethane/ethyl acetate, 99/1); MS (APcI+): m/z 297 (M$^+$H$^+$); $^1$H-NMR (DMSO-d$_6$): δ (ppm); 8.24 (m, 1H, H-5 or H-8); 8.18 (m, 1H, H-5 or H-8); 7.99 (m, 2H, H-6, H-7); 7.60 (d, 1H, H-3', $J_{H3'-H4'}$=3.97 Hz); 7.36 (s, 2H, NH$_2$); 5.47 (d, 1H, H-4', $J_{H3'-H4'}$=3.97 Hz); $^{13}$C-NMR (DMSO-d$_6$): δ (ppm); 177.8, 177.2 (2C, C-4, C-9); 161.0 (1C, C-5'); 155.0 (1C, C-2); 138.0 (1C, C-2'); 134.3, 134.1 (2C, C-6, C-7); 133.1, 132.4 (2C, C-4a, C-8a); 127.0, 126.0 (2C, C-5, C-8); 122.1 (1C, C-3'); 87.5 (1C, C-4'); IR (KBr): ν (cm$^{-1}$); 3350 (NH$_2$); 1680 and 1625 (C=O).

EXAMPLE 35

2-(5-Acetamidofuran-2-yl)-4,9-dihydro-4,9-dioxonaphtho[2,3-d]thiazole

In a three-necked bottle, to 0.300 g (1.01 mmol, 1 eq) of 2-(5-aminofuran-2-yl)-4,9-dihydro-4,9-dioxo-naphtho-[2,3-d]-thiazole, one adds, dropwise and at ambient temperature, 200 μL (2.02 mmol; 2 eq) of acetic anhydride, then 60 μL (1.01 mmol; 1 eq) of acetic acid. The suspension obtained is heated at 50° C., and becomes bordeaux red. After 2 h of reaction, the suspension is cooled and dissolved in 500 mL of dichloromethane. The solution is washed two times with a saturated solution of sodium hydrogen carbonate, then several times with water until the aqueous has a neutral pH. After drying the organic phase over calcium chloride and evaporation of the solvents, 0.330 g of solid raw product (bordeaux red) is obtained. This solid is purified on a flash column (support: silica 6–35 μm, eluant: dichloromethane/methanol, 98/2). The compound obtained is dissolved in dichloromethane, then filtered through micropores. The filtrate is concentrated and the precipitate formed is filtered through fritted [glass] to produce 0.145 g of 2-(5-acetamidofuran-2-yl)-4,9-dihydro-4,9-dioxo-naphtho[2,3-d]thiazole in the form of brick-red crystals.

Yield: 42%; Melting point: >260° C.; Rf: 0.34 (Dichloromethane/Methanol, 95/5); MS (APcI+): m/z 339 (M$^+$H$^+$); $^1$H-NMR (DMSO-d$_6$): δ (ppm); 11.75 (s, 1H, NH); 8.28 (m, 1H, H-5 or H-8); 8.23 (m, 1H, H-5 or H-8); 8.03 (m, 2H, H-6, H-7); 7.69 (d, 1H, H-3', $J_{H3'-H4'}$=3.73 Hz); 6.62 (d, 1H, H-4', $J_{H3'-H4'}$=3.74 Hz); 2.22 (s, 3H, CH$_3$); $^{13}$C-NMR (DMSO-d$_6$): δ (ppm) 177.9, 176.5 (2C, C-4, C-9); 167.5 (1C, C-5'); 155.2 (1C, C-2); 139.0 (1C, C-2'); 134.6, 134.4 (2C, C-6, C-7); 132.7, 132.6 (2C, C-4a, C-8a); 127.2, 126.4 (2C, C-5, C-8); 118.1 (1C, C-3'); 97.0 (1C, C-4'); 23.4 (1C, CH$_3$); IR (Kbr): (cm$^1$); 3033 (N–H); 1682 and 1655 (C=O).

EXAMPLE 36

4,9-Dihydro-4,9-dioxo-2-(5-hydroxymethylfuran-2-yl)naphtho[2,3-d]thiazole 17.36 g (72.2 mmol, 5 eq) of nonahydrated sodium sulfide are dissolved in 70 mL of water. The solution is heated at 60° C., then 3.00 g (14.4 mmol, 1 eq) of 2-amino-3-chloro-1,4- dihydro-1,4-dioxo-naphthalene are added. After 30 min of stirring at 60° C., the solution is cooled to ambient temperature. To the reaction medium, which has turned blue, 2.43 g (14.5 mmol, 1 eq) of 5-acetoxymethyl- 2-furaldehyde are added; after 5 min, 3 mL of acetic acid are then added dropwise. The medium turns chestnut brown-orangish; the precipitate formed is filtered through fritted glass, washed with water, and dried to produce 3.30 g of raw product which are purified on a flash column (support: silica 6–35 μm; 5 cm φ, 15 cm h, eluant: $CH_2Cl_2$/MeOH, 96/4). The orange product obtained is recrystallized in dimethylformamide, uncolored on animal black, and filtered through Celite and micropores to produce 0.80 g of 4,9-dihydro-4,9-dioxo-2-(5-hydroxymethylfuran-2-yl)naphtho[2,3-d]thiazole in the form of ocher crystals.

Yield: 17%; Melting point: >260° C.; Rf: 0.60 ($CH_2Cl_2$/MeOH, 96/4); MS (I.E): m/z 311 ($M^+$); $^1$H-NMR (DMSO-$d_6$): δ (ppm); 8.20 (m, 1H, H-5 or H-8); 8.11 (m, 1H, H-5 or H-8); 7.91 (m, 2H, H-6, H-7); 7.46 (d, 1H, H-3', $J_{H3'-H4'}$=3.1 Hz); 6.65 (d, 1H, H-4', $J_{H3'-H4'}$=3.1 Hz); 5.55 (t, 1H, OH, $J_{OH-CH2}$=5.6 Hz); 4.54 (d, 2H, $CH_2$, $J_{CH2-OH}$=5.6 Hz); $^{13}$C-NMR (DMSO-$d_6$): δ (ppm); 177.6, 176.6 (2C, C-4, C-9); 160.0 (1C, C-5'); 158.4 (1C, C-2); 146.6 (1C, C-2'); 134.4 (2C, C-6, C-7); 132.3, 132.1 (2C, C-4a, C-8a); 127.0, 126.2 (2C, C-5, C-8); 127.0, 126.2 (2C, C-5, C-8); 114.9 (1C, C-3'); 110.5 (1C, C-4'); 55.6 (1C, $CH_2$); IR (Kbr): ν ($cm^{-1}$); 3374 (OH), 1677 and 1656 (C=O).

EXAMPLE 37

2-(5-Acetoxymethylfuran-2-yl)-4,9-dihydro-4,9-dioxonaphtho[2,3-d]thiazole

To 5.00 g (24 mmol) of 2-amino-3-mercapto-1,4-dihydro-1,4-dioxonaphthalene, 40 mL of N-methylpyrrolidone are added at 0° C. under an argon atmosphere. The reaction mixture is stirred for 10 min, then 4.10 g (24 mmol) of 5-acetoxymethyl-2-furaldehyde are added at 0° C. After 5 h of stirring at this temperature, the mixture is allowed to return to ambient temperature. The content of the three-necked flask is poured into 250 mL of water, and the chestnut brown precipitate formed is dissolved in ethyl acetate. The organic phase is extracted, dried over magnesium sulfate, filtered, and evaporated at reduced pressure.

The chestnut brown solid obtained is purified a first time in a column (support: silica 6–35 μm; eluant: $CH_2Cl_2$/MeOH/AcOEt, 97/1/2) to produce 3.29 g of product.

A sample of 0.500 g is collected, then purified a second time by preparative plates (support: silica; eluant: $CH_2Cl_2$/MeOH/AcOEt, 97/1/2), to produce 0.107 mg of 2-(5-acetoxymethylfuran-2-yl)-4,9-dihydro-4,9-dioxonaphtho[2,3-d]thiazole in the form of yellow crystals.

Yield: 38%; Melting point: 204° C.; Rf: 0.52 (heptane/AcOEt, 50/50); MS (I.E.): m/z 353($M^+$); $^1$H-NMR ($CDCl_3$): δ (ppm); 8.34 (m, 1H, H-5 or H-8); 8.24 (m, 1H, H-5 or H-8); 7.81 (m, 2H, H-6, H-7); 7.41 (d, 1H, H-3', $J_{H3'-H4'}$32 3.74 Hz); 6.64 (d, 1H, H-4', $J_{H4'-H3'}$=3.32 Hz); 5.15 (s, 2H, $CH_2$); 2.14 (s, 3H, $CH_3$); $^{13}$C-NMR ($CDCl_3$): δ (ppm); 134.39, 134.14 (2C, C-6, C-7); 133.30, 132.83 (2C, C-4a, C-8a); 127.86, 126.94 (2C, C-5, C-8); 114.52, 113.77 (2C, C-3', C-4'); 57.67 (1C, $CH_2$); 20.83 (1C, $CH_3$); IR (KBr): ν ($cm^{-1}$); 1734, 1686 and 1669 (C=O).

EXAMPLE 38

4,9-Dihydro-4,9-dioxo-2-(5-methyl-2-furyl)naphtho-[2,3-d]thiazole

To a buffer solution at pH 11 (containing 6.2 g of $H_3BO_3$ and 4 g of NaOH per liter), 4.6 g (19.3 mmol) of nonahydrated sodium sulfide are added. The mixture is stirred at 15° C. under an argon atmosphere until the dissolution is complete, then 2 g (9.6 mmol) of 2-amino-3-chloro-1,4-dihydro-1,4-dioxonaphthalene are added. After 20 min, 0.96 mL (9.6 mmol) of 5-methyl-2-furfural is added to the reaction medium, which has turned blue.

After 4 h of stirring, the content of the three-necked flask is poured into 100 mL of ethyl acetate and the three-necked flask is rinsed with 50 mL of water. The organic phase is washed three times with 80 mL of water and dried over magnesium sulfate. After evaporation of the solvent at reduced pressure, 1 g of orange product is formed, which is purified over a cake (support: silica 6–35 μm; eluant: $CH_2Cl_2$/heptane: 50/50, 90/10, and 100) to produce 0.560 g of orangish crystals, which are recrystallized in an AcOEt/$CH_2Cl_2$ mixture: 70/30 after color removal with animal charcoal.

Yield: 35%; Melting point: 254° C.; Rf: 0.48 ($CH_2Cl_2$); MS (I.E): m/z 295 ($M^+$); $^1$H-NMR ($CD_2Cl_2$): δ (ppm); 8.22 (dd, 1H, H-5 or H-8, $J_{H5-H6}$ or $J_{H7-H8}$=8.85 Hz, $J_{H5-H7}$ or $J_{H6-H8}$=1.73 Hz); 8.16 (m, 1H, H-5 or H-8); 7.80 (m, 2H, H-6, H-7); 7.28 (d, 1H, H-3', $J_{H3'-H4'}$=3.35 Hz); 6.29 (d, 1H, H-4', $J_{H3'-H4'}$=3.35 Hz); 2.44 (s, 3H, $CH_3$); $^{13}$C-NMR ($CDCl_3$): δ (ppm); 178.43, 178.12 (C-4, C-9); 164.07 (C-2); 157.79 (C-5'); 155.00 (C-3a); 146.92 (C-2'); 140.60 (C-9a); 134.54, 134.32 (C-6, C-7); 133.50, 133.04 (C-4a, C-8a); 127.72, 126.94 (C-5, C-8); 115.43, 110.16 (C-3', C-4'); 14.09 ($CH_3$); IR (KBr): ν ($cm^{-1}$); 1684 and 1653 (C=O).

EXAMPLE 39

4,9-Dihydro-2-(4,5-dimethyl-2-furyl)4,9-dioxonaphtho-[2,3-d]thiazole

To 200 mL of a solution of sodium hydroxide (pH=10.66), 6.94 g (28.9 mmol) of nonahydrated sodium sulfide are added. The mixture is stirred at 15° C. under an argon atmosphere until the dissolution is complete, then 3.00 g (14.4 mmol) of 2-amino-3-chloro-1,4-dihydro-1,4-dioxonaphthalene are added. After 3 h of stirring at ambient temperature, 1.80 g (14.4 mmol) of 4,5-dimethyl-2-furaldehyde are added to the reaction medium, which has turned blue; after 5 min, 5 mL of acetic acid are added dropwise, and the medium turns orangish.

The stirring is continued for 5 min, then the argon bubbling is replaced with compressed air for 3 min.

The black precipitate formed is filtered through fritted glass, washed with water, and dried to produce 4.00 g of product, which are purified in a flash column (support: silica 6–35 μm; eluant: heptane/AcOEt: 85/15).

The orange product obtained after evaporation of the solvent is uncolored with animal charcoal, then recrystallized in ethyl acetate to produce 2.50 g of 4,9-dihydro-2-(4,5-dimethyl-2-furyl)4,9-dioxonaphtho[2,3-d]-thiazole in the form of orange crystals.

Yield: 90%; Melting point: 250° C.; Rf: 0.2 ($CH_2Cl_2$); MS (I.E): m/z 309 ($M^+$); $^1$H-NMR ($CDCl_3$): δ (ppm); 8.31 (dd, 1H, H-5 or H-8, $J_{H5-H6}$ or $J_{H5-H7}$=8.85 Hz, $J_{H5-H7}$ or $J_{H6-H8}$=1.73 Hz); 8.22 (dd, 1H, H-5 or H-8, $J_{H5-H6}$ or $J_{H5-H7}$=8.85 Hz, $J_{H5-H7}$ or $J_{H6-H8}$=1.73 Hz); 7.80 (m, 2H, H-6, H-7); 7.23 (s, 1H, H-3'); 2.35 (s, 3H, $CH_3$ at 5'); 2.17 (s, 3H, $CH_3$ at 4'); $^{13}$-NMR ($CDCl_3$): δ (ppm); 178.43, 178.12 (2C, C-4, C-9); 172 (C-2); 164.21 (C-2'); 155.35 (C-3a); 153.18 (C-5'); 145.32 (C-9a); 134.13, 133.97 (2C, C-6, C-7); 133.24, 132.89 (2C, C-4a, C-8a); 127.72, 126.79 (2C, C-5, C-8); 118.78 (C-4'); 117.51 (C-3'); 12.50 ($CH_3$ at 5'); 10.00 ($CH_3$ at 4'); IR (KBr): ν ($cm^{-1}$); 1682 and 1656 (C=O).

EXAMPLE 40

4,9-Dihydro-4,9-dioxo-2-(5-phenyl-2-oxazolyl) naphtho[2,3-d]thiazole

To 2-amino-3-chloro-1,4-dihydro-1,4-dioxonaphthalene (0.21 g, 1.0 mmol) in distilled water (7 mL), nonahydrated sodium sulfide (0.98 g, 4.1 mmol) is added under an argon atmosphere. The mixture is heated to reflux under an argon atmosphere until the coloration of the reaction medium has become completely blue. 5-phenyl-2-oxazole carbaldehyde [sic; carboxyaldehyde] (CAS No. 96829-89-9) (0.21 g, 1.4 mmol) in solution in tetrahydrofuran (6 mL) is then added as well as acetic acid (0.25 mL). The reaction medium is then stirred under an argon atmosphere at ambient temperature for 1 h. An orange precipitate then forms. The precipitate is then filtered and washed with water. The orange precipitate (0.28 g) is then partially dissolved in diethyl ether (21 mL). After filtration of the insoluble content, the filtrate is concentrated at reduced pressure and chromatographed using a flash column (support: silica 6–35 µm; eluant: dichloromethane/methanol: 98/2). The orange product obtained after evaporation is uncolored with animal charcoal, then filtered through micropores. Orange crystals (0.17 g) of 4,9-dihydro-4,9-dioxo-2-(5-phenyl-2-oxazolyl) naphtho[2,3-d]thiazole are thus obtained after evaporation.

Yield: 79%; Melting point: >260° C.; Rf: 0.64 (acetonitrile in reverse phase); 0.76 (dichloromethane/methanol, 98/2); MS (I.E): m/z 358 (M$^+$)', 330 (M$^+$–CO); $^1$H-NMR (CDCl$_3$): δ (ppm): 8.36 (m, 1H, H-5 or H-8); 8.26 (m, 1H, H-5 or H-8); 7.85 (m, 4H, H-6, H-7, H-2", H-6"); 7.60 (d, 1H, H-4', J=0.9 Hz); 7.55–7.35 (m, 2H, H-3", H-5"); 7.27 (d, 1H, H-4", J=0.9 Hz); $^{13}$C-NMR (CDCl$_3$): δ (ppm): 178.23, 177.36 (2C, C-4 and C-9); 160.34 (1C, C-2); 155.20 (1C, C-2'); 154.60 (1C, C-3a); 154.37 (1C, C-5'); 142.98 (1C, C-9a); 134.71, 134.27 (2C, C-6 and C-7); 133.04, 132.77 (2C, C-4a and C-8a); 129.92 (1C, C-8 or C-5); 129.15 (2C, C-2" and C-6"); 128.02 (1C, C-5 or C-8); 127.16 (1C, C-4'); 126.51 (1C, C-1"); 125.22 (2C, C-3" and C-5"); 124.66 (1C, C-4"); IR (KBr): ν cm$^{-1}$; 1681 and 1654 (C=O), 1589 (N=C—O).

EXAMPLE 41

4,9-Dihydro-4,9-dioxo-2-(2-thiazolyl)naphtho[2,3-d]-thiazole

To 1.12 g (5.39 mmol) of 2-amino-3-chloro-1,4-dihydro-1,4-dioxonaphthalene in 38 mL of water, 5.18 g (21.56 mmol) of nonahydrated sodium sulfide are added. The mixture is heated to reflux until the coloration of the reaction medium has turned completely blue. 0.73 g (6.46 mmol) of 2-thiazole carboxyaldehyde, then 1.3 mL (22.75 mmol) of acetic acid, are added at 90° C. The reaction medium is then immediately cooled to 0° C. using an ice bath. A precipitate then forms. The reaction medium is stirred for 1 h at 0° C. The precipitate is then filtered and washed with water. The precipitate is then partially dissolved in dichloromethane. During the filtration and the solubilization in dichloromethane, a change in color occurs: the chestnut brown precipitate takes on a yellow-brown color. After filtration of the insoluble content and evaporation of the solvent, 0.3 g of 4,9-dihydro-4,9-dioxo-2-(2-thiazolyl) naphtho[2,3-d]thiazole are obtained in the form of yellow-brown crystals.

Yield: 19%; Melting point: >260° C.; Rf: 0.22 (dichloromethane); MS (APcI–): m/z 298 (M$^-$); $^1$H-NMR (CDCl$_3$): δ (ppm): 8.36 (m, 1H, H-5 or H-8); 8.26 (m, 1H, H-8 or H-5); 8.03 (d, 1H, H-4', J$_{H4'-H5'}$=3.06 Hz); 7.84 (m, 2H, H-6, H-7); 7.67 (d, 1H, H-5', J$_{H4'-H5'}$=3.05 Hz); $^{13}$C-NMR (CDCl$_3$): δ (ppm): 145.18 (1C, C-4'); 134.91, 134.53 (2C, C-6, C-7); 128.24, 127.41 (2C, C-8, C-5); 124.59 (1C, C-5'); IR (KBr): ν (cm$^{-1}$); 1675, 1652 (C=O).

EXAMPLES 42 AND 43

4,9-Dihydro-4,9-dioxo-6-fluoro-2-(2-furyl)-naphtho [2,3-d]thiazole and

4,9-Dihydro-4,9-dioxo-7-fluoro-2-(2-furyl)-naphtho-[2,3-d]thiazole

Synthesis Intermediates:

2,3-Dibromo-1,4-dihydro-1,4-dioxo-6-fluoronaphthalene

To a solution of 1,4-dihydro-1,4-dioxo-6-fluoronaphthalene (CAS No. 148541-61-1) (12.5 g, 71 mmol) in chloroform (250 mL), 36 mL (710 mmol) of bromine are added. The solution is heated to reflux for 12 h, then allowed to return to ambient temperature. After bubbling compressed air through it, the solution is concentrated at reduced pressure and the solid obtained is washed 5 times with heptane; 15.0 g of a beige powder of 2,3-dibromo-1,4-dihydro-1,4-dioxo-6-fluoronaphthalene are produced.

Yield: 65%; Melting point: 158° C.; Rf: 0.80 (dichloromethane); MS (APcI–): m/z 332, 334, 336 (M$^-$); $^1$H-NMR (CDCl$_3$): δ (ppm): 8.22 (dd, 1H, H-8, J$_{H7-H8}$=8.55 Hz, J$_{H-F}$=5.19 Hz); 7.81 (dd, 1H, H-5, J$_{H-F}$=8.55 Hz, J$_{H5-H7}$=2.75 Hz); 7.45 (td, 1H, H-7, J$_{H-F}$=J$_{H7-H8}$=8.55 Hz, J$_{H5-H7}$=2.75 Hz); IR (KBr): ν (cm$^{-1}$); 1680 (C=O).

2-Amino-3-bromo-1,4-dihydro-1,4-dioxo-6-fluoronaphthalene and

2-Amino-3-bromo-1,4-dihydro-1,4-dioxo-7-fluoronaphthalene

In a solution of 6-fluoro-2,3-dibromo-1,4-dihydro-1,4-dioxonaphthalene (10.00 g, 30 mmol) in tetrahydrofuran (500 mL), ammonia is bubbled in at ambient temperature for 2 h, then compressed air is passed through the solution for 15 min. After evaporation of the solvent at reduced pressure, the solid obtained is first cleaned over silica gel cake (support: silica 6–35 µm; 5 cm φ; h=15 cm; eluant: dichloromethane/heptane, 90/10) purified by three flash chromatographies on a silica gel column (support: silica 6–35 µm; 5 cm φ; 30 cm h; eluant: dichloromethane/heptane, 90/10). 4.78 g of a red powder, a mixture of 2-amino-3-bromo-6-fluoro-1,4-dihydro-1,4-dioxonaphthalene and 2-amino-3-bromo-7-fluoro-1,4-dihydro-1,4-dioxonaphthalene, are produced.

Yield: 60% (isomer ratio: 75/25); Melting point: 190–195° C.; Rf: 0.40 (dichloromethane); MS (APcI–): m/z 270 (M$^-$); $^1$H-NMR (acetone-d$_6$): δ (ppm); 8.27 (dd, 1H, H-5 or H-8, J$_{H5-H6}$ or J$_{H7-H8}$=8.54 Hz, J$_{H-F}$5.18 Hz); 7.85 (dd, 1H, H-5 or H-8, J$_{H-F}$=8.54 Hz, J$_{H5-H7}$ or J$_{H6-H8}$=2.74 Hz); 7.71 (td, 1H, H-6 or H-7 minority isomer, J$_{H-F}$=J$_{H5-H6}$ or J$_{H7-H8}$=8.54 Hz, J$_{H5-H7}$ or J$_{H6-H8}$=2.74 Hz); 7.64 (td, 1H, H-6 or H-7 majority isomer, J$_{H-F}$=J$_{H5-H6}$ or J$_{H7-H8}$=8.54 Hz, J$_{H5-H7}$ or J$_{H6-H8}$=2.74 Hz); IR (KBr): ν (cm$^{-1}$); 3357 (NH$_2$), 1685 (C=O).

4,9-Dihydro-4,9-dioxo-6-fluoro-2-(2-furyl)naphtho-[2,3-d]thiazole and 4,9-Dihydro-4,9-dioxo-7-fluoro-2-(2-furyl)naphtho-[2,3-d]thiazole To 0.50 g (1.8 mmol; 1.0 eq) of a 75/25 mixture of 2-amino-3-bromo-1,4-dihydro-1,4-dioxo-6- fluoronaphthalene and 2-amino-3-bromo-1,4-dihydro-1,4-dioxo-7-fluoronaphthalene, 25 mL of a sodium hydroxide solution ($5 \times 10^{-4}$M) containing 1.11 g (4.6 mmol; 2.5 eq) of nonahydrated sodium sulfide are added. The red suspension is heated for 30 min at 80° C. until a dark blue solution is obtained; 0.3 mL (3.6 mmol; 2.0 eq) of 2-furaldehyde is then added. After 90 min of heating at 80° C., the dark red solution obtained is allowed to return to ambient temperature. A few drops of glacial acetic acid are then added, then the orange precipitate formed is filtered, washed three times with water, and dried; 0.5 g of a mixture of two isomers of 4,9-dihydro-4,9-dioxo-6-fluoro-2-(2-furyl)naphtho[2,3-d]thiazole and 4,9-dihydro-4,9-dioxo-7-fluoro-2-(2-furyl)naphtho[2,3-d]-thiazole in the form of red crystals is obtained.

The isomers are separated by flash chromatography on a silica gel column (silica 6–35 μm; 4.5 cm φ; 30 cm h; eluant: dichloromethane), then by preparative HPLC (column: Dynamax 60-A Si 83–141C; eluant: heptane/ethyl acetate: 80/20) to produce 0.125 g of the less polar product and 0.375 g of the more polar product.

Yield: 90% (isomer ratio: 75/25).
The Less Polar Product

Melting point: >265° C.; Rf: 0.32 (heptane/ethyl acetate, 80/20); MS (APcI-): m/z 299 (M$^-$); $^1$H-NMR (CD$_2$Cl$_2$): δ (ppm); 8.17 (dd, 1H, H-5 or H-8, $J_{H5-H6}$ or $J_{H7-H8}$=8.55 Hz, $J_{H-F}$=5.50 Hz); 7.85 (dd, 1H, H-5 or H-8, $J_{H-F}$=8.55 Hz, $J_{H5-H7}$ or $J_{H6-H8}$=2.44 Hz); 7.61 (m, 1H, H-5'); 7.13 (td, 1H, H-6 or H-7, $J_{H5-H6}$ or $J_{H7-H8}$=$J_{H-F}$=8.55 Hz, $J_{H5-H7}$ or $J_{H6-H8}$=2.44 Hz); 7.33 (d, 1H, H-3', $J_{H3'-H4'}$=3.66 Hz); 6.61 (dd, 1H, H-4', $J_{H3'-H4'}$=3.66 Hz, $J_{H4'-H5'}$=1.83 Hz); IR (KBr): ν (cm$^{-1}$); 1680 and 1655 (C=O).
The More Polar Product Melting point: >265° C.; Rf: 0.25 (heptane/diethyl acetate, 80/20); MS (APcI-): m/z 299 (M$^-$); $^1$H-NMR (CD$_2$Cl$_2$): δ (ppm); 8.23 (dd, 1H, H-5 or H-8, $J_{H5-H6}$ or $J_{H7-H8}$=8.54 Hz, $J_{H-F}$=5.50 Hz); 7.78 (dd, 1H, H-5 or H-8, $J_{H-F}$=8.54 Hz, $J_{H5-H7}$ or $J_{H6-H8}$=2.75 Hz); 7.61 (m, 1H, H-5'); 7.40 (td, 1H, H-6 or H-7, $J_{H5-H6}$ or $J_{H7-H8}$=$J_{H-F}$=8.55 Hz, $J_{H5-H7}$ or $J_{H6-H8}$=2.75 Hz); 7.33 (d, 1H, H-3', $J_{H3'-H4'}$=3.66 Hz); 6.60 (dd, 1H, H-4', $J_{H3'-H4'}$=3.66 Hz, $J_{H4'-H5'}$=1.83 Hz); IR (KBr): ν (cm$^{-1}$); 1680 and 1660 (C=O).

EXAMPLES 44 AND 45

4,9-Dihydro-4,9-dioxo-6-fluoro-2-phenylnaphtho[2,3-d]thiazole and 4,9-Dihydro-4,9-dioxo-7-fluoro-2-phenylnaphtho[2,3-d]thiazole To 0.80 g (2.96 mmol; 1.0 eq) of a 75/25 mixture of 2-amino-3-bromo-1,4-dihydro-1,4-dioxo-6-fluoronaphthalene and 2-amino-3-bromo-1,4-dihydro-1,4-dioxo-7-fluoronaphthalene, 40 mL of an aqueous solution of nonahydrated sodium sulfide are added (1.78 g; 7.40 mmol; 2.5 eq). The red suspension is heated for 0.5 h at 80° C. until a dark blue solution is obtained; 0.6 mL (5.90 mmol; 2.0 eq) of benzaldehyde is then added, and the solution is stirred for an additional 2 h at 80° C. The chestnut brown solution obtained is allowed to return to ambient temperature, then a few drops of glacial acetic acid are added. The dark green precipitate formed is filtered, washed three times with water, and dried; 0.820 g of a mixture of 4,9-dihydro-4,9-dioxo-6-fluoro-2-phenylnaphtho-[2,3-d]thiazole and 4,9-dihydro-4,9-dioxo-7-fluoro-2-phenylnaphtho[2,3-d]thiazole in the form of yellow crystals is obtained.

The isomers are separated by three successive flash chromatographies on a silica gel column (support: silica 6–35 μm; 9.5 cm φ; 25 cm h; eluant: dichloromethane/heptane, 70/30) to produce a 0.205 g of the less polar product and 0.615 g of the more polar product.

Yield: 89% (isomer yield: 75/25);
Less Polar Product

Melting point: 261° C.; Rf: 0.48 (dichloromethane/heptane: 80/20); MS (APcI-): m/z 309 (M$^-$); $^1$H-NMR (CD$_2$Cl$_2$): δ (ppm); 8.20 (dd, 1H, H-5 or H-8, $J_{H5-H6}$ or $J_{H7-H8}$=8.54 Hz, $J_{H-F}$=5.18 Hz); 8.09 (m, 2H, H-2' and H-6'); 7.90 (dd, 1H, H-5 or H-8, $J_{H-F}$=8.54 Hz, $J_{H5-H7}$ or $J_{H6-H8}$=2.74 Hz); 7.50 (m, 4H, H-6 or H-7, H-3', H-4' and H-5'); IR (KBr): ν (cm$^{-1}$); 1680 and 1660 (C=O).
The More Polar Product Melting point: 241° C.; Rf: 0.41 (dichloromethane/heptane: 80/20); MS (APcI-): m/z 309 (M$^-$); $^1$H-NMR (CD$_2$Cl$_2$): δ (ppm); 8.28 (dd, 1H, H-5 or H-8, $J_{H5-H6}$ or $J_{H7-H8}$=8.54 Hz, $J_{H-F}$=5.19 Hz); 8.08 (dd, 2H, H-2' and H-6', $J_{H2'-H3'}$=$J_{H5'-H6'}$=8.05 Hz, $J_{H4'-H6'}$=$J_{H2'-H4'}$=1.65 Hz); 7.81 (dd, 1H, H-5 or H-8, $J_{H-F}$=8.54 Hz, $J_{H5-H7}$ or $J_{H6-H8}$=2.44 Hz); 7.50 (m, 4H, H-6 or H-7, H-3' and H-4' and H-5'); IR (KBr): ν (cm$^{-1}$); 1680 and 1660 (C=O).

EXAMPLES 46 AND 47

4,9-Dihydro-4,9-dioxo-6-fluoro-2-(5-methyl-2-furyl)naphtho[2,3-d]thiazole and 4,9-Dihydro-4,9-dioxo-7-fluoro-2-(5-methyl-2-furyl)naphtho[2,3-d]thiazole To 0.80 g (2.96 mmol; 1.0 eq) of a 75/25 mixture of 2-amino-3-bromo-1,4-dihydro-1,4-dioxo-6-fluoronaphthalene and 2-amino-3-bromo-1,4-dihydro-1,4-dioxo-7-fluoronaphthalene, 40 mL of an aqueous solution of nonahydrated sodium sulfide (1.78 g; 7.40 mmol; 2.5 eq) are added. The red suspension is heated for 30 min at 80° C. until a dark blue solution is obtained; 0.59 mL (5.90 mmol; 2.0 eq) of 5-methyl-2-furaldehyde are then added, and the solution is stirred for an additional 90 min at 80° C. The dark brown solution obtained is allowed to return to ambient temperature, then a few drops of glacial acetic acid are added. The greenish precipitate formed is filtered, washed three times with water, and dried; 0.705 g of a mixture of 4,9-dihydro-4,9-dioxo-6-fluoro-2-(5-methyl-2-furyl)naphtho[2,3-d]thiazole and 4,9-dihydro-4,9-dioxo-7-fluoro-2-(5-methyl-2-furyl)naphtho-[2,3-d]thiazole in the form of dark red crystals is obtained.

The isomers are separated by three successive flash chromatographies on a silica gel column (support: silica 6–35 μm; 5 cm φ; 35 cm h; eluant: dichloromethane/heptane, 90/10) to produce 0.177 g of the less polar product and 0.528 g of the more polar product.

Yield: 76% (isomer ratio: 75/25);
The Less Polar Product

Melting point: 260° C.; Rf: 0.40 (dichloromethane/heptane: 80/20); MS (APcI-): m/z 313 (M$^-$); $^1$H-NMR (CD$_2$Cl$_2$): δ (ppm); 8.18 (dd, 1H, H-5 or H-8, $J_{H5-H6}$ or $J_{H7-H8}$=8.54 Hz, $J_{H-F}$=5.18 Hz); 7.86 (dd, 1H, H-5 or H-8, $J_{H-F}$=8.54 Hz, $J_{H5-H7}$ or $J_{H6-H8}$=2.75 Hz); 7.41 (td, 1H, H-6 or H-7, $J_{H-F}$=$J_{H5-H6}$ or $J_{H7-H8}$=8.54 Hz, $J_{H5-H7}$ or $J_{H6-H8}$=2.75 Hz); 7.25 (d, 1H, H-3', $J_{H3'-H4'}$=3.36 Hz); 6.24 (d, 1H, H-4', $J_{H3'-H4'}$=3.36 Hz); 2.39 (s, 3H, CH$_3$); IR (KBr): ν (cm$^{-1}$); 1685 and 1650 (C=O).
The More Polar Product Melting point: 238° C.; Rf: 0.30 (dichloromethane/heptane, 80/20); MS (APcI-): m/z 313 (M$^-$); $^1$H-NMR (CD$_2$Cl$_2$): δ (ppm); 8.25 (dd, 1H, H-5 or H-8, $J_{H5-H6}$ or $J_{H7-H8}$=8.54 Hz, $J_{H-F}$=5.18 Hz); 7.80 (dd, 1H, H-5 or H-8, $J_{H-F}$=8.54 Hz, $J_{H5-H7}$ or $J_{H6-H8}$=2.75 Hz); 7.42 (td, 1H, H-6 or H-7, $J_{H5-H6}$ or $J_{H7-H8}$=$J_{H-F}$=8.54 Hz, $J_{H5-H7}$ or $J_{H6-H8}$= 2.75 Hz); 7.25 (d, 1H, H-3', $J_{H3'-H4'}$=3.36 Hz); 6.24 (d, 1H, H-4', $J_{H3'-H4'}$=3.36 Hz); 2.39 (s, 3H, CH$_3$); IR (KBr): ν (cm$^{-1}$); 1675 and 1655 (C=O).

EXAMPLES 48 AND 49

4,9-Dihydro-4,9-dioxo-6-fluoro-2-(4-fluorophenyl) naphtho[2,3-d]thiazole and 4,9-Dihydro-4,9-dioxo-7-fluoro-2-(4-fluorophenyl) naphtho[2,3-d]thiazole To 0.80 g (2.96 mmol; 1.0) eq) of a 75/25 mixture of 2-amino-3-bromo-1,4-dihydro-1,4-dioxo-6-fluoronaphthalene and 2-amino-3-bromo-1,4-dihydro-1,4-dioxo-7-fluoronaphthalene, 40 mL of an aqueous solution of nonahydrated sodium sulfide (1.78 g; 7.40 mmol; 2.5 eq) are added. The red suspension is heated for 30 min at 80° C. until a dark blue solution is obtained; 0.63 mL (5.80 mmol; 2.0 eq) of 4-fluorobenzaldehyde is then added, and the solution is stirred for an additional 90 min at 80° C. The dark brown solution obtained is allowed to return to ambient temperature, then a few drops of glacial acetic acid are added. The greenish precipitate formed is filtered, washed three times with water, and dried; 0.570 g of a mixture of 4,9-dihydro-4,9-dioxo-6-fluoro-2-(4-fluorophenyl)naphtho [2,3-d]thiazole and 4,9-dihydro-4,9-dioxo-7-fluoro-2-(4-fluorophenyl)naphtho[2,3-d]thiazole in the form of bright yellow crystals is obtained.

The isomers are separated by three successive flash chromatographies on a silica gel column (support: silica 6–35 μm; 5.5 cm φ; 40 cm h; eluant: dichloromethane/heptane, 80/20), and then each fraction is washed several times with heptane to produce 0.143 g of the less polar product and 0.427 g of the more polar product.

Yield: 59% (isomer ratio: 75/25).
Less Polar Product
Melting point: >265° C.; Rf: 0.42 (dichloromethane/ heptane, 80/20); MS (APcI-): m/z 327 (M$^-$); $^1$H-NMR (CD$_2$Cl$_2$): δ (ppm); 8.21 (dd, 1H, H-5 or H-8, $J_{H5-H6}$ or $J_{H7-H8}$=8.54 Hz, $J_{H-F}$=5.19 Hz); 8.10 (dd, 2H, H-2' and H-6', $J_{H2'-H3'}$=$J_{H5'-H6'}$=8.85 Hz, $J_{H2'-F}$=$J_{H6'-F}$=5.19 Hz); 7.89 (dd, 1H, H-5 or H-8, $J_{H-F}$=8.54 Hz, $J_{H5-H7}$ or $J_{H6-H8}$=2.75 Hz); (td, 1H, H-6 or H-7, $J_{H-F}$=$J_{H5-H6}$ or $J_{H7-H8}$=8.54 Hz, $J_{H5-H7}$ or $J_{H6-H8}$=2.75 Hz); 7.20 (t, 2H, H-3' and H-5', $J_{H-F}$=$J_{H2'-H3'}$=$J_{H5'-H6'}$=8.85 Hz); IR (KBr): ν (cm$^{-1}$); 1675 and 1655 (C=O).
The More Polar Product
Melting point: >265° C.; Rf: 0.40 (dichloromethane/ heptane, 80/20); MS (APcI-): m/z 327 (M$^-$); $^1$H-NMR (CD$_2$Cl$_2$): δ (ppm); 8.28 (dd, 1H, H-5 or H-8, $J_{H5-H6}$ or $J_{H7-H8}$=8.54 Hz, $J_{H-F}$=5.19 Hz); 8.11 (dd, 2H, H-2' and H-6', $J_{H2'-H3'}$=$J_{H5'-H6'}$=8.85 Hz, $J_{H2'-F}$=$J_{H6'-F}$=5.19 Hz); 7.81 (dd, 1H, H-5 or H-8, $J_{H-F}$=8.54 Hz, $J_{H5-H7}$ or $J_{H6-H8}$=2.75 Hz); 7.45 (td, 1H, H-6 or H-7, $J_{H-F}$=$J_{H5-H6}$ or $J_{H7-H8}$=8.54 Hz, $J_{H5-H7}$ or $J_{H6-H8}$=2.75 Hz); 7.20 (t, 2H, H-3' and H-5', $J_{H-F}$=$J_{H2'-H3'}$=$J_{H5'-H6'}$=8.85 Hz); IR (KBr): ν (cm$^{-1}$); 1675 and 1660 (C=O).

EXAMPLES 50 AND 51

4,9-Dihydro-4,9-dioxo-6-fluoro-2-(4-methylphenyl) naphtho[2,3-d]thiazole and 4,9-Dihydro-4,9-dioxo-7-fluoro-2-(4-methylphenyl) naphtho[2,3-d]thiazole To 1 g (3.70 mmol; 1.0 eq) of a 75/25 mixture of 2-amino-3-bromo-1,4-dihydro-1,4-dioxo-6-fluoronaphthalene and 2-amino-3-bromo-1,4-dihydro-1,4-dioxo-7-fluoronaphthalene, 50 mL of an aqueous solution of nonahydrated sodium sulfide (2.22 g; 9.20 mmol; 2.5 eq) are added. The red suspension is heated for 30 min at 80° C. until a dark blue solution is obtained; 0.87 mL (7.40 mmol; 2.0 eq) of 4-methylbenzaldehyde is then added, and the solution is stirred for an additional 90 min at 80° C. The dark brown solution obtained is allowed to return to ambient temperature, then a few drops of glacial acetic acid are added. The greenish precipitate that forms is filtered, washed three times with water, and dried; 0.623 g of a mixture of 4,9-dihydro-4,9-dioxo-6-fluoro-2-(4-methylphenyl)naphtho [2,3-d]thiazole and 4,9-dihydro-4,9-dioxo-7-fluoro-2-(4-methylphenyl)naphtho[2,3-d]thiazole is added in the form of yellow crystals.

The isomers are separated by flash chromatography on a silica gel column (support: silica 6–35 μm; 9 cm φ; 35 cm h; eluant: dichloromethane/heptane, 70/30). The combined fractions are concentrated at reduced pressure, and the solid product formed is washed over fritted glass two times with a minimum amount of methanal and five times with heptane to produce 0.467 g of the more polar product and 0.156 g of the less polar product in the form of yellow crystals.

Yield: 52% (isomer ratio: 75/25).
The More Polar Product
Melting point: >260° C.; Rf: 0.42 (dichloromethane/ heptane: 70/30); MS (APcI-): m/z 323 (M$^-$); $^1$H-NMR (CD$_2$Cl$_2$): δ (ppm); 8.27 (dd, 1H, H-5 or H-8, $J_{H5-H6}$ or $J_{H7-H8}$=8.54 Hz, $J_{H-F}$=5.19 Hz); 7.96 (d, 2H, H-2' and H-6', $J_{H2'-H3'}$=$J_{H5'-H6'}$=8.24 Hz); 7.80 (dd, 1H, H-5 or H-8, $J_{H-F}$=8.54 Hz, $J_{H5-H7}$ or $J_{H6-H8}$=2.75 Hz); 7.44 (td, 1H, H-6 or H-7, $J_{H-F}$=$J_{H5-H6}$ or $J_{H7-H8}$=8.54 Hz, $J_{H5-H7}$ or $J_{H6-H8}$=2.75 Hz); 7.30 (d, 2H, H-3' and H-5', $J_{H2'-H3'}$=$J_{H5'-H6'}$=8.24 Hz); 2.38 (s, 3H, CH$_3$); IR (KBr) ν (cm$^{-1}$); 1670 and 1665 (C=O).
The More Polar Product
Melting point: >260° C.; Rf: 0.46 (dichloromethane/ heptane: 70/30); MS (APcI-): m/z 323 (M$^-$); $^1$H-NMR (CD$_2$Cl$_2$): δ (ppm); 8.20 (dd, 1H, H-5 or H-8, $J_{H5-H6}$ or $J_{H7-H8}$=8.54 Hz, $J_{H-F}$=5.19 Hz); 7.97 (d, 2H, H-2' and H-6', $J_{H2'-H3'}$=$J_{H5'-H6'}$=8.24 Hz); 7.88 (dd, 1H, H-5 or H-8, $J_{H-F}$=8.85 Hz, $J_{H5-H7}$ or $J_{H6-H8}$=2.75 Hz); 7.42 (td, 1H, H-6 or H-7, $J_{H-F}$=$J_{H5-H6}$ or $J_{H7-H8}$=8.54 Hz, $J_{H5-H7}$ or $J_{H6-H8}$=2.75 Hz); 7.31 (d, 2H, H-3' and H-5', $J_{H2'-H3'}$=$J_{H5'-H6'}$=8.24 Hz); 2.39 (s, 3H, CH$_3$); IR (KBr) ν (cm$^{-1}$); 1675 and 1655 (C=O).

EXAMPLES 52 AND 53

4,9-Dihydro-4,9-dioxo-5-fluoro-2-(2-furyl)naphtho- [2,3-d]thiazole 4,9-Dihydro-4,9-dioxo-8-fluoro-2-(2-furyl)naphtho- [2,3-d]thiazole Synthesis Intermediates:
2,3-Dibromo-1,4-dihydro-1,4-dioxo-5-fluoronaphthalene
To a solution of 1,4-dihydro-1,4-dioxo-5-fluoronaphthalene (CAS No. 62784-46-7) 2.45 g (71 mmol) in chloroform (60 mL), 7.34 mL (143 mmol) of bromine are added. The solution is heated to reflux for 12 h, then allowed to return to ambient temperature. After bubbling in compressed air, the solution is concentrated at reduced pressure, and the solid beige product obtained is purified on a flash column (support: silica; conditioning: heptane; eluant: CH$_2$Cl$_2$/heptane) to produce 3.44 g of 2,3-dibromo-1,4-dihydro-1,4-dioxo-5-fluoronaphthalene in the form of beige crystals.

Yield: 74%; Melting point: 100° C.; Rf: 0.63 (dichloromethane/heptane: 80/20); MS (I.E.): m/z 333, 335, 337 (M$^+$+1); $^1$H-NMR (CDCl$_3$): δ (ppm); 8.01 (d, 1H, H-8, $J_{H7-H8}$=7.94 Hz); 7.77 (m, 1H, H-7); 7.52 (m, 1H, H-6); IR (KBr): ν (cm$^{-1}$); 1704 (C=O).

2-Amino-3-bromo-1,4-dihydro-1,4-dioxo-5-fluoronaphthalene

2-Amino-3-bromo-1,4-dihydro-1,4-dioxo-8-fluoronaphthalene

In a solution of 2,3-dibromo-1,4-dihydro-1,4-dioxo-5-fluoronaphthalene (33 mg; 0.098 mmol) in tetrahydrofuran (5 mL), ammonia is bubbled in at ambient temperature for 1 h, then compressed air is passed through the solution for 15 min to eliminate the excess ammonia. After the evaporation of the solvent at reduced pressure, the solid red product obtained is purified on a preparative plate made of silica (eluant: CH$_2$Cl$_2$/heptane=90/10). 20.5 mg of a red powder, a mixture of 2-amino-3-bromo-1,4-dihydro-1,4-dioxo-5-fluoronaphthalene and 2-amino-3-bromo-1,4-dihydro-1,4-dioxo-8-fluoronaphthalene, are obtained.

Yield: 77%; Melting point: 208° C.; Rf: 0.44 (dichloromethane); MS (APcI–): m/z 269, 271 (M$^-$); $^1$H-NMR (CDCl$_3$): δ (ppm); 7.98 (d, 1H, H-5 or H-8, $J_{H5-H6}$ or $J_{H7-H8}$=7.63 Hz); 7.64 (m, 1H, H-6 or H-7); 7.31 (dd, 1H, H-6 or H-7, $J_{H5-H6}$ or $J_{H7-H8}$=$J_{H-F}$=8.55 Hz); 6.40–5.00 (sl, 2H, NH$_2$); IR (KBr): ν (cm$^{-1}$); 3466, 3355 (NH$_2$), 1778, 1633 (C=O).

4,9-Dihydro-4,9-dioxo-5-fluoro-2-(2-furyl)naphtho-[2,3-d]thiazole 4,9-Dihydro-4,9-dioxo-8-fluoro-2-(2-furyl)naphtho-[2,3-d]thiazole To 0.15 g (0.55 mmol; 1.0 eq) of a mixture of 2-amino-3-bromo-1,4-dihydro-1,4-dioxo-5-fluoronaphthalene and 2-amino-3-bromo-1,4-dihydro-1,4-dioxo-8-fluoronaphthalene in 25 mL of water, 0.33 g (1.38 mmol; 2.5 eq) of nonahydrated sodium sulfide is added. The red suspension is heated for 30 min at 80° C. until a dark blue solution is obtained; 0.1 mL (1.1 mmol; 2.0 eq) of 2-furaldehyde is added. After 90 min of heating at 80° C., the dark brown solution obtained is allowed to return to ambient temperature. A few drops of glacial acetic acid are added; then the chestnut brown precipitate form is filtered, washed three times with water, and dried. The mixture of products obtained is purified by preparative thin-layer chromatography (silica 2 mm; eluant: dichloromethane/heptane/ ethyl acetate, 80/10/10), then the two isomers of the expected compound are separated by preparative thin-layer chromatography (silica 2 mm; eluant: dichloromethane) to produce 0.020 g of a mixture of 4,9-dihydro-4,9-dioxo-5-fluoro-2-(2-furyl)naphtho[2,3-d]thiazole and 4,9-dihydro-4, 9-dioxo-8-fluoro-2-(2-furyl)naphtho[2,3-d]thiazole in the form of orange crystals.

Yield: 12% (isomer ratio 47/53).
The Less Polar Isomer

Melting point: >260° C.; Rf: 0.34 (dichloromethane); MS (APcI+): m/z 300 (M$^+$H$^+$); $^1$H-NMR (CD$_2$Cl$_2$): δ (ppm); 8.09 (dd, 1H, H-5 or H-8, $J_{H5-H6}$ or $J_{H7-H8}$=8.24 Hz, $J_{H5-H7}$ or $J_{H6-H8}$=1.22 Hz); 7.75 (td, 1H, H-6 or H-7, $J_{H5-H6}$ or $J_{H7-H8}$=$J_{H6-H7}$=7.94 Hz, $J_{H-F}$=4.58 Hz); 7.65 (dd, 1H, H-5', $J_{H3'-H5'}$=0.92 Hz, $J_{H4'-H5'}$=1.84 Hz); 7.46 (ddd, 1H, H-6 or H-7, $J_{H-F}$=10.98 Hz, $J_{H6-H7}$=8.24 Hz, $J_{H5-H7}$ or $J_{H6-H8}$=1.22 Hz); 7.35 (d, 1H, H-3', $J_{H3'-H4'}$=3.67 Hz); 6.63 (dd, 1H, H-4', $J_{H3'-H4'}$=3.67 Hz, $J_{H4'-H5'}$=1.84 Hz); IR (KBr): ν (cm$^{-1}$); 1680 and 1655 (C=O).
The More Polar Isomer Melting point: >260° C.; Rf: 0.28 (dichloromethane); MS (APcI+): m/z 300 (M$^+$H $^+$); $^1$H-NMR (CD$_2$Cl$_2$): δ (ppm); 8.02 (dd, 1H, H-5 or H-8, $J_{H5-H6}$ or $J_{H7-H8}$=7.63 Hz, $J_{H5-H7}$ or $J_{H6-H8}$=1.22 Hz); 7.73 (td, 1H, H-6 or H-7, $J_{H5-H6}$ or $J_{H7-H8}$=$J_{H6-H7}$=8.24 Hz, $J_{H-F}$=4.58 Hz); 7.64 (dd, 1H, H-5', $J_{H3'-H5'}$=0.91 Hz, $J_{H4'-H5'}$=1.83 Hz); 7.46 (ddd, 1H, H-6 or H-7, $J_{H-F}$=11.29 Hz, $J_{H5-H6}$ or $J_{H7-H8}$=8.54 Hz, $J_{H5-H7}$ or $J_{H6-H8}$=1.22 Hz); 7.37 (d, 1H, H-3', $J_{H3'-H4'}$=3.66 Hz); 6.64 (dd, 1H, H-4', $J_{H3'-H4'}$=3.66 Hz, $J_{H4'-H5'}$=1.83 Hz); IR (KBr): ν (cm$^{-1}$); 1680 and 1655 (C=O).

EXAMPLES 54 AND 55

6-Chloro-4,9-dihydro-4,9-dioxo-2-(2-furyl)-naphtho-[2,3-d]thiazole

7-Chloro-4,9-dihydro-4,9-dioxo-2-(2-furyl)-naphtho-[2,3-d]thiazole

To 435 mg (1.79 mmol) of a mixture of 2-amino-3,6-dichloro-1,4-dihydro-1,4-dioxonaphthalene and 2-amino-3, 7-dichloro-1,4-dihydro-1,4-dioxonaphthalene, one adds, at ambient temperature and under argon, 1.72 g (7.16 mmol) of nonahydrated sodium sulfide in a solution in 15 mL of sodium carbonate, pH 10.6. After 30 min at 60° C. and under argon, 296 mL (3.58 mmol) of 2-furaldehyde are added to the reaction medium, which has turned completely blue. After 15 min of reflux, the argon introduction is eliminated, and the reaction mixture is diluted with 250 mL of water and extracted 3 times with 150 mL of dichloromethane. The organic phase is then washed with 300 mL of water and evaporated to dryness to produce 450 mg of the mixture of 6-chloro-4,9-dihydro-4,9-dioxo-2-(2-furyl)-naphtho[2,3-d] thiazole and 7-chloro-4,9-dihydro-4,9-dioxo-2-(2-furyl)-naphtho[2,3-d]thiazole in the form of orange crystals.

The two isomers are separated on silica cake (silica 40–60 mm, diameter 7 cm, height 14 cm, eluant: dichloromethane/ heptane, 90/10); 80 mg of the less polar product and 150 mg of the more polar product are obtained.
The Less Polar Product Yield: 40% Melting point: >260° C. Rf: 0.42 (CH$_2$Cl$_2$/MeOH, 99/1); MS (APcI–): m/z 315 and 317 (M$^-$); $^1$H-NMR (CDCl$_3$): δ (ppm); 8.28 (d 1H, H-5 or H-8, $J_{H5-H7}$ or $J_{H6-H8}$=2.08 Hz); 8.17 (d, 1H, H-5 or H-8, $J_{H7-H8}$ or $J_{H5-H6}$=8.31 Hz); 7.75 (dd, 1H, H-6 or H-7, $J_{H7-H8}$ or $J_{H5-H6}$=8.31 Hz, $J_{H5-H7}$ or $J_{H6-H8}$=2.07 Hz); 7.65 (m, 1H, H-5'); 7.46 (d, 1H, H-3', $J_{H3'-H4'}$=3.74 Hz); 6.66 (dd, 1H, H-4', $J_{H3'-H4'}$=3.74 Hz, $J_{H3'-H5'}$=1.66 Hz); $^{13}$C-NMR (CDCl$_3$): δ (ppm); 146.81 (C-5'); 134.72 (C-6 or C-7); 129.31, 128.53 (2C, C-5, C-8); 114.75 and 114.11 (2C, C-3', C-4'); IR (KBr): ν (cm$^{-1}$); 1675, 1665 (C=O).
The More Polar Product Yield: 26%; Melting point: >260° C.; Rf: 0.36 (CH$_2$Cl$_2$/MeOH, 99/1); MS (APcI+): m/z 316 and 318 (M$^+$H$^+$); $^1$H-NMR (CDCl$_3$): δ (ppm); 8.28 (d 1H, H-5 or H-8, $J_{H7-H8}$ or $J_{H5-H6}$=8 Hz); 8.18 (d, 1H, H-5 or H-8, $J_{H5-H7}$ or $J_{H6-H8}$=1.84 Hz); 7.77 (dd, 1H, H-6 or H-7, $J_{H7-H8}$ or $J_{H5-H6}$=8.04 Hz, $J_{H5-H7}$ or $J_{H6-H8}$=1.84 Hz); 7.67 (ls, 1H, H-5'); 7.47 (d, 1H, H-3', $J_{H3'-H4'}$=3.45 Hz); 6.66 (m, 1H, H-4'); $^{13}$C-NMR (CDCl$_3$): δ (ppm); 178.50, 177.90 (2C, C-4, C-9); 148.5 (C-2'); 146.8 (C-5'); 141.8 (C-6 or C-7); 134.9 (C-6 or C-7); 131.8 (2C, C-4a, C-8a); 130.09, 127.64 (2C, C-5, C-8); 114.80 (C-3'); 114.11 (C-4'); IR (KBr): ν (cm$^{-1}$); 1675, 1650 (C=O).

EXAMPLE 56

4,9-Dihydro-4,9-dioxo-2-(2-furyl)-5-methoxynaphtho-[2,3-d]thiazole or 4,9-Dihydro-4,9-dioxo-2-(2-furyl)-8-methoxynaphtho-[2,3-d]thiazole Under an inert atmosphere, to 3.64 g (12.9 mmol) of a mixture of 2-amino-3-bromo-1,4-dihydro-1,4-dioxo-5- methoxynaphthalene and 2-amino-3-bromo-1,4-dihydro-1,4-dioxo-8-methoxynaphthalene, 140 mL of an aqueous solution containing 7.74 g (32.2 mmol) of nonahydrated sodium sulfate are added. The suspension so obtained is heated at 82° C. until an "ink blue" solution is obtained; 2.1 mL (25.8 mmol) of 2-furaldehyde are then added to the reaction medium. The mixture gradually becomes brick red. After 1.25 h, 6.73 g (38.7 mmol) of sodium hydrosulfite are added to the reaction mixture, a chestnut brown precipitate gradually appears. The precipitate is filtered at high temperature through fritted glass and washed with water. The crude product is recrystallized in DMF. A second recrystallization is carried out in dichloromethane. The filtrate, after evaporation at a reduced pressure, is purified over a cake (support: silica 6–35 µm; conditioning: $CH_2Cl_2$/heptane, 80/20; eluant: $CH_2Cl_2$/MeOH, 100/0 to 90/10). The solid obtained is washed with heptane, uncolored over animal charcoal in dichloromethane, and filtered through micropores to produce, after evaporation at a reduced pressure, 0.32 g of 4,9-dihydro-4,9-dioxo-2-(2-furyl)-5-methoxynaphtho[2,3-d]thiazole or 4,9-dihydro-4,9-dioxo-2-(2-furyl)-8-methoxynaphtho[2,3-d]thiazole in the form of orange crystals.

Yield: 8%; Melting point: >260° C.; Rf: 0.60 ($CH_2Cl_2$/MeOH, 98/2); MS (APcI+): m/z 312 ($M^+H^+$); $^1$H-NMR ($CD_2Cl_2$): (ppm); 7.78 (dd, 1H, H-8 or H-5, $J_{H7-H8}$=7.63 Hz, $J_{H6-H8}$=1.22 Hz); 7.65 (t, 1H, H-7 or H-6, $J_{H7-H8}$ # $J_{H6-H7}$=7.62 Hz); 7.60 (dd, 1H, H-5', $J_{H4'-H5'}$=1.53 Hz, $J_{H3'-H5'}$=0.92 Hz); 7.33 (dd, 1H, H-6 or H-7 in [sic; at] a of the methoxy group, $J_{H6-H7}$=8.24 Hz, $J_{H6-H8}$ or $J_{H5-H7}$=0.92 Hz); 7.31 (s, 1H, H-3'); 6.59 (dd, 1H, H-4', $J_{H3'-H4'}$=3.67 Hz, $J_{H4'-H5'}$=1.83 Hz); 3.96 (s, 3H, OC$\underline{H}_3$); IR (KBr) ν ($cm^{-1}$); 3112 (C—H); 1674 (C=O); 1655 (C=N).

EXAMPLE 57

4,9-Dihydro-4,9-dioxo-2-(2-furyl)-5-hydroxynaphtho-[2,3-d]thiazole or 4,9-Dihydro-4,9-dioxo-2-(2-furyl)-8-hydroxynaphtho-[2,3-d]thiazole To a solution of 4,9-dihydro-4,9-dioxo-2-(2-furyl)-5-methoxynaphtho[2,3-d]thiazole or 4,9-dihydro-4,9-di-oxo-2-(2-furyl)-8-methoxynaphtho[2,3-d]thiazole (230 mg, 0.73 mmol) in 20 mL of acetic acid, 0.90 mL of 47% hydrobromic acid (7.69 mmol) is added. The reaction mixture under stirring is heated to reflux for 5 h. After return to ambient temperature, water (30 mL) is added to the reaction medium. This solution is then extracted with dichloromethane. The organic phase is washed with water until the pH is neutral. After drying on calcium chloride, the organic phase is evaporated at a reduced pressure. The raw reaction product is purified over a cake (support: silica 6–35 µm; eluant $CH_2Cl_2$). The product, dissolved in dichloromethane, is uncolored over animal charcoal. After washing with heptane, 110 mg of 4,9-dihydro-4,9-dioxo-2-(2-furyl)-5(or 8)hydroxynaphtho[2,3-d]thiazole in the form of an orange powder are obtained.

Yield: 50%; Melting point: 257° C.; Rf: 0.50 ($CH_2Cl_2$); MS (APcI+): m/z 298 ($M^+H^+$); $^1$H-NMR ($CD_2Cl_2$): δ (ppm); 12.25 (s, 1H, O$\underline{H}$); 7.77 (dd, 1H, H-8 or H-5, $J_{H7-H8}$ or $J_{H5-H6}$=7.63 Hz, $J_{H5-H7}$=1.22 Hz); 7.70 (dd, 1H, H-5', $J_{H4'-H5'}$=1.84 Hz, $J_{H3'-H5'}$=0.92 Hz); 7.68 (t, 1H, H-7 or H-6 at b of the hydroxy group, $J_{H7-H8}$ or $J_{H5-H6}$=7.63 Hz, $J_{H6-H7}$=8.23 Hz); 7.41 (d, 1H, H-3', $J_{H3'-H4'}$=3.67 Hz); 7.34 (dd, 1H, H-6 or H-7 at a of the hydroxy group, $J_{H6-H7}$=8.23 Hz, $J_{H6-H8}$ or $J_{H5-H7}$=1.22 Hz); 6.69 (dd, 1H, H-4', $J_{H3'-H4'}$=3.66 Hz, $J_{H4'-H5'}$=1.83 Hz); $^{13}$C-NMR ($CD_2Cl_2$): δ (ppm); 183.72 (1C, C-4 or C-9); 177.73 (1C, C-9 or C-4); 164.31 (1C, C-5 or C-8); 163.45 (1C, C-2); 155.15 (1C, C-2'); 148.41 (1C, C-3a); 146.68 (1C, C-5'); 142.00 (1C, C-9a); 137.07 (1C, C-7 or C-6 at β of the hydroxy group); 133.76 (1C, C-8a or C-4a); 125.74 (1C, C-8 or C-5); 120.32 (1C, C-6 or C-7 at α of the hydroxy group); 115.69 (1C, C-4a or C-8a); 113.75 and 114.07 (2C, C-3' and C-4'); IR (KBr): ν ($cm^{-1}$); 3400 (OH); 3124 (C—H); 1644 (C=O); 1584 (C—C).

EXAMPLES 58 AND 59

4,9-Dihydro-4,9-dioxo-2-(2-furyl)-6-methoxynaphtho-[2,3-d]thiazole and 4,9-Dihydro-4,9-dioxo-2-(2-furyl)-7-methoxynaphtho-[2,3-d]thiazole Under an inert atmosphere, to 2.00 g (7.1 mmol) of a mixture of 2-amino-3-bromo-1,4-dihydro-1,4-dioxo-6-methoxynaphthalene and 3-amino-2-bromo-1,4-dihydro-1,4-dioxo-6-methoxynaphthalene, 75 mL of an aqueous solution containing 4.25 g (17.7 mmol) of nonahydrated sodium sulfide are added. The suspension so obtained is heated at 80° C.; the naphthoquinone dissolves gradually to produce a "ink blue" solution; 1.2 mL (14.2 mmol) of 2-furaldehyde are then added to the reaction medium. The mixture gradually becomes brick red. After 1½ h and cooling to 50° C., 2.45 g (14.2 mmol) of sodium hydrosulfite are added to the reaction mixture, and a chestnut brown precipitate appears. The precipitate is hot filtered through fritted glass and washed with water until the washing waters are colorless. After drying in the oven under vacuum, the crude product is purified over a silica gel cake (silica 6–35 mm, eluant $CH_2Cl_2$/MeOH, 98/2); 1.15 g (3.7 mmol) of the mixture of 4,9-dihydro-4,9-dioxo-2-(2-furyl)-6-methoxynaphtho-[2,3-d]thiazole and 4,9-dihydro-4,9-dioxo-2-(2-furyl)-7-methoxynaphtho[2,3-d]thiazole [are obtained].

The separation of the two isomers is performed by three successive low-pressure chromatographies of the mixture (silica 6–35 µm, eluant $CH_2Cl_2$/AcOEt, 99/1). After color removal and recrystallization of each isomer in dichloromethane, 0.210 g of orange crystals of the more polar product and 0.300 g of orange crystals of the less polar product are obtained.

The More Polar Product

Yield: 9.5%; Melting point: >260° C.; Rt: 0.58 ($CH_2Cl_2$/AcOEt, 90/10); MS (I.E.): m/z 311 ($M^+$); $^1$H-NMR ($CD_2Cl_2$): δ (ppm); 8.22 (d, 1H, H-8 or H-5, $J_{H5-H6}$ or $J_{H7-H8}$=8.85 Hz); 7.69 (sl, 1H, H-5'); 7.66 (d, 1H, H-5 or H-8 at a of the methoxy group, $J_{H5-H7}$ or $J_{H6-H8}$=2.74 Hz); 7.40 (d, 1H, H-3', $J_{H3'-H4'}$=3.66 Hz); 7.27 (dd, 1H, H-7 or H-6, $J_{H5-H6}$ or $J_{H7-H8}$=8.55 Hz, $J_{H6-H8}$ or $J_{H5-H7}$=2.45 Hz); 6.68 (dd, 1H, H-4', $J_{H3'-H4'}$=3.66 Hz, $J_{H4'-H5'}$=1.83 Hz); 3.98 (s, 3H, $CH_3O$ at 6 or 7); I.R. (KBr): ν ($cm^1$); 1675 (C=O), 1650 (C=N), 1589.

The Less Polar Product

Yield: 13.5%; Melting point: >260° C.; Rf: 0.68 ($CH_2Cl_2$/AcOEt, 90/10); MS (I.E.): m/z 311 ($M^+$); $^1$H-NMR ($CD_2Cl_2$): δ (ppm); 8.15 (d, 1H, H-8 or H-5, $J_{H5-H6}$ or $J_{H7-H8}$=8.55 Hz); 7.73 (d, 1H, H-5 or H-8 at a of the methoxy group, $J_{H5-H7}$ or $J_{H6-H8}$=2.75 Hz); 7.68 (d, 1H, H-5', $J_{H4'-H5'}$=1.83 Hz); 7.38 (d, 1H, H-3', $J_{H3'-H4'}$=3.67 Hz); 7.25 (dd, 1H, H-7 or H-6, $J_{H5-H6}$ or $J_{H7-H8}$=8.55 Hz or $J_{H5-H7}$=2.75 Hz); 6.68 (dd, 1H, H-4', $J_{H3'-H4'}$=3.66 Hz, $J_{H4'-H5'}$=1.83 Hz); 3.99 (s, 3H, $CH_3O$ at 6 or 7); I.R. (KBr): ν ($cm^{-1}$); 1681 (C=O), 1645 (C=N), 1586.

EXAMPLES 60 AND 61

4,9-Dihydro-4,9-dioxo-2-furyl-6-methylnaphtho[2,3-d]-thiazole and 4,9-Dihydro-4,9-dioxo-2-furyl-7-methylnaphtho[2,3-d]-thiazole Synthesis Intermediates:

2-Amino-3-chloro-1,4-dihydro-1,4-dioxo-6-methylnaphthalene and

2-Amino-3-chloro-1,4-dihydro-1,4-dioxo-7-methylnaphthalene

To a solution consisting of 6.00 g (25 mmol, 1.0 eq) of a mixture of 2-chloro-1,4-dihydro-1,4-dioxo-6-methylnaphthalene (CAS No. 87 170-60-3) and 2-chloro-1,4-dihydro-1,4-dioxo-7-methylnaphthalene (CAS No. 87 170-61-4) along with 250 mL of glacial acetic acid, 2.60 g (40 mmol, 1.6 eq) of sodium nitride dissolved in 16 mL of distilled water are added in a single aliquot. This mixture is heated at 80° C. for 5 h; its color changes from yellow to orange. After cooling, the reaction medium is evaporated to dryness, and the raw product obtained is purified on a silica bed (support: silica 6–35 μm, d 10 cm, h 5 cm, solid deposit, eluant: heptane/ethyl acetate, 92/8) to produce, after evaporation of the solvent, 0.44 g of a mixture of 2-amino-3-chloro-1,4-dihydro-1,4-dioxo-6-methylnaphthalene and 2-amino-3-chloro-1,4-dihydro-1,4-dioxo-7-methylnaphthalene in the form of red crystals.

Yield: 8%; Rf: 0.38 (heptane/diethyl acetate, 70/30); MS (APcI+): m/z 222/226 (M$^+$H$^+$); $^1$H-NMR (CDCl$_3$): δ (ppm); 7.99 and 7.95 (2d, 2H, protons at b of CH$_3$, J=7.93 Hz); 7.87 (s, 2H, protons at a of CH$_3$); 7.56 and 7.48 (2d, 2H, protons at a of CH$_3$); 2.49 and 2.47 (2s, 6H, 2×CH$_3$).

4,9-Dihydro-4,9-dioxo-2-furyl-6-methylnaphtho[2,3-d]-thiazole and 4,9-Dihydro-4,9-dioxo-2-furyl-7-methylnaphtho[2,3-d]-thiazole

EXAMPLES 60 AND 61

To a solution consisting of 1.3 g (5.4 mmol, 6.0 eq) of nonhydrated sodium sulfide and 3.2 mL of a sodium hydroxide solution prepared earlier at pH 10.7, 0.2 g (0.9 mmol, 1.0 eq) of a mixture of 2-amino-3-chloro-1,4-dihydro-1,4-dioxo-6-methylnaphthalene and 2-amino-3-chloro-1,4-dihydro-1,4-dioxo-7-methylnaphthalene is added. This suspension, heated at 45° C., leads to a blue solution within 30 min; 149 μL (1.8 mmol, 2.0 eq) of 2-furaldehyde are then added and, after 15 min, 97 μL (1.7 mmol, 1.9 eq) of glacial acetic acid are added at 55° C. The reaction mixture, which has turned chestnut brown, is extracted with 6×100 mL of dichloromethane. The aqueous phases are combined, dried over magnesium sulfate, filtered, and evaporated to dryness. The product obtained is purified over a silica bed (support: silica 6–35 μm, 15 cm h, 5 cm φ, solid deposit, eluant: heptane/ethyl acetate, 90/10) to produce, after evaporation of the solvent, 0.13 g of the mixture of 4,9-dihydro-4,9-dioxo-2-furyl-6-methylnaphtho-[2,3-d]-thiazole and 4,9-dihydro-4,9-dioxo-2-furyl-7-methylnaphtho-[2,3-d]thiazole, [of] the two isomers, in the form of orange crystals.

The isomers are then separated by preparative plates (support: alumina, eluant: dichloromethane/heptane, 70/30).

Yield: 48.8% (mixture of the two isomers).

The More Polar Product

Rf: 0.42 (dichloromethane/heptane, 70/30, alumina); MS (APcI+): m/z 296 (M$^+$H$^+$); $^1$H-NMR (CD$_2$Cl$_2$): δ (ppm); 8.20 (d, 1H, H-5 or H-8 at b of CH$_3$, J$_{H5\text{-}H6}$ or J$_{H7\text{-}H8}$=7.93 Hz); 8.05 (m, 1H, H-5 or H-8 at a of CH$_3$); 7.73 (dd, 1H, H-5', J$_{H4'\text{-}H5'}$=1.83 Hz, J$_{H3'\text{-}H5'}$=0.61 Hz); 7.67 (d, 1H, H-6 or H-7, J$_{H5\text{-}H6}$ or J$_{H7\text{-}H8}$=7.94 Hz, at a of CH$_3$); 7.44 (dd, 1H, H-3', J$_{H3'\text{-}H4'}$=3.67 Hz, J$_{H3'\text{-}H5'}$=0.61 Hz); 6.72 (dd, 1H, H-4', J$_{H3'\text{-}H4'}$=3.66 Hz, J$_{H4'\text{-}H5'}$=1.83 Hz); 2.57 (s, 3H, CH$_3$); $^{13}$C-NMR (CD$_2$Cl$_2$): δ (ppm); 146.41 (1C, C-5'); 135.31 (1C, C-6 or C-7, at a of CH$_3$); 127.99 (1C, C-5 or C-8); 127.55 (1C, C-5 or C-8); 113.70 (1C, C-3'); 113.59 (1C, C-4'); 21.94 (1C, CH$_3$);

The Less Polar Product

Rf: 0.50 (dichloromethane/heptane, 70/30, alumina); MS (APcI+): m/z 296 (M$^+$H$^+$); $^1$H-NMR (CD$_2$Cl$_2$): δ (ππμ); 8.01 (m, 2H, H-5, H-8); 7.60 (dd, 1H, H-5', J$_{H4'\text{-}H5'}$=1.83 Hz, J$_{H3'\text{-}H5'}$=0.61 Hz); 7.53 (d, 1H, H-6 or H-7, J$_{H5\text{-}H6}$ or J$_{H7\text{-}H8}$=7.33 Hz, at a of CH$_3$); 7.31 (dd, 1H, H-3', J$_{H3'\text{-}H4'}$=3.66 Hz, J$_{H3'\text{-}H5'}$=0.61 Hz); 6.60 (dd, 1H, H-4', J$_{H3'\text{-}H4'}$=3.66 Hz, J$_{H4'\text{-}H5'}$=1.83 Hz); 2.46 (s, 3H, CH$_3$); $^{13}$C-NMR (CD$_2$Cl$_2$): δ (ppm); 176.28 (2C, C=O); 145.99 (1C, C-5); 134.64 (1C, C-6 or C-7, at a of CH$_3$); 127.94 (1C, C-5 or C-8); 126.83 (1C, C-5 or C-8); 113.24 (1C, C-3'); 113.18 (1C, C-4'); 21.74 (1C, CH$_3$).

EXAMPLES 62 AND 63

4,9-Dihydro-4,9-dioxo-6-methyl-2-phenylnaphtho[2,3-d]thiazole and 4,9-Dihydro-4,9-dioxo-7-methyl-2-phenylnaphtho[2,3-d]thiazole To a solution consisting of 1.3 g (5.4 mmol, 6.0 eq) of nonhydrated sodium sulfide and 3.2 mL of a sodium hydroxide solution, which was first prepared at a pH of 10.7, 0.5 g (0.9 mmol, 1.0 eq) of a mixture of 2-amino-3-chloro-1,4-dihydro-1,4-dioxo 6-methylnaphthalene and 2-amino-3-chloro-1,4-dihydro-1,4-dioxo-7-methylnaphthalene is added. This solution, when heated at 45° C., turns blue within 30 min; 184 μL (1.8 mmol, 2.0 eq) of benzaldehyde are then added to the reaction medium. The mixture, when heated at 55° C., turns green within 30 min. After the addition of 291 μL (5.0 mmol, 5.5 eq) of glacial acetic acid, a chestnut brown precipitate forms, which is filtered through fritted glass, then washed with dichloromethane. The raw product obtained is purified on a silica bed (support: silica 6–35 μm, d=5 cm, h=5 cm, solid deposit, eluant: heptane/ethyl acetate, 90/10) to produce, after evaporation of the solvents, 90 mg of the mixture of 4,9-dihydro-4,9-dioxo-6-methyl-2-phenylnaphtho[2,3-d]-thiazole and 4,9-dihydro-4,9-dioxo-7-methyl-2-phenylnaphtho[2,3-d]thiazole in the form of yellow crystals. These isomers are separated on preparative plates (support: alumina, eluant: dichloromethane/heptane, 70/30).

Yield: 33% (mixture of the two isomers).

The More Polar Product Rf: 0.50 (dichloromethane/heptane, 70/30, alumina); MS (APcI+): m/z 306 (M$^+$H$^+$); $^1$H-NMR (CD$_2$Cl$_2$): δ (ppm); 8.10 (d, 1H, H-5 or H-8, J$_{H5\text{-}H6}$ or J$_{H7\text{-}H8}$=7.63 Hz); 8.03 (m, 2H, H-2' and H-6'); 7.93 (bs, 1H, H-5 or H-8, at a of CH$_3$); 7.55 (d, 1H, H-6 or H-7, J$_{H5\text{-}H6}$ or J$_{H7\text{-}H8}$=7.93 Hz); 7.46 (m, 3H, H-3', H-4', H-5'); 2.45 (s, 3H, CH$_3$); $^{13}$C-NMR (CD$_2$Cl$_2$): δ (ppm); 135.36 (1C, C-6 or C-7); 132.60 (1C, C-4'); 129.65 (2C, C-2', C-6'); 128.01 (1C, C-5 or C-8); 127.90 (2C, C-3', C-5'); 127.55 (1C, C-5 or C-8); 21.93 (1C, CH$_3$);

The Less Polar Product

Rf: 0.62 (dichloromethane/heptane, 70/30, alumina); MS (APcI+): m/z 306 (M$^+$H$^+$); $^1$H-NMR (CD$_2$Cl$_2$): δ (ppm); 8.09–8.00 (m, 4H, H-5, H-8, H-2', H-6'). 7.53 (d, 1H, H-6 or H-7, $J_{H5-H6}$ or $J_{H7-H8}$=7.93 Hz); 7.46 (m, 3H, H-3', H-4', H-5'); 2.46 (s, 3H, CH$_3$); $^{13}$C-NMR (CD$_2$Cl$_2$): δ (ppm); 134.98 (1C, C-6 or C-7); 132.59 (1C, C-4'); 129.66 (2C, C-2', C-6'); 128.36 (1C, C-5 or C-8); 127.90 (2C, C-3', C-5'); 127.25 (1C, C-5 or C-8); 22.0 (1C, CH$_3$);

EXAMPLES 64 AND 65

4,9-Dihydro-4,9-dioxo-2-furyl-5-methylnaphtho[2,3-d]-thiazole and 4,9-Dihydro-4,9-dioxo-2-furyl-8-methylnaphtho[2,3-d]-thiazole Synthesis Intermediates:

2,3-Dibromo-1,4-dihydro-1,4-dioxo-5-methylnaphthalene

To 14.5 g (84 mmol, 1 eq) of 1,4-dihydro-1,4-dioxo-5-methylnaphthalene, 200 mL of carbon tetrachloride, then 17.2 mL (337 mmol, 4 eq) of bromine, are added. The solution turns red, then 22.94 g (168 mmol, 2 eq) of sodium acetate are added. After 96 h of reflux, the reaction medium is filtered, washed with carbon tetrachloride, and evaporated to dryness; the product is purified on a cake (Φ=6.5 cm, height=5 cm, deposit=solid, support=silica, eluant CH$_2$Cl$_2$); after evaporation to dryness, an orangish chestnut-brown paste is obtained. A first crystallization with dichloromethane yields 8.25 g of 2,3-dibromo-1,4-dihydro-1,4-dioxo-5-methylnaphthalene in the form of yellow crystals; a second recrystallization with acetonitrile produces 11.90 g of 2,3-dibromo-1,4-dihydro-1,4-dioxo-5-methylnaphthalene in the form of yellow crystals.

Yield: 72%; Rf: 0.70 (ethyl acetate/heptane, 50/50); MS (APcI−): m/z 328, 330, 332 (M$^-$); $^1$H-NMR (CDCl$_3$): δ (ppm); 8.11 (dd, 1H, H-8, $J_{H7-H8}$=7.02 Hz, $J_{H6-H8}$=1.53 Hz); 7.63 (m, 2H, H-6, H-7); 2.76 (s, 3H, CH$_3$); IR (KBr): ν (cm$^{-1}$); 1670 (C=O); 1570 (C=C);

2-Amino-3-bromo-1,4-dihydro-1,4-dioxo-5-methylnaphthalene

2-Amino-3-bromo-1,4-dihydro-1,4-dioxo-8-methylnaphthalene

To 8 g (24 mmol, 1 eq) of 2,3-dibromo-1,4-dihydro-1,4-dioxonaphthalene, 200 mL of glacial acetic acid (3.5 mmol, 6.85 eq), then 2.52 g (38 mmol) of sodium nitride dissolved in 17.5 mL of water are added. After 12 h at 70° C., the solution turns red. The reaction mixture is cooled and evaporated to dryness, the product is purified on a cake (Φ=5 cm, h=5 cm, deposit=solid, support=silica, eluant= concentration gradient of ethyl acetate/heptane 10/90 then 20/80). 525 mg of the mixture 2-amino-3-bromo-1,4-dihydro-1,4-dioxo-5-methylnaphthalene and of 2-amino-3-bromo-1,4-dihydro-1,4-dioxo-8-methylnaphthalene in the form of red-orangish crystals are obtained.

Yield: 8%; Rf: 0.58 (ethyl acetate/heptane, 50/50); MS (APcI−): m/z 264 266(M$^-$); $^1$H-NMR (CDCl$_3$): δ (ppm); 8.12 (d, 1H, H-5 or H-8, $J_{H7-H8}$ or $J_{H5-H6}$=7.32 Hz); 7.58 (t, 1H, H-6 or H-7, $J_{H5-H6}$ or $J_{H7-H8}$=7.63 Hz); 7.44 (d, 1H, H-6 or H-7, $J_{H5-H6}$ or $J_{H7-H8}$=7.63 Hz); 2.74 (s, 3H, CH$_3$).

4,9-Dihydro-4,9-dioxo-2-furyl-5-methylnaphtho[2,3-d]-thiazole and 4,9-Dihydro-4,9-dioxo-2-furyl-8-methylnaphtho[2,3-d]-thiazole To a solution consisting of 1.35 g (5.63 mmol) of non-ahydrated sodium sulfide and 3.38 mL (1.8×10$^{-1}$ mol) of a sodium hydroxide solution, which was first prepared with pH=9, 0.25 g (0.93 mmol) of a mixture of 2-amino-3-bromo-1,4-dihydro-1,4-dioxo-5-methylnaphthalene and 2-amino-3-bromo-1,4-dihydro-1,4-dioxo-8-methylnaphthalene is added. This suspension is heated at 45° C. and it turns blue after 40 min; 156 mL (1.87 mmol) of 2-furaldehyde are added; after 15 min, 102 μL (1.178 mmol) of glacial acetic acid are added at 55° C. The reaction mixture, which has turned chestnut brown, is then extracted with 2×100 mL of dichloromethane, dried over magnesium sulfate, filtered, and evaporated to dryness. An alumina cake is then prepared (eluant: concentration gradient: 50/50 to 70/30 in dichloromethane/heptane.

The yield then consists of 51 mg (18%) of a mixture of 4,9-dihydro-4,9-dioxo-2-furyl-5-methylnaphtho[2,3-d]thiazole and 4,9-dihydro-4,9-dioxo-2-furyl-8-methylnaphtho[2,3-d]-thiazole. The separation of the isomers on a preparative plate (support: alumina, eluant: dichloromethane/heptane) produces a more polar product and a less polar product.

The Less Polar Product

Rf: 0.61 (dichloromethane/heptane, 70/30, alumina); MS (APcI+): m/z 296 (M$^+$H$^+$); $^1$H-NMR (CD$_2$Cl$_2$): δ (ppm); 8.07 (d, 1H, H-5 or H-8 at g of CH$_3$, $J_{H5-H6}$ or $J_{H7-H8}$=9.55 Hz); 7.58 (m, 3H, H-6 and H-7 at α and β of CH$_3$ and H-5'); 7.32 (d, 1H, H-3', $J_{H3'-H4'}$=3.32 Hz); 6.60 (dd, 1H, H-4', $J_{H3'-H4'}$=3.1 Hz, $J_{H4'-H5'}$=1.2 Hz); 2.77 (s, 3H, CH$_3$); $^{13}$C-NMR (CD$_2$Cl$_2$): δ (ppm); 145.24 (1C, C-5'); 137.82–132.24 (2C, C-6 and C-7); 124.90 (1C, C-5 or C-8); 112.54 and 112.44 (2C, C-3' and C-4').

The More Polar Product

Rf: 0.53 (dichloromethane/heptane, 70/30, alumina); MS (APcI+): m/z 296 (M$^+$H$^+$); $^1$H-NMR (CD$_2$Cl$_2$): δ (ppm); 8.07 (d, 1H, H-5 or H-8, $J_{H5-H6}$ or $J_{H7-H8}$=4.98 Hz, $J_{H5-H7}$ or $J_{H6-H8}$=1.5 Hz); 7.60 (m, 3H, H-6 and H-7 at α and β of CH$_3$ and H-5'); 7.32 (d, 1H, H-3', $J_{H3'-H4'}$=3.73 Hz); 6.45 (dd, 1H, H-4', $J_{H3'-H4'}$=3.32 Hz, $J_{H4'-H5'}$=1.66 Hz); 2.77 (s, 3H, CH$_3$); $^{13}$C-NMR (CD$_2$Cl$_2$): δ (ppm); 189.69 and 184.57 (2C, C-4 and C-9); 145.38 (1C, C-5'); 129.29 (1C, C-6 or C-7 at β of CH$_3$); 126.04–132.24 (1C, C-6 or C-7 at a of CH$_3$); 123.45 (1C, C-5 or C-8 at δ of CH$_3$); 113.67 and 113.57 (2C, C-3' and C-4'); 23.39 (1C, CH$_3$).

EXAMPLES 66 AND 67

4,9-Dihydro-4,9-dioxo-5-methyl-2-phenylnaphtho[2,3-d]thiazole and 4,9-Dihydro-4,9-dioxo-8-methyl-2-phenylnaphtho[2,3-d]thiazole To a solution consisting of 1.35 g (5.63 mmol, 6 eq) of nonahydrated sodium sulfide and 3.38 mL (890 mmol, 193 eq) of a sodium hydroxide solution which had first been prepared at pH=9, 0.25 g (0.93 mmol) of the mixture of 2-amino-3-bromo-1,4-dihydro-1,4-dioxo-6-methylnaphthalene and 2-amino-3-bromo-1,4-dihydro-1,4-dioxo-7-methylnaphthalene is obtained. This suspension, when heated at 45° C., turns blue after 30 min; 191 mL (1.87 mmol, 2 eq) of benzaldehyde are added; after 15 min, 102 mL (1.78 mmol) of glacial acetic acid are then added at 55° C. The reaction mixture, which has turned chestnut brown, is extracted with 3×100 mL of dichloromethane, washed until neutral, and dried over magnesium sulfate to produce 38 mg (13%) of raw product. After separation of the two isomers on a preparative plate (support alumina, eluant dichloromethane/heptane 70/30), two products are obtained: 4,9-dihydro-4,9-dioxo-5-methyl- 2-phenylnaphtho[2,3-d]-thiazole and 4,9-dihydro-4,9-dioxo-8-methyl-2-phenylnaphtho[2,3-d]thiazole.

The Less Polar Product

Rf: 0.58 (dichloromethane/heptane, 70/30, alumina); MS (IE): m/z 305 (M$^+$); $^1$H-NMR (CD$_2$Cl$_2$): δ (ppm); 8.07 (m, 3H, H-2', H-6', H-5 or H-8); 7.61 (m, 2H, H-6, H-7); 7.49 (m, 2H, H-3', H-5'); 7.30 (m, 1H, H-4'); 2.76 (s, 3H, CH$_3$).

The More Polar Product

Rf: 0.51 (dichloromethane/heptane, 70/30, alumina); MS (IE): m/z 305 (M$^+$); $^1$H-NMR (CD$_2$Cl$_2$): δ (ppm); 8.07 (m, 3H, H-2', H-6', H-5 or H-8 at g of CH$_3$); 7.60 (m, 2H, H-6, H-7); 7.49 (m, 2H, H-3', H-5'); 7.30 (m, 1H, H-4'); 2.77 (s, 3H, CH$_3$).

Example a 4,9-Dihydro-4,9-dioxo-2-methyl-1H-naphtho[2,3-d]imidazole

Reference: C.A. 67 97905t; Yield: 76%; Melting point: >260° C.; Rf: 0.44 (CH$_2$Cl$_2$/methanol, 97/3); MS (I.E.): m/z 212 (M$^+$.); $^1$H-NMR (DMSO d$_6$): δ (ppm); 13.74 (s, 1H, NH); 8.05 (dd, 2H, H-5, H-8, J$_{H5-H6}$=J$_{H7-H8}$=8.85 Hz; J$_{H5-H7}$=J$_{H6-H8}$=1.73 Hz); 7.82 (m, 2H, H-6, H-7); 2.45 (s, 3H, CH$_3$); $^{13}$C-NMR (DMSO d$_6$): δ (ppm); 178.15; 176.53 (2C, C-4, C-9); 153.80 (1C, C-2); 137.14 (1C, C-3a); 133.98, 133.99 (2C, C-6, C-7); 133.27, 133.10, 132.84 (3C, C-8a, C-9a, C-4a); 126.82 (2C, C-5, C-8); 14.01 (1C, CH$_3$); IR (KBr): ν (cm$^{-1}$); 3134 to 2897 (NH); 1678, 1672 (C=O).

Example b 4,9-Dihydro-4,9-dioxo-2-methyl-1-phenyl-1H-naphtho-[2,3-d]imidazole

Reference: C.A. 67 97905t; Yield: 72%; Melting point: 242° C.; Rf: 0.43 (CH$_2$Cl$_2$/methanol, 99/1); MS (I.E.): m/z 288 (M$^+$.); $^1$H-NMR (DMSO, d$_6$): δ (ppm); 8.23 (d, 1H, H-5 or H-8, J$_{H5-H6}$ or J$_{H7-H8}$=6.71 Hz); 7.90 (d, 1H, H-5 or H-8, J$_{H-5-H6}$ or J$_{H7-H8}$=6.71 Hz); 7.68 (m, 3H, H-3', H-4', H-5'); 7.60 (m, 2H, H-6, H-7); 7.37 (m, 2H, H-2', H-6'); 2.40 (s, 3H, CH$_3$); $^{13}$C-NMR (CDCl$_3$: δ (ppm); 179.13, 175.03 (2C, C-4, C-9); 153.66 (1C, C-2); 143.14 (1C, C-1'); 135.11 (1C, C-3a); 133.68, 133.51 (2C, C-6, C-7); 133.15, 133.01, 132.63 (3C, C-8a, C-9a, C-4a); 129.95, 129.69 (3C, C-3', C-4', C-5'); 126.93, 126.76, 126.43 (4C, C-2', C-6', C-5, C-8); 13.77 (1C, CH$_3$); IR (KBr): ν (cm$^{-1}$); 1674, 1663 (C=O).

Examiple c 4,9-Dihydro-4,9-dioxo-2-methyl-1-phenyl-1H-naphtho[2,3-d]imidazole sulfate Reference: C.A. 68 8764b; Yield: 47%; Melting point: >260° C.; Rf: 0.53 (CH$_2$Cl$_2$/methanol, 97.5/2.5); $^1$H-NMR (DMSO, d$_6$): δ (ppm); 8.11 (dd, 1H, H-5 or H-8, J$_{H5-H6}$ or J$_{H7-H8}$=8.85 Hz; J$_{H5-H7}$ or J$_{H6-H8}$=1.73 Hz); 8.00 (dd, 1H, H-5 or H-8, J$_{H5-H6}$ or J$_{H7-H8}$=8.85 Hz; J$_{H5-H7}$ or J$_{H6-H8}$=1.73 Hz); 7.94 (m, 2H, H-6, H-7); 7.82 (m, 2H, H-2', H-6'); 7.51 (m, 3H, H-3', H-4', H-5'); 5.54 (s, 1H, NH+); 2.30 (s, 3H, CH$_3$); IR (KBr): ν (cm$^{-1}$); 3414–2400 (broad NH$^+$ band); 1736, 1681 (C=O).

Example d 4,9-Dihydro-4,9-dioxo-1,2-dimethyl-1H-naphtho[2,3-d]imidazole

Reference: C.A. 66 104957w; Yield: 70%; Melting point: >253° C.; Rf: 0.49 (CH$_2$Cl$_2$/methanol, 98/2); MS (I.E.): m/z 226 (M$^+$.); $^1$H-NMR (CDCl$_3$): δ (ppm); 8.21, 8.09 (2m, 2H, H-5, H-8); 7.70 (m, 2H, H-6, H-7); 4.01 (s, 3H, CH$_3$); 2.56 (s, 3H, CH$_3$); $^{13}$C-NMR (CDCl$_3$: δ (ppm); 179.22, 178.44 (2C, C-4, C-9); 154.46 (1C, C-2); 134.18, 134.11 (2C, C-6, C-7); 133.37, 133.17 (2C, C-4a, C-8a); 127.37, 126.75 (2C, C-5, C-8); 32.74 (1C, CH$_3$); 13.64 (1C, CH$_3$); IR (KBr): ν (cm$^{-1}$); 1674 (C=O).

Example e 4,9-Dihydro-4,9-dioxo-2-phenyl-1H-naphtho[2,3-d]imidazole

Reference: C.A. 68 8764b; Yield: 34%; Melting point: >260° C.; Rf: 0.51 (CH$_2$Cl$_2$/diethyl acetate, 90/10); MS (I.E.): m/z 274 (M$^+$); $^1$H-NMR (DMSO d$_6$): δ (ppm); 14.40 (s, 1H, NH); 8.26 (m, 2H, H-5, H-8); 8.12 (m, 2H, H-2', H-6'); 7.87 (m, 2H, H-6, H-7); 7.54 (m, 3H, H-3', H-4', H-5'); $^{13}$C-NMR (DMSO d$_6$): δ (ppm); 179.13, 175.03 (2C, C-4, C-9); 152.60 (1C, C-2); 133.89 (2C, C-6, C-7); 132.60 (2C, C-9a, C-3a); 130.00 (2C, C-4a, C-8a); 129.03 (3C, C-3', C-4', C-5'); 126.82, 126.32 (4C, C-5, C-8, C-2', C-6'); IR (KBr): ν (cm$^{-1}$); 3232 (NH); 1681, 1664 (C=O).

Example f 4,9-Dihydro-4,9-dioxo-2-phenylnaphtho[2,3-d]oxazole

Reference: C.A. 87 53134z; Yield: 75%; Melting point: >260° C.; Rf: 0.60 (CH$_2$Cl$_2$/Heptane, 80/20); MS (I.E.): m/z 275 (M$^+$.); $^1$H-NMR (CDCl$_3$): δ (ppm); 8.33 (d, 2H, H-2', H-6', J$_{H2'-H3'}$=J$_{H5'-H6'}$=6.71 Hz); 8.27 (m, 2H, H-5, H-8); 7.82 (m, 2H, H-6, H-7); 7.58 (m, 3H, H-3', H-4', H-5'); $^{13}$C-NMR (CDCl$_3$: δ (ppm); 178.50, 173.05 (2C, C-4, C-9); 167.76 (1C, C-2); 134.52, 132.99 (2C, C-6, C-7); 129.21 (3C, C-3', C-4', C-5'); 128.33 (2C, C-2', C-6'); 127.50, 127.04 (2C, C-5, C-8); IR (KBr): ν (cm$^{-1}$); 1693, 1678 (C=O).

Example g 4,9-Dihydro-4,9-dioxo-2-(4-methylphenyl)-naphtho[2,3-d]oxazole

Reference: C.A. 87 53134z; Yield: 44%; Melting point: >260° C.; Rf: 0.50 (CH$_2$Cl$_2$); MS (I.E.): m/z 289 (M$^+$); $^1$H-NMR (CDCl$_3$): δ (ppm); 8.27 (m, 2H, H-5, H-8); 8.23 (d, 2H, H-2', H-6', J$_{H2'-H3'}$=J$_{H5'-H6'}$=8.24 Hz); 7.81 (m, 2H, H-6, H-7); 7.38 (m, 2H, H-3', H-5'); 2.46 (s, 3H, CH$_3$); $^{13}$C-NMR (CDCl$_3$: δ (ppm); 178.77, 173.80 (2C, C-4, C-9); 165.51 (1C, C-2); 143.95 (1C, C-3a); 135.80 (1C, C-4'); 134.29, 132.12 (3C, C-1', C-6, C-7); 131.70, 131.38 (2C, C-4a, C-8a); 129.93, 128.28 (4C, C-2', C-3', C-5', C-6'); 127.44, 126.99 (2C, C-5, C-8); 122.41 (1C, C-1'); 21.81 (1C, CH$_3$); IR (KBr): ν (cm$^{-1}$); 1668, 1678 (C=O).

Example h 4,9-Dihydro-4,9-dioxo-2-methylnaphtho[2,3-d]thiazole

Reference: C.A. 120 270267z; Yield: 11%; Melting point: >260° C.; Rf: 0.41 (CH$_2$Cl$_2$/methanol, 99/1); MS (I.E.): m/z 229 (M$^+$); $^1$H-NMR (CDCl$_3$): δ (ppm); 8.33, 8.21 (2dd, 2H, H-5, H-8, J$_{H5-H6}$=J$_{H7-H8}$=8.85 Hz); 7.80 (m, 2H, H-6, H-7); 2.91 (s, 3H, CH$_3$); $^{13}$C-NMR (CDCl$_3$): δ (ppm); 177.95, 176.95 (2C, C-4, C-9); 173.86 (1C, C-2); 153.10 (1C, C-3a); 142.14 (1C, C-9a); 133.90, 133.51 (2C, C-6, C-7); 132.06, 131.72 (2C, C-4a, C-8a); 127.29, 126.47 (2C, C-5, C-8); 19.83 (1C, CH$_3$); IR (KBr): ν (cm$^{-1}$); 1677, 1655 (C=O).

Example i

2-Amino-4,9-dihydro-4,9-dioxonaphtho[2,3-d]thiazole

Reference: C.A. 120 270267z; Yield: 96%; Melting point: >260° C.; Rf: 0.24 (CH$_2$Cl$_2$/methanol, 96/4); MS (I.E.): m/z 230 (MH$^+$); $^1$H-NMR (DMSO d$_6$): δ (ppm); 8.56 (s, 2H, NH$_2$); 8.03 (m, 2H, H-5, H-8); 7.83 (m, 2H, H-6, H-7); $^{13}$C-NMR (DMSO d$_6$): δ (ppm); 178.04, 177.31 (2C, C-4, C-9); 173.45 (1C, C-2); 154.61 (1C, C-3a); 145.95 (1C, C-9a); 134.34, 134.03 (2C, C-6, C-7); 133.18, 132.24 (2C, C-4a, C-8a); 126.99, 125.97 (2C, C-5, C-8); IR (KBr): ν (cm$^{-1}$); 3460, 3420 (NH$_2$), 1690, 1660 (C=O).

Example j 4,9-Dihydro-4,9-dioxo-2-phenylnaphtho[2,3-d]thiazole

Reference: C.A. 67 11450f; Yield: 68%; Melting point: 249° C.; Rf: 0.45 (CH$_2$Cl$_2$); MS (I.E.): m/z 291 (M$^+$); $^1$H-NMR (CDCl$_3$): δ (ppm); 8.30, 8.21 (2dd, 2H, H-5, H-8, J$_{H5-H6}$=J$_{H7-H8}$=8.85 Hz, J$_{H6-H8}$=J$_{H5-H7}$=1.73 Hz); 8.14 (m, 2H, H-2', H-6'); 7.83 (m, 2H, H-6, H-7); 7.56 (m, 3H, H-3', H-4', H-5'); $^{13}$C-NMR (CDCl$_3$): δ (ppm); 178.45, 172.67 (2C, C-4, C-9); 134.82, 134.44 (2C, C-6, C-7); 133.50, 133.24, 132.74, 132.01 (4C, C-9a, C-1', C-4a, C-8a); 129.75, 128.01 (5C, C-2', C-3', C-4', C-5', C-6'); 127.94, 127.18 (2C, C-5, C-8); IR (KBr): ν (cm$^{-1}$); 1675, 1660 (C=O).

Example k 4,9-Dihydro-4,9-dioxo-2-(2-pyridyl)-naphtho[2,3-d]thiazole

Reference: C.A. 109 130788t; Yield: 75%; Melting point: >260° C.; Rf: 0.60 (CH$_2$Cl$_2$/methanol, 97/3); MS (I.E.): m/z 292 (M$^+$); $^1$H-NMR (CDCl$_3$): δ (ppm); 8.69 (d, 1H, H-6', J$_{H5'-H6'}$=5.50 Hz); 8.47 (d, 1H, H-3', J$_{H3'-H4'}$=5.50 Hz); 8.36, 8.26 (2dd, 2H, H-5, H-8, J$_{H5-H6}$=J$_{H7-H8}$=8.85 Hz, J$_{H5-H7}$=J$_{H6-H8}$=1.73 Hz); 7.82 (m, 3H, H-4', H-6, H-7); 7.46 (m, 1H, H-5'); $^{13}$C-NMR (CDCl$_3$): δ (ppm); 178.17, 177.43 (2C, C-4, C-9); 158.76 (1C, Cquat); 151.11 (1C, C-6'); 147.86 (1C, C-4'); 134.77, 134.31 (2C, C-6, C-7); 133.50, 132.74 (2C, C-4a, C-8a); 128.04, 127.16 (2C, C-5, C-8); 121.15 (1C, C-3'); 118.45 (1C, C-5'); IR (KBr): ν (cm$^{-1}$); 1688, 1667 (C=O).

Example l 4,9-Dihydro-4,9-dioxo-2-(4-pyridyl)-naphtho[2,3-d]thiazole

Reference: C.A. 109 130788t; Yield: 75%; Melting point: >260° C.; Rf: 0.30 (CH$_2$Cl$_2$/methanol, 97/3); MS (I.E.): m/z 292 (M$^+$); $^1$H-NMR (CDCl$_3$): δ (ppm); 8.84 (d, 2H, H-2', H-6', J$_{H2'-H3'}$=J$_{H5'-H6'}$=5.50 Hz); 8.39, 8.26 (dd, 2H, H-5, H-8, J$_{H5-H6}$=J$_{H7-H8}$=8.85 Hz, J$_{H6-H8}$=J$_{H5-H7}$=1.73 Hz); 7.99 (d, 2H, H-3', H-5', J$_{H2'-H3'}$=J$_{H5'-H6'}$=5.50 Hz); 7.84 (m, 2H, H-6, H-7); $^{13}$C-NMR (CDCl$_3$): δ (ppm); 178.17, 172.50 (2C, C-4, C-9); 151.11 (2C, C-2', C-6'); 134.77, 134.31 (2C, C-6, C-7); 133.50, 132.74, 132.01 (4C, C-9a, C-4', C-4a, C-8a); 128.04, 127.16 (2C, C-5, C-8); 121.04 (2C, C-3', C-5'); IR (KBr): ν (cm$^{-1}$); 1688, 1667 (C=O).

Example m 4,9-Dihydro-4,9-dioxo-2-pyrrolylnaphtho[2,3-d]thiazole

Reference: C.A. 109 130788t; Yield: 17%; Melting point: 208° C. (dec); Rf: 0.44 (CH$_2$Cl$_2$/ethanol, 99/1); MS (I.E.): m/z 280 (M$^+$.); $^1$H-NMR (CD$_2$Cl$_2$): δ (ppm); 9.85 (ls, 1H, NH); 8.21, 8.17 (2dd, 2H, H-5, H-8, J$_{H5-H6}$=J$_{H7-H8}$=8.85 Hz, J$_{H5-H7}$=J$_{H6-H8}$=1.73 Hz); 7.79 (m, 2H, H-6, H-7); 7.07 (m, 1H, H-5'); 6.96 (m, 1H, H-3'); 6.35 (m, 1H, H-4'); IR (KBr): ν (cm$^{-1}$); 3286 (NH); 1676, 1647 (C=O).

Example n 4,9-Dihydro-4,9-dioxo-2-(2-furyl)-naphtho[2,3-d]thiazole

Reference: C.A. 67 11450f; Yield: 48%; Melting point: >260° C.; Rf: 0.55 (CH$_2$Cl$_2$/methanol, 99,5/0,5); MS (I.E.): m/z 281 (MH$^+$); $^1$H-NMR (CDC$_3$): δ (ppm); 8.37 (dd, 1H, H-5 or H-8, J$_{H5-H6}$ or J$_{H7-H8}$=8.85 Hz, J$_{H5-H7}$ or J$_{H6-H8}$=1.73 Hz); 8.23 (m, 1H, H-5 or H-8); 7.81 (m, 2H, H-6, H-7); 7.65 (d, 1H, H-5', J$_{H4'-H5'}$=1.97 Hz); 7.46 (d, 1H, H-3', J$_{H3'-H4'}$=3.94 Hz); 6.65 (dd, 1H, H-4', J$_{H3'-H4'}$=3.94 Hz, J$_{H4'-H5'}$=1.97 Hz); $^{13}$C-NMR (CDCl$_3$): δ (ppm); 178.25, 177.90 (2C, C-4, C-9); 163.94 (1C, C-2); 155.25 (1C, C-2'); 148.00 (1C, C-3a); 145.93 (1C, C-5'); 140.62 (1C, C-9a); 134.34, 134.09 (2C, C-6, C-7); 133.13, 132.68 (2C, C-4a, C-8a); 127.83, 126.91 (2C, C-5, C-8); 113.80 (1C, C-3'); 113.34 (1C, C-4'); IR (KBr): ν (cm$^{-1}$); 1683, 1658 (C=O).

Pharmacological Properties:

The study of the compounds of the present invention and their possible salts has demonstrated that they possess different pharmacological properties. Thus, most of the compounds have a selective tonic effect on veins, affecting the arterial system only at concentrations that are much greater than those producing activity on veins, except for some arteries, particularly cerebral arteries (carotid, basilar). The compounds reveal no affinity or very low affinity for a majority of the known pharmacological membrane receptors. Moreover, they increase the capillary resistance and decrease the vascular hyperpermeability induced by certain inflammatory agents. These properties are demonstrated in mammals, such as hamsters, rats, guinea pigs, and rabbits, under in vitro conditions (isolated vessels or vascular beds) and in vivo. For the in vitro studies, the compounds are dissolved in a pure aqueous solution or an aqueous solution containing DMSO (dimethyl sulfoxide). For the in vivo studies, they are administered intravenously or intraperitoneally in the form of an aqueous solution that may or may not contain DMSO, or by an oral route in suspension in 1% carboxymethylcellulose administered with a force-feeding probe at a volume of 10 mL/kg.

Pharmacological Study Models

Contractile Effects:

The contractile effects are measured in vitro under static conditions on vascular capacitance or resistance rings of saphenous, femoral, jugular, mesenteric, and caval veins . . . and on femoral, carotid, basilar, or mesenteric arteries, as well as the thoracic or abdominal aorta . . . in rats (Wistar, 200–250 g), rabbits (New Zealand, 2–2.5 kg), guinea pigs (Dunkin Hartley 250–300 g).

The rings are placed in a chamber for isolated organs (25 mL for capacitance vessels and 2.5 mL for resistance vessels according to Mulvany), and maintained under isometric conditions using two rigid threads inserted inside the vessel, avoiding causing damage to the endothelium. The vessels are bathed in a modified Krebs solution (in mM: NaCl=118; KCl=4.6; CaCl$_2$=2.5; MgSO$_4$=1.2; KH$_2$PO$_4$=1.17; NaHCO$_3$=25; glucose=11), continuously aerated using a gaseous mixture of 95% O$_2$ and 5% Co$_2$, at a pH=7.4, and regulated by thermostat at 37° C. The rings are adjusted to their optimal point as far as the tension-length relationship is concerned. The tensions developed generate an electrical signal through the intermediary of a force sensor (Wheatstone bridge). This signal is amplified before being either displayed on a Kipp & Zonen recorder, or digitized to be processed by computer (IOS, EMKA). The pharmacological studies are carried out after a few standardized preliminary contractile stimulations using a depolarizing solution (hyperpotassic type obtained by replacing NaCl with KCl in equimolar quantities), along with rinsings and periods of equilibration in a pure physiological solution. The presence of endothelium is verified by the relaxation induced by increasing the concentration of acetylcholine after the stabilization of a vascular precontraction.

The forces of contraction developed by the vascular rings in response to the different compounds are studied on quiescent or electrically stimulated vessels (5–8 Hz), by a "physiological" depolarizing hyperpotassic solution (KCl: 20, 40 mM), by noradrenaline (increasing concentrations), [and by] serotonin (increasing concentrations).

The contractions are expressed in mg force or as a percentage of the maximum contraction at the time of the depolarization with a "physiological" hyperpotassic solution.

The contractile effects are also measured in vitro under dynamic flow conditions, by the pressure developed by the vascular beds that are perfused at a constant flow rate. At the mesenteric level, the selective effect on veins is studied using the model of a double simultaneous and separate infusion of the arterial and venous networks model developed by T. Warner (British J. Pharmacol., 1990, Vol. 99, pp. 427–433). The separation of the two networks is achieved by cutting the vessels and the tissues along the intestinal border. The networks are perfused at 2 mL.min$^{-1}$ with a Krebs solution (37.5° C.), which is aerated using 95% $O_2$ and 5% $CO_2$. In vivo, the arterial and venous pressures are measured in the anesthetized animal, under basal conditions and after circulatory arrest caused by the swelling of a balloon catheter introduced at the level of the left atrium. During the cardiac arrest, the venous tone (average circulatory filling pressure at a constant blood volume) is calculated from the venous and arterial pressures measured at equilibrium and corrected as a function of the relative differences in compliance between these two networks (Samar & Coleman, Am. J. Physiol., 1978, Vol. 234: pp. H94-100; Yamamoto et al., Am. J. Physiol., 1980, Vol. 238: pp. H823–828).

In the conscious animal, the arterial pressures are measured according to the classical method derived from Riva Rocci, by the analysis of the acoustical wave transmitted at the arterial level and transformed by a ceramic piezo transducer placed on the tail of the rat, downstream from a sleeve that is automatically inflated by a pressure generator. At the microcirculatory level, the variations in the sections of the veinules and arterioles are studied in vivo in the model of the dorsal cutaneous chamber of conscious hamsters, after a video microscopic recording (microscope Leitz Ergolux equipped with a halogen source for the illumination and its black-and-white CD video camera HPR 610) and computer analysis (software Visicap, Pack ICAP) of the images.

After anesthesia with sodium pentobarbital (60 mg/kg in i.p. administration), the back of the animal is shaved and hair is pulled so as to be able to put an observation chamber (Professor Gebhard, Heidelberg) on the back skin. The two parts of this chamber are sewn after careful removal of a certain level of skin thicknesses, which can impede the observation. A jugular catheter is placed for the i.v. administration of the products, 48 h after the operation.

Effects on the Induced Capillary Hyperpermeability:

The vascular permeability is studied in vivo by measuring the extravasation of albumin, the quantity of which is determined using an albumin-binding dye (Evans blue).

The hyperpermeability is induced by the intradermal injection of a solution of histamine, bradykinin, or zymosan.

The technique is derived from that described by Beach & Steinetz, J. Pharmacol. Exp. Therap., 1961, Vol. 131: pp. 400–406.

The abdominal walls of the rats (Wistar, 200–230 g) are shorn 1 h before the start of the experiment. The product to be tested is injected by the intraperitoneal route or orally 1–4 h before the sacrifice. The rats are anesthetized with a halothane mixture. They then receive an intradermal injection in their abdomen of 0.10 or 0.15 mL (or for histamine 6.7 or 10 μm) of inflammatory agent and an intravenous injection of 1 mL of 0.5% Evans blue solution in the vein of the penis. These injections are carried out 30 min before the sacrificing.

30 min after these two injections, the rats are sacrificed by cervical dislocation.

At the site of the injection of the inflammatory agent, the skin is cut and placed into glass tubes with a ground[-glass] neck containing 3 mL of fuming hydrochloric acid. The digestion of the skin [by HCl] is carried out by placing it in contact with a water bath at 37° C. for at least 1 h; 3 mL of 12.8% benzalkonium chloride are then added. After allowing the preparation to stand for 30 min, 7 mL of dichloromethane are added. The tubes are periodically agitated for 1 h. The aqueous phase is eliminated by aspiration, and the organic "dichloromethane" phase is filtered. The optical densities are quantified by absorption spectrophotometry at a wavelength of 620 nm, against a blank [control] containing only dichloromethane. The averages of the optical densities of the different lots of treated or control animals are calculated, then a percentage of variation of the values corresponding to the treated [experimental] animals compared to those of the control animals is calculated.

The effect of the compounds on the hyperpermeability induced by inflammatory agents, such as histamine and bradykinin, is also studied after intravenous injection in a bolus in the model of the dorsal cutaneous chamber of hamsters and according to the method developed by Gimeno et al., described earlier ("A new technique using intravital videomicroscopy for macromolecular permeability measurement," $18^{th}$ European Congress on Microcirculation, Rome, 1994) using videomicroscopy and image analysis by quantification of the distribution of the intra- and extravascular fluorescence of the fluorescent marker (FITC-Dextran) injected in a bolus through the jugular catheter (63 mg/kg for a volume defined at 1 mL/kg). The microscope is equipped with a fluorescence source and a combination of filters (excitation in the blue range 450–490 nm, and 515-nm stop filter).

Effects on the Capillary Resistance:

The increase in the capillary resistance is evaluated by the modification of the petechial index (negative pressure inducing the extravasation of the erythrocytes), measured by a method derived from the angiosterrometer of Parrot.

The studies are carried out on male Wistar rats with an average weight of 200 g (approximate age six weeks). The bottom area of the back is shorn, then the hair is pulled by means of a paste based on a derivative of thioglycolic acid and calcium hydroxide. After approximately 30 min, the skin is abundantly rinsed and dried.

On the day of the study, the rats are maintained without constraint. A low pressure of 80 mm of mercury is applied. If the petechiae (extravasation of erythrocytes) have not appeared within 15 sec, the low pressure is increased as a countermeasure, keeping the suction cap at the same place.

The minimum low pressure where petechias appear, in mm of mercury, expresses the basal capillary resistance (before any treatment). Two measurements are made for each test at different sites on of the back.

The rats are treated by the oral route. After a predetermined time (generally 2, 4, 6 h) following the treatment, the test is repeated on different areas of the skin, until petechias appear, thus leading to a new low pressure index. All the measurements are done in the blind mode.

A percentage of variation in the capillary resistances of the animals treated compared to their basal capillary resistance is calculated for each compound studied, at each treatment time and compared with the control group (excipient only) or the reference group.

Effects on Induced Pleurisy in Rats:

The anti-inflammatory activity of the compounds is also studied by measuring the inhibition of the edema and the leukocyte migration after the induction of pleurisy in rats by the injection of carrageenin into the pleural cavity (Almeida et al., J. Pharmacol. Exp. Therap., 1980, Vol. 214: p. 74). The rats are treated orally using the compounds 2 h before the injection of carrageenin, and 2 and 4 h after this injection. After a predetermined time (6 h) following the induction of pleurisy, the rats are sacrificed; the pleural liquid is recovered by aspiration, and its volume is measured. The leukocytic cells are counted using the "cell counter" technique. The results are expressed as the number of leukocytes in the exudate expressed with respect to 100 g of animal weight and compared with those of the control lot.

Effect Against Septic Shock:

The activity in septic shock is studied in rats after the induction of the shock by an intravenous injection in the bolus of a lipopolysaccharide endotoxin (LPS: 15 mg/kg) of *E. col*, in a method similar to that described by Terashita et al., Eur. J. Pharmacol., 1985, Vol. 109: pp. 257–261. The arterial pressures are measured as a function of time and comparatively between treated groups and control groups (excipient alone). The compounds are administered intravenously or orally, 5 min or 2 h, respectively, before the injection of LPS.

Examples of Pharmacological Effects:

The compounds of the invention and their possible salts selectively increase, in a majority of the cases, the contraction of the animal veins produced by noradrenaline, by electrical stimulation, or by a depolarizing hyperpotassic solution.

The contractile effect of different compounds on the saphenous vein in rabbits, precontracted by a depolarizing "physiological" solution with a potassium concentration of 40 mM, is given as an illustration; the maximum effect produced by each compound is expressed as a percentage of the maximum contraction induced by depolarizing hyperpotassic solutions and as value of $ED_{50}$):

Compounds
  Emax (% maximum contraction)
  $ED_{50}$ (nM)
Example f
  15±1
  21
Example j
  16±6
  30
Example k
  26±9
  70
Example h
  29±6
  86
Example i
  18±1
  90
Example n
  24±3
  110
Example 3
  17±6
  36
Example 4
  29±11
  42
Example 7
  17±2
  36
Example 13
  21±3
  57
Example 18
  39±6
  88
Example 19
  20±8
  75
Example 20
  24±4
  110
Example 28
  29±2
  37
Example 38
  12±1
  160
Example 59
  18±4
  53
Example 57
  22±3
  41

For the purpose of illustration, the oral administration of certain compounds of the invention and of their possible salts increases the capillary resistance of rats at doses generally between 0.01 and 5 mg/kg:

Compounds
  Effects after 4 h
  Effect after 6 h
  (as a % of the control)
  (as a % of the control)
Example 3
  5 mg/kg
  27
  18
Example 18
  5 mg/kg
  25
  28
Example 21
  5 mg/kg
  10
  22
Example f
  0.1 mg/kg
  7
  17

Example h
 0.1 mg/kg
 19
 19
Example 1
 0.1 mg/kg
 37
 35
Example n*
 0.1 mg/kg
 45
 45
Example 2
 0.1 mg/kg
 25
 28
Example 10
 0.1 mg/kg
 25
 46
Example 15
 0.1 mg/kg
 20
 27
Example 28**
 0.1 mg/kg
 10
 13
 (granulometry: 0.5–0.6 mm)
 (granulometry: 0.6–0.7 mm)

For purposes of illustration, the oral administration of certain compounds of the invention and of their possible salts reduces the inflammatory hyperpermeability induced by zymosan in rats at doses of 0.1–5 mg/kg:
Compounds
 Effect after 2 h
 Effect after 4 h
 (as a % of the control)
 (as a % of the control)
Example 1
 5 mg/kg
 −28
 −28
Example n
 5 mg/kg
 0
 −21
Example 21
 5 mg/kg
 −22
 −21
Example 28
 5 mg/kg
 −29
 0
Example f
 0.1 mg/kg
 −15
 −22
Example j
 0.1 mg/kg
 −14
 −32
Example 3
 0.1 mg/kg
 −22
 −26
Example 14
 0.1 mg/kg
 −31
 −15
Example 17
 0.1 mg/kg
 −15
 −23
Example 25
 0.1 mg/kg
 −14
 −17
Example 26
 0.1 mg/kg
 −14
 −24
Example 38
 0.1 mg/kg
 −12
 −3
Example 59
 0.1 mg/kg
 −13
 +21

Moreover, the compounds of the invention and their possible salts have a very low toxicity. For example, after the single oral administration of 500 mg/kg in mice, no observable toxic effect and no mortality was observed with a majority of the compounds, particularly for Example f (1 g/kg), Example j, Example h (1 g/kg; diarrheas), Example n (1 g/kg; red urine), Example 3 (slight diarrheas), Example 5, Example 6, and Example 13 (1 g/kg). Most of the compounds were shown to be noncytotoxic (with the viability of the cells being measured by quantification of the cellular incorporation of neutral red) up to concentrations equal to their solubility in an aqueous medium on fibroblastic cell lines of mice (L929), particularly Example f, Example j, Example 3, Example 4, Example 20, Example 21 . . . .

Of the active compounds of the invention, particular mention is made of Example n.

Example n, for example, selectively potentiates the contractile response of the saphenous vein in rabbits due to noradrenaline (value of $ED_{50}$ reduced by a factor of ten and Emax increased by 30%), due to electrical stimulation (increase of 200% at 0.3 $\mu$m), and due to serotonin, in addition to the contractile effects observed in the presence of a response to a hyperpotassic solution. Under these depolarizing hyperpotassic conditions, the product contracts, for example, the jugular vein of rabbits ($ED_{50}$=16 nM), the rat ($ED_{50}$=50 nM), the perfused mesenteric venous network of rats ($ED_{50}$=300 nM), the carotid arteries of rats ($ED_{50}$=300 nM), rabbits ($ED_{50}$=120 nM), and the basilar artery of rabbits. In the model of the dorsal cutaneous chamber in hamsters, Example n (28 mg/kg injected in an i.v. bolus) reduces the veinule diameter but not the arteriolar diameter after the i.v. injection of histamine (1 mg/kg) and it reduces the vascular hyperpermeability introduced by the latter. The oral effect of Example n on the capillary resistance of the rat is dose dependent over a broad range of doses and its duration of action, of at least 6 h, correlates with its measured plasma concentrations.

After 2 h, the oral administration of 0.1 mg/kg of product of Example n decreases the hyperpermeability induced by histamine by 26% compared to the control group in rats.

The oral administration of 3×5 mg of this product significantly decreases the volume of pulmonary exudate after the induction of pleurisy by carrageenin in rats.

When administered in an i.v. bolus at a dose of 28 mg/kg 5 min before the induction of septic shock, the product of Example n increases the average arterial pressure by 20 mm of mercury compared to the control rat group.

The product of Example n does not affect the arterial pressure of the anesthetized rat after the i.v. injection in a bolus at least up to 28 mg/kg, nor that of the couscious rat after the oral administration of 0.1–5–50 mg/kg.

The preceding shows that the compounds of the invention and their possible salts can be used in human and animal therapy. They are particularly indicated for organic functional venous insufficiency and the hemorrhoid pathologies due to their vascular and anti-inflammatory components, as well as for typical inflammatory disorders and in the case of shock consisting of a large drop in arterial pressure. In the latter case, an improvement of the venous return is capable of maintaining the cardiac output, and hence the arterial pressure.

The functional venous insufficiency is characterized by a dilation and a hyperdistensibility of the superficial veins of the lower limbs, edemas, and impatience paresthesia of the restless leg type. This type of pathology may evolve toward organic venous insufficiency characterized by the development of varicose veins, valvular incontinence, and even phlebothrombosis and trophic disorders leading to ulcerous lesions.

In this venous pathology, an inflammatory component develops in the first stages and manifests itself more clearly in the advanced stages.

Due to their vasoconstrictive, anti-inflammatory effects particularly on the vascular hyperpermeability and their contractile effects on the cerebral arteries, the compounds of the invention and their possible salts are also indicated in migraine.

The present invention thus comprises the use of the compounds mentioned above and of their possible salts, as active ingredients in the preparation of drugs and of pharmaceutical compounds for human and veterinary use, comprising at least one of said compounds and salts in association with a physiologically acceptable support or diluent. The form of these drugs and pharmaceutical compositions will naturally depend on the desired route of administration, which notably may be oral, parenteral, topical (cutaneous), and rectal, and they can be formulated according to the standard techniques with the use of the usual supports and vehicles.

Thus, in the case of oral administration, they can be in the form of pills, tablets, gels, solutions, syrups, emulsions, suspensions, powders, granules, soft capsules, lyophilizates, microcapsules, and microgranules.

The pills, tablets, and gels contain the active ingredient together with a diluent (for example, lactose, dextrose, sucrose, mannitol, maltitol, xylitol, sorbitol, or cellulose), a lubricant (for example, silica, talc, or stearate), a binder (for example, starch, methylcellulose, or gum arabic), a disintegration agent (alginate, for example), and they are manufactured by known techniques, for example, mixing, granulation, pellet formation, coating, compression, etc.

The syrups can contain, as a support, glycerol, mannitol, and/or sorbitol. The solutions and suspensions can comprise water and other physiologically compatible solvents and a support such as a natural gum, agar-agar, sodium alginate, or polyvinyl alcohol.

For parenteral administration, the drugs and compositions can be in the form of solutions, emulsions, or suspensions comprising the active ingredient and an appropriate support or solvent such as sterile water or sterile isotonic saline solutions.

For the cutaneous application, the drugs and compositions can be in the form of an ointment, cream or gel, or in the form of an emulsion or suspension, solution, mousse, or powder.

For rectal application, the drugs and compositions can be in the form of a capsule, cream, emulsion, gel, mousse, ointment, or suppository.

What is claimed is:

1. A method for the treatment of illness associated with an alteration in venous function and/or inflammatory edems which comprises administering a sufficient amount of a tricyclic derivative or a pharmaceutically-acceptable salt thereof having the general formula:

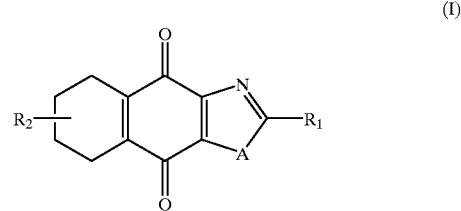

(I)

in which:
A is either a sulfur or an oxygen atom or an $R_3N$ radical where $R_3$ is a hydrogen atom, a $C_1$-$C_5$ alkyl radical, a substituted or unsubstituted aromatic ring, or a substituted or unsubstituted heteroaromatic ring;

$R_1$ is either a $C_1$-$C_5$ alkyl radical, or an $R_4NH$ radical where $R_4$ is a hydrogen atom, a $C_1$-$C_5$ alkyl radical, a substituted or unsubstituted aromatic ring, or a substituted or unsubstituted heteroaromatic ring, an aromatic ring that may or may not be substituted by one or more acceptor or donor groups, or a heteroaromatic ring having one or more heteroatoms, which may or may not be substituted by acceptor or donor groups;

$R_2$ is a hydrogen atom, halogen atom, a $C_1$-$C_5$ alkyl radical, an oxygen atom that may or may not be substituted by a $C_1$-$C_5$ alkyl radical, or an $NR_5R_{5'}$ radical where $R_5$ and $R_{R'}$ are, independently of each other, a hydrogen atom, an oxygen atom or monovalent $C_1$-$C_5$ organic radical, for treatment of illness connected with an alteration in venous function and/or inflammatory edema.

2. The method of claim 1 wherein said treatment is for the treatment of functional and organic venous insufficiency.

3. The method of claim 1 wherein said treatment is for the treatment of hemorrhoidal pathologies.

4. The method of claim 1 wherein said treatment is for the treatment of migraines.

5. The method of claim 1 wherein said treatment is for the treatment of dermatological and cardiovascular osteoarticular inflammations.

6. The method of claim 1 wherein said treatment is for the treatment of states of shock consisting of a large drop in arterial blood pressure.

7. The method of claim 6, wherein said shock is septic shock.

8. The method of claim 1 wherein said tricyclic derivative is 4,9-dihydro-4,9-dioxo-2-(2-furyl)-naphtho[2,3-d]thiazole.

* * * * *

UNITED STATES PATENT AND TRADEMARK OFFICE
CERTIFICATE OF CORRECTION

PATENT NO.   : 6,262,095 B1  
DATED        : July 17, 2001  
INVENTOR(S)  : Odile Boutherin-Falson et al.

It is certified that error appears in the above-identified patent and that said Letters Patent is hereby corrected as shown below:

<u>Title page,</u>  
Item [54] should read -- USE OF TRICYCLIC DERIVATIVES OF 1,4-DIHYDRO-1,4-DIOXO-1H-NAPHTHALENE, NOVEL COMPOUNDS OBTAINED AND THEIR APPLICATION IN THERAPY --.

<u>Column 38,</u>  
Line 62, change "4,9-dihydro-4,9-dioxo-5-methyl- 2-phenylnaptho[2,3-d]-thiazole" to read -- 4,9-dihydro-4,9-dioxo-5-methyl-2-phenylnaptho[2,3-d]-thiazole --.

<u>Column 39,</u>  
Line 6, change "Examiple c" to read -- Example c --.

<u>Column 45,</u>  
Line 28, change "E. Col," to read -- E. Coli, --

<u>Column 50,</u>  
Line 22, change "edems" to read -- edema --.  
Line 46, change "ring," to read -- ring, or --.  
Line 54, change "$R_{R'}$" to read -- $R_{5'}$ -- .

Signed and Sealed this

Eighteenth Day of June, 2002

*Attest:*

*Attesting Officer*

JAMES E. ROGAN  
*Director of the United States Patent and Trademark Office*